(12) United States Patent
Hastewell et al.

(10) Patent No.: US 9,296,810 B2
(45) Date of Patent: Mar. 29, 2016

(54) FIBRONECTIN-BASED BINDING MOLECULES AND USES THEREOF

(75) Inventors: John Hastewell, Cambridge, MA (US); Andreas Loew, Cambridge, MA (US)

(73) Assignee: NOVARTIS AG, Basel (CH)

( * ) Notice: Subject to any disclaimer, the term of this patent is extended or adjusted under 35 U.S.C. 154(b) by 1115 days.

(21) Appl. No.: 12/989,494

(22) PCT Filed: May 4, 2009

(86) PCT No.: PCT/EP2009/055365
§ 371 (c)(1),
(2), (4) Date: Dec. 3, 2010

(87) PCT Pub. No.: WO2009/133208
PCT Pub. Date: Nov. 5, 2009

(65) Prior Publication Data
US 2011/0038866 A1    Feb. 17, 2011

Related U.S. Application Data

(60) Provisional application No. 61/050,142, filed on May 2, 2008.

(51) Int. Cl.
| C07K 14/78 | (2006.01) |
| C07K 16/00 | (2006.01) |
| C07K 16/18 | (2006.01) |
| C07K 16/28 | (2006.01) |

(52) U.S. Cl.
CPC ............... *C07K 14/78* (2013.01); *C07K 16/005* (2013.01); *C07K 16/18* (2013.01); *C07K 16/2863* (2013.01); *C07K 2317/31* (2013.01); *C07K 2318/20* (2013.01); *C07K 2319/31* (2013.01); *C07K 2319/70* (2013.01)

(58) Field of Classification Search
None
See application file for complete search history.

(56) References Cited

U.S. PATENT DOCUMENTS

| 6,462,189 | B1 | 10/2002 | Koide |
| 6,649,340 | B1 | 11/2003 | Crea |
| 6,673,901 | B2 | 1/2004 | Koide |
| 6,703,199 | B1 | 3/2004 | Koide |
| 7,078,490 | B2 | 7/2006 | Koide |
| 7,119,171 | B2 | 10/2006 | Koide |
| 7,153,661 | B2 | 12/2006 | Koide |
| 7,847,062 | B2 | 12/2010 | Chen et al. |
| 7,858,090 | B2 | 12/2010 | Koide |
| 7,981,620 | B2 | 7/2011 | Koide |
| 8,062,858 | B2 | 11/2011 | Koide |
| 8,106,162 | B2 | 1/2012 | Koide |
| 8,258,265 | B2 | 9/2012 | Koide |
| 8,263,741 | B2 | 9/2012 | Koide |
| 2002/0019517 | A1 | 2/2002 | Koide |
| 2003/0157132 | A1* | 8/2003 | Itami et al. ............... 424/225.1 |
| 2003/0186385 | A1 | 10/2003 | Koide |
| 2006/0240018 | A1* | 10/2006 | Koide ........................ 424/145.1 |
| 2009/0299040 | A1 | 12/2009 | Camphausen et al. |
| 2010/0322930 | A1 | 12/2010 | Kolbinger et al. |
| 2011/0038866 | A1 | 2/2011 | Hastewell et al. |
| 2012/0135516 | A1 | 5/2012 | Koide |
| 2012/0208704 | A1 | 8/2012 | Loew et al. |

FOREIGN PATENT DOCUMENTS

| WO | WO 00/34784 A1 | 6/2000 |
| WO | 01/64942 A1 | 9/2001 |
| WO | 02/04523 A2 | 1/2002 |
| WO | 02/32925 A2 | 4/2002 |
| WO | 03/104418 A2 | 12/2003 |
| WO | WO 2005056764 A2 * | 6/2005 |
| WO | WO 2005118642 A2 * | 12/2005 |
| WO | 2008/144610 A1 | 11/2008 |
| WO | 2009023184 A2 | 2/2009 |
| WO | 2009058379 A2 | 5/2009 |
| WO | 2009/083804 A2 | 7/2009 |
| WO | 2009/133208 A1 | 11/2009 |
| WO | 2010/060095 A1 | 5/2010 |
| WO | 2011/051333 A1 | 5/2011 |
| WO | 2012/016245 A2 | 2/2012 |

OTHER PUBLICATIONS

Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Xu et al (Chemistry & Biology. 9: 933-942, 2002).*
Rudikoff et al (Proc. Natl. Acad. Sci. USA 1982 vol. 79: p. 1979-1983).*
Batori et al., "Exploring the potential of the monobody scaffold: effects of loop elongation on the stability of a fibronectin type III domain," Protein Engineering 15(12):1015-1020 (2002).
Koide et al., "Probing protein conformational changes in living cells by using designer binding proteins Application to the estrogen receptor," Proceedings of the National Academy of Sciences of the Unites States of America 99 (3):1253-1258 (2002).
Lipovsek at al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology 368(4):1024-1041 (2007).

(Continued)

*Primary Examiner* — Brad Duffy
(74) *Attorney, Agent, or Firm* — John Prince

(57) ABSTRACT

The invention provides fibronectin type III (Fn3)-based binding molecules that bind to a specific target antigen. The invention further provides bispecific Fn3-based binding molecules that bind to two or more targets simultaneously. The Fn3-based binding molecules of the invention can also be linked together to form multispecific Fn3-based binding molecules, and/or can be conjugated to a non-Fn3 moiety, such as, Human Serum Albumin (HSA), for improved half life and stability. The invention also provides methods for generating, screening and using Fn3-based binding molecules in a variety of therapeutic and diagnostic applications.

1 Claim, 18 Drawing Sheets

(56) References Cited

OTHER PUBLICATIONS

Bloom L et al: FN3: a new protein scaffold reaches the clinic, Drug Discovery Today. Elsevier. Rahway. NJ. US. vol. 14. No. 19-20. Oct. 1, 2009. pp. 949-955.
Bork P. et al.: "Proposed acquisition of an animal protein domain by bacteria" Proc. Natl. Acad. Sci. USA, vol. 89, Dec. 9, 1992, pp. 8990-8994.
Dickinson C D et al: "Crystal structure of the tenth type III cell adhesion module of human fibronectin" Journal of Molecular Biology. London. GB. vol. 236. No. 4. Mar. 4, 1994 • pp. 1079-1092.
International Preliminary Report on Patentability for PCT/EP2009/055365 dated Nov. 2, 2010.
International Preliminary Report on Patentablility & Written Opinion for PCT/EP2010/066250 dated Apr. 30, 2012.
International Preliminary Report on Patentablility & Written Opinion for PCT/IB2008/003962 dated Jun. 29, 2010.
International Preliminary Report on Patentablility & Written Opinion for PCT/US2011/046160 dated Feb. 5, 2013.
International Search Report for PCT/US2011/046160 dated Mar. 28, 2012.
International Search Report for PCT/EP2009/055365 dated Oct. 19, 2009.
International Search Report for PCT/EP2010/066250 dated Feb. 21, 2011.
International Search Report for PCT/IB2008/003962 dated Feb. 15, 2010.
Karatan E et al: "Molecular Recognition Properties of FN3 Monobodies that Bind the Src SH3 Domain" Chemistry and Biology. Current Biology. London. GB. vol. 11. No. 6. Jun. 1, 2004. pp. 835-844.
Koide A et al: "The fibronectin type III domain as a scaffold for novel binding protein" Journal of Molecular Biology. London. GB. vo 1 • 284. No. 4. Dec. 11, 1998. pp. 1141-1151.
Main A L et al: "The three-dimensional structure of the tenth type III module of fibronectin: An insight into RGD-mediated interactions". Cell. Cell Press. Cambridge. NA. US. vol. 71. No. 4. Nov. 13, 1992. pp. 671-678.
Miescher et al: "CHO expression of a novel humaqn recombinant IgI anti-RhD antibody isolated by phage display" British Journal of Haematology, Wiley-Blackwell Publishing Ltd, GB, vol. 111, Jan. 1, 2000, pp. 157-166.
Parker, et al, Anitbody micis based on human fibronectin type three domain engineered for thermostability and hig-affinity binding to vascular endothelial growth factor receptor two. Protein Engineering, Design and Selection (Sep. 2005) 18 (9): 435-444.

* cited by examiner

| SEQ ID | | | | | 51 | | | | | 96 |
|---|---|---|---|---|---|---|---|---|---|---|
| 7  | VSDVPRDLEV | VAATPTSLLI | SWDAPAVTVR | YYRITYGKTE | GHRHSHEFTV | PGSKSTATIS | GLKHGDDYTI | TVLAVTGRGD | SPASSKPISI | NYRMEK |
| 8  | VSDVPRDLEV | VAATPTSLLI | SWDAPAVTVR | YYRITYGRTD | AKSTRKEFTV | PGSKSTATIG | ELKRGRDYTI | TVLAVTGRGD | SPASSKPISI | NYRPEK |
| 9  | VSDVPRDLEV | VAATPTSLLI | SWDAPAVTVR | YYRITYGQLD | KKHHDAEFTV | PGSKSTATIT | RLKRGRDYTI | TVLAVTGRGD | SPASSKPISI | NYSPER |
| 10 | VSDVPRDLEV | VAATPTSLLI | SWDAPAVTVR | YYRITYGKTG | HKSSDHEFTV | PGSKSTATIG | GMKGGVDYTI | TVLAVTGRGD | SPASSKPISI | NYRFER |
| 11 | VSDVPRDLEV | VAATPTSLLI | SWDAPAVTVR | YYRITYGKKD | RASHLKEFTV | PGSKSTATIG | HIKGGYDYTI | TVLAVTGRGD | SPASSKPISI | NYSGEP |
| 12 | VSDVPRDLEV | VAATPTSLLI | SWDAPAVTVR | YYRITYGRTK | GKSKLKEFTV | PGSKSTATIP | GLKQGEDYTI | TVLAVTGRGD | SPASSKPISI | NYMFER |
| 13 | VSDVPRDLEV | VAATPTSLLI | SWDAPAVTVR | YYRITYGTSV | DDRKLREFTV | PGSKSTATIS | RLKRGRDYTI | TVLAVTGRGD | SPASSKPISI | NYRAEN |
| 14 | VSDVPRDLEV | VAATPTSLLI | SWDAPAVTVR | YYRITYGVLS | STKHLKEFTV | PGSKSTATIS | GLKLGRDYTI | TVLAVTGRGD | SPASSKPISI | NYRMES |
| 15 | VSDVPRDLEV | VAATPTSLLI | SWDAPAVTVR | YYRITYGSRA | SHRKLTEFTV | PGSKSTATIS | GLKTGRDYTI | TVLAVTGRGD | SPASSKPISI | NYRTEH |
| 16 | VSDVPRDLEV | VAATPTSLLI | SWDAPAVTVR | YYRITYGITG | KEKSVEFTV  | PGSKSTATIR | DVKKGKDYTI | TVLAVTGRGD | SPASSKPISI | NYRAET |
| 17 | VSDVPRDLEV | VAATPTSLLI | SWDAPAVTVR | YYRITYGQRV | GKTKVHEFTV | PGSKSTATIR | GLKRGKDYTI | TVLAVTGRGD | SPASSKPISI | NYFPET |
| 18 | VSDVPRDLEV | VAATPTSLLI | SWDAPAVTVR | YYRITYGHTA | KTRHHHEFTV | PGSKSTATIC | KSRRGSDYTI | TVYLAVTGRGD | SPASSKPISI | NYQAET |
| 19 | VSDVPRDLEV | VAATPTSLLI | SWDAPAVTVR | YYRITYGYGA | ANRRAHEFTV | PGSKSTATIS | GLKRGRDYTI | TVLAVTGRGD | SPASSKPISI | NYRHEL |
| 20 | VSDVPRDLEV | VAATPTSLLI | SWDAPAVTVR | YYRITYGKLG | GKPKVREFTV | PGSKSTATIL | GLKPGLDYTI | TVLAVTGRGD | SPASSKPISI | NYIHEQ |
| 21 | VSDVPRDLEV | VAATPTSLLI | SWDAPAVTVR | YYRITYGDSR | HEPRAHEFTV | PGSKSTATIT | GCKRGHDYTI | TVLAVTGRGD | SPASSKPISI | NYRYEH |
| 22 | VSDVPRDLEV | VAATPTSLLI | SWDAPAVTVR | YYRITYGKSH | GERQKHEFTV | PGSKSTATIS | DYRQGGDYTI | TVLAVTGRGD | SPASSKPISI | NYKGEL |
| 23 | VSDVPRDLEV | VAATPTSLLI | SWDAPAVTVR | YYRITYGVMG | DTKKVHEFTV | PGSKSTATIE | RIKLGRDYTI | TVLAVTGRGD | SPASSKPISI | NYRKEH |
| 24 | VSDVPRDLEV | VAATPTSLLI | SWDAPAVTVR | YYRITYGEAS | KMHRQHEFTV | PGSKSTATIS | RIKRGTDYTI | TVLAVTGRGD | SPASSKPISI | NYSPES |
| 25 | VSDVPRDLEV | VAATPTSLLI | SWDAPAVTVR | YYRITYGEKP | RKYRSSEFTV | PGSKSTATIR | HSKHGKDYTI | TVLAVTGRGD | SPASSKPISI | NYMREI |
| 26 | VSDVPRDLEV | VAATPTSLLI | SWDAPAVTVR | YYRITYGKTA | RKYHMQEFTV | PGSKSTATIV | GIKRGTDYTI | TVLAVTGRGD | SPASSKPISI | NYNSEH |
| 27 | VSDVPRDLEV | VAATPTSLLI | SWDAPAVTVR | YYRITYGLTK | RKSLISEFTV | PGSKSTATIT | GLKAGKDYTI | TVLAVTGRGD | SPASSKPISI | NYKTEN |
| 28 | VSDVPRDLEV | VAATPTSLLI | SWDAPAVTVR | YYRITYGKVK | AKAPLVEFTV | PGSKSTATIS | SLKTGKDYTI | TVLAVTGRGD | SPASSKPISI | NYRVEG |
| 29 | VSDVPRDLEV | VAATPTSLLI | SWDAPAVTVR | YYRITYGDRA | KNTRIKEFTV | PGSKSTATIS | GLKRGRDYTI | TVLAVTGRGD | SPASSKPISI | NYRLEG |
| 30 | VSDVPRDLEV | VAATPTSLLI | SWDAPAVTVR | YYRITYGIPA | KKHHTHEFTV | PGSKSTATIT | GLKSGVDYTI | TVLAVTGRGD | SPASSKPISI | NYRTET |
| 31 | VSDVPRDLEV | VAATPTSLLI | SWDAPAVTVR | YYRITYGEVH | GHHTAHEFTV | PGSKSTATIV | RLKRGKDYTI | TVLAVTGRGD | SPASSKPISI | NYCPER |
| 32 | VSDVPRDLEV | VAATPTSLLI | SWDAPAVTVR | YYRITYGMIS | GDKRRREFTV | PGSKSTATID | RLKLGRDYTI | TVLAVTGRGD | SPASSKPISI | NYRLES |
| 33 | VSDVPRDLEV | VAATPTSLLI | SWDAPAVTVR | YYRITYGVMH | DKHPKKEFTV | PGSKSTATIS | GLKRGRDYTI | TVLAVTGRGD | SPASSKPISI | NYKSEA |
| 34 | VSDVPRDLEV | VAATPTSLLI | TWDAPAVTVR | YYRITYGVAG | KTKPRSEFTV | PGSKSTATIP | HLKLGHDYTI | TVLAVTGRGD | SPASSKPISI | NYRAEH |
| 35 | VSDVPRDLEV | VAATPTSLLI | SWDAPAVTVR | YYRITYGKNG | RHNLDHEFTV | PGSKSTATIS | GLKRGVDYTI | TVLAVTGRGD | SPASSKPISI | NYHNEN |
| 36 | VSDVPRDLEV | VAATPTSLLI | SWDAPAVTVR | YYRITYGNIV | AANALPEFTV | PGSKSTATIT | GLMSGIDYTI | TVLAVTGRGD | SPASSKPISI | NYSTEY |
| 37 | VSDVPRDLEV | VAATPTSLLI | SWDAPAVTVR | YYRITYGKLS | QPTKRREFTV | PGSKSTATIT | RLKPGLDYTI | TVLAVTGRGD | SPASSKPISI | NYHHEL |
| 38 | VSDVPRDLEV | VAATPTSLLI | SWDAPAVTVR | YYRITYGKSS | HNSAAKHEFTV| PGSKSTATIA | RLKSGTDYTI | TVLAVTGRGD | SPASSKPISI | NYKPEY |
| 39 | VSDVPRDLEV | VAATPTSLLI | SWDAPAVTVR | YYRITYGKKH | KHTTVREFTV | PGSKSTATIA | GKSLGGDYTI | TVLAVTGRGD | SPASSKPISI | NYTSET |
| 40 | VSDVPRDLEV | VAATPTSLLI | SWDAPAVTVR | YYRITYGRPG | HDSKVHEFTV | PGSKSTATID | GAKKGHDYTI | TVLAVTGRGD | SPASSKPISI | NYIMEH |
| 41 | VSNIPKDLEV | VAATPTSLLI | SWDAPAVTVR | YYRITYGQIN | NGQSNVEFTV | PGSKSTATIS | PSKLGLDYTI | TVLAVTGRGD | SPASSKPISI | NYLSET |
| WT | VSDVPRDLEV | VAATPTSLLI | SWDAPAVTVR | YYRITYGETG | GNSPVQEFTV | PGSKSTATIS | GLKPGVDYTI | TVLAVTGRGD | SPASSKPISI | NYRTEI |
| 42-Cons | VSDVPRDLEV | VAATPTSLLI | SWDAPAVTVR | YYRITYGKTG | GKSKVHEFTV | PGSKSTATIS | GLKRGRDYTI | TVLAVTGRGD | SPASSKPISI | NYRPEH |

| SEQ ID | | | | | | | | | |
|---|---|---|---|---|---|---|---|---|---|
| 88 | VSDVPRDLEV | VAATPTSLLI | SWDAPAVTVR | YYRITYGESS | SS..RRQEFT | VPGSKSTATI | SGEBSYVDYT | ITVYAVTGRG | ESPASSKPIS | INYAEER |
| 89 | VSDVPRDLEV | VAATPTSLLI | SWDAPAVTVR | YYRITYGEGR | HP..SYQEFT | VPGSKSTATI | SFSYSRVDYT | ITVYAVTGRG | ESPASSKPIS | INYSRER |
| 90 | VSDVPRDLEV | VAATPTSLLI | SWDAPAVTVR | YYRITYGEGE | RP...YQEFT | VPGSKSTATI | SYAHYSVDYT | ITVYAVTGRG | ESPASSKPIS | INYERRS |
| 91 | VSDVPRDLEV | VAATPTSLLI | SWDAPAVTVR | YYRITYGEYQ | R...SRQEFT | VPGSKSTATI | SSYGGYVDYT | ITVYAVTGRG | ESPASSKPIS | INYRSLR |
| 92 | VSDVPRDLEV | VAATPTSLLI | SWDAPAVTVR | YYRITYGEYE | R...YRQEFT | VPGSKSTATI | SSQSRYVDYT | ITVYAVTGRG | ESPASSKPIS | INYGRPA |
| 93 | VSDVPRDLEV | VAATPTSLLI | SWDAPAVTVR | YYRITYGEYP | R...EYQEFT | VPGSKSTATI | SRYGYHVDYT | ITVYAVTGRG | ESPASSKPIS | INYSGYS |
| 94 | VSDVPRDLEV | VAATPTSLLI | SWDAPAVTVR | YYRITYGEYE | H...YYQEFT | VPGSKSTATI | SFYAGGVDYT | ITVYAVTGRG | ESPASSKPIS | INYSESE |
| 95 | VSDVPRDLEV | VAATPTSLLI | SWDAPAVTVR | YYRITYGEYE | Y...ARQEFT | VPGSKSTATI | SRLYRRVDYT | ITVYAVTGRG | ESPASSKPIS | INYRSA |
| 96 | VSDVPRDLEV | VAATPTSLLI | SWDAPAVTVR | YYRITYGEYH | Y...SEQEFT | VPGSKSTATI | SYYBRRVDYT | ITVYAVTGRG | ESPASSKPIS | INYHSSR |
| 97 | VSDVPRDLEV | VAATPTSLLI | SWDAPAVTVR | YYRITYGEQR | Y...LRQEFT | VPGSKSTATI | SSRSARVDYT | ITVYAVTGRG | ESPASSKPIS | INYFYSA |
| 98 | VSDVPRDLEV | VAATPTSLLI | SWDAPAVTVR | YYRITYGERS | S...RSQEFT | VPGSKSTATI | SHSREPVDYT | ITVYAVTGRG | ESPASSKPIS | INYCYRY |
| 99 | VSDVPRDLEV | VAATPTSLLI | SWDAPAVTVR | YYRITYGESQ | S...HSQEFT | VPGSKSTATI | SHPSRPVDYT | ITVYAVTGRG | ESPASSKPIS | INYPRSE |
| 100 | VSDVPRDLEV | VAATPTSLLI | SWDAPAVTVR | YYRITYGEEE | E...HPQEFT | VPGSKSTATI | SSPORGVDYT | ITVYAVTGRG | ESPASSKPIS | INYYSYY |
| 101 | VSDVPRDLEV | VAATPTSLLI | SWDAPAVTVR | YYRITYGEES | S...RPQEFT | VPGSKSTATI | SQARARVDYT | ITVYAVTGRG | ESPASSKPIS | INYRYR |
| 102 | VSDVPRDLEV | VAATPTSLLI | SWDAPAVTVR | YYRITYGEYG | A...LEQEFT | VPGSKSTATI | SR8QAEVDYT | ITVYAVTGRG | ESPASSKPIS | INYASYY |
| 103 | VSDVPRDLEV | VAATPTSLLI | SWDAPAVTVR | YYRITYGESR | E...GGQEFT | VPGSKSTATI | SSYQSEVDYT | ITVYAVTGRG | ESPASSKPIS | INYARSR |
| 104 | VSDVPRDLEV | VAATPTSLLI | SWDAPAVTVR | YYRITYGEBGQ | Q...GGQEFT | VPGSKSTATI | SAYRGPVDYT | ITVYAVTGRG | ESPASSKPIS | INYYGSY |
| 105 | VSDVPRDLEV | VAATPTSLLI | SWDAPAVTVR | YYRITYGEGR | R...YGQEFT | VPGSKSTATI | SELLSEVDYT | ITVYAVTGRG | ESPASSKPIS | INYSLRY |
| 106 | VSDVPRDLEV | VAATPTSLLI | SWDAPAVTVR | YYRITYGESG | Y...RYQEFT | VPGSKSTATI | SGYREHVDYT | ITVYAVTGRG | ESPASSKPIS | INYQESY |
| 107 | VSDVPRDLEV | VAATPTSLLI | SWDAPAVTVR | YYRITYGESG | R...RGQEFT | VPGSKSTATI | SSPSLEVDYT | ITVYAVTGRG | ESPASSKPIS | INYSGY |
| 108 | VSDVPRDLEV | VAATPTSLLI | SWDAPAVTVR | YYRITYGEPR | R...RYQEFT | VPGSKSTATI | SPGGOSVDYT | ITVYAVTGRG | ESPASSKPIS | INYRGY |
| 109 | VSDVPRDLEV | VAATTSLHI | SWDAPAVTVR | YYRITYGESG | RG..A.QEFT | VPGSKSTATI | SGLGPPVDYT | ITVYAVTGRG | ESPASSKPIS | INYRSQH |
| 110 | VSDVPRDLEV | VAATPTSLHI | SWDAPAVTVR | YYRITYGESS | GYAERGQEFT | VPGSKSTATI | SSPGARVDYT | ITVYAVTGRG | ESPASSKPIS | INYSSLG |
| 111 | VSDVPRDLEV | VAATPTSLHI | SWDAPAVTVR | YYRITYGESE | GGSSR.SQEFT | VPGSKSTATI | SRSYQPVDYT | ITVYAVTGRG | ESPASSKPIS | INYGSXP |
| 112 | VSDVPRDLEV | VAATPTSLHI | SWDAPAVTVR | YYRITYGERR | YHQGRRQEFT | VPGSKSTATI | SRYGSSVDYT | ITVYAVTGRG | ESPASSKPIS | INYAYG |
| 113 | VSDVPRDLEV | VAATPTSLHI | SWDAPAVTVR | YYRITYGEQR | GQYGSSQEFT | VPGSKSTATI | SSPEGSVDYT | ITVYAVTGRG | ESPASSKPIS | INYSRSE |
| 114 | VSDVPRDLEV | VAATPTSLHI | SWDAPAVTVR | YYRITYGEQR | YSYYGQQEFT | VPGSKSTATI | SSGRSSVDYT | ITVYAVTGRG | ESPASSKPIS | INYRRSY |
| 115 | VSDVPRDLEV | VAATPTSLHI | SWDAPAVTVR | YYRITYGERP | ASYRAAQEFT | VPGSKSTATI | SSYSYSVDYT | ITVYAVTGRG | ESPASSKPIS | INYRRSG |
| 116 | VSDVPRDLEV | VAATPTSLHI | SWDAPTVTVR | YYRITYGEPQ | ASHRPYQEFT | VPGSKSTATI | SSRSQSVDYT | ITVYAVTGRG | ESPASSKPIS | INYLREL |

*Fig. 8 cont.*

SEQUENCE LISTING

<160> NUMBER OF SEQ ID NOS: 123

<210> SEQ ID NO 1
<211> LENGTH: 96
<212> TYPE: PRT
<213> ORGANISM: Homo Sapiens

-continued

```
<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

<210> SEQ ID NO 2
<211> LENGTH: 96
<212> TYPE: PRT
<213> ORGANISM: Homo Sapiens

<400> SEQUENCE: 2

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

<210> SEQ ID NO 3
<211> LENGTH: 96
<212> TYPE: PRT
<213> ORGANISM: Homo Sapiens

<400> SEQUENCE: 3

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

<210> SEQ ID NO 4
<211> LENGTH: 96
<212> TYPE: PRT
<213> ORGANISM: Homo Sapiens
```

```
<220> FEATURE:
<221> NAME/KEY: misc_feature
<222> LOCATION: (23)..(29)
<223> OTHER INFORMATION: Xaa can be any naturally occurring amino acid
<220> FEATURE:
<221> NAME/KEY: misc_feature
<222> LOCATION: (52)..(55)
<223> OTHER INFORMATION: Xaa can be any naturally occurring amino acid
<220> FEATURE:
<221> NAME/KEY: misc_feature
<222> LOCATION: (77)..(86)
<223> OTHER INFORMATION: Xaa can be any naturally occurring amino acid

<400> SEQUENCE: 4

Val Ser Asp Val Pro Arg Asp Leu Glu Val Val Ala Ala Thr Pro Thr
1               5                   10                  15

Ser Leu Leu Ile Ser Trp Xaa Xaa Xaa Xaa Xaa Xaa Xaa Arg Tyr Tyr
            20                  25                  30

Arg Ile Thr Tyr Gly Glu Thr Gly Gly Asn Ser Pro Val Gln Glu Phe
            35                  40                  45

Thr Val Pro Xaa Xaa Xaa Xaa Thr Ala Thr Ile Ser Gly Leu Lys Pro
        50                  55                  60

Gly Val Asp Tyr Thr Ile Thr Val Tyr Ala Val Thr Xaa Xaa Xaa Xaa
65                  70                  75                  80

Xaa Xaa Xaa Xaa Xaa Xaa Pro Ile Ser Ile Asn Tyr Arg Thr Glu Ile
                85                  90                  95

<210> SEQ ID NO 5
<211> LENGTH: 96
<212> TYPE: PRT
<213> ORGANISM: Homo Sapiens
<220> FEATURE:
<221> NAME/KEY: MISC_FEATURE
<222> LOCATION: (38)..(44)
<223> OTHER INFORMATION: Glx as used herein can be any naturally
      occurring amino acid
<220> FEATURE:
<221> NAME/KEY: MISC_FEATURE
<222> LOCATION: (60)..(64)
<223> OTHER INFORMATION: Glx as used herein can be any naturally
      occurring amino acid
<220> FEATURE:
<221> NAME/KEY: MISC_FEATURE
<222> LOCATION: (93)..(93)
<223> OTHER INFORMATION: Glx as used herein can be any naturally
      occurring amino acid
<220> FEATURE:
<221> NAME/KEY: MISC_FEATURE
<222> LOCATION: (95)..(96)
<223> OTHER INFORMATION: Glx as used herein can be any naturally
      occurring amino acid
<220> FEATURE:
<221> NAME/KEY: MISC_FEATURE
<222> LOCATION: (95)..(96)
<223> OTHER INFORMATION: Glx as used herein can be any naturally
      occurring amino acid

<400> SEQUENCE: 5

Val Ser Asp Val Pro Arg Asp Leu Glu Val Val Ala Ala Thr Glx Glx
1               5                   10                  15

Ser Leu Leu Ile Ser Trp Asp Ala Pro Ala Val Thr Val Arg Tyr Tyr
            20                  25                  30

Arg Ile Thr Tyr Gly Glx Glx Glx Glx Glx Glx Val Gln Glu Phe
            35                  40                  45

Thr Val Pro Gly Ser Lys Ser Thr Ala Thr Ile Glx Glx Glx Glx Glx
        50                  55                  60

Gly Glx Asp Tyr Thr Ile Thr Val Tyr Ala Val Thr Gly Arg Gly Asp
```

65                  70                  75                  80

Ser Pro Ala Ser Ser Lys Pro Ile Ser Ile Asn Tyr Glx Thr Glx Glx
                85                  90                  95

<210> SEQ ID NO 6
<211> LENGTH: 96
<212> TYPE: PRT
<213> ORGANISM: Homo Sapiens
<220> FEATURE:
<221> NAME/KEY: MISC_FEATURE
<222> LOCATION: (15)..(16)
<223> OTHER INFORMATION: Glx as used herein can be any naturally
      occurring amino acid
<220> FEATURE:
<221> NAME/KEY: misc_feature
<222> LOCATION: (23)..(29)
<223> OTHER INFORMATION: Xaa can be any naturally occurring amino acid
<220> FEATURE:
<221> NAME/KEY: MISC_FEATURE
<222> LOCATION: (38)..(44)
<223> OTHER INFORMATION: Glx as used herein can be any naturally
      occurring amino acid
<220> FEATURE:
<221> NAME/KEY: misc_feature
<222> LOCATION: (52)..(55)
<223> OTHER INFORMATION: Xaa can be any naturally occurring amino acid
<220> FEATURE:
<221> NAME/KEY: MISC_FEATURE
<222> LOCATION: (60)..(64)
<223> OTHER INFORMATION: Glx as used herein can be any naturally
      occurring amino acid
<220> FEATURE:
<221> NAME/KEY: MISC_FEATURE
<222> LOCATION: (66)..(66)
<223> OTHER INFORMATION: Glx as used herein can be any naturally
      occurring amino acid
<220> FEATURE:
<221> NAME/KEY: misc_feature
<222> LOCATION: (77)..(86)
<223> OTHER INFORMATION: Xaa can be any naturally occurring amino acid
<220> FEATURE:
<221> NAME/KEY: MISC_FEATURE
<222> LOCATION: (93)..(93)
<223> OTHER INFORMATION: Glx as used herein can be any naturally
      occurring amino acid
<220> FEATURE:
<221> NAME/KEY: MISC_FEATURE
<222> LOCATION: (95)..(96)
<223> OTHER INFORMATION: Glx as used herein can be any naturally
      occurring amino acid
<220> FEATURE:
<221> NAME/KEY: MISC_FEATURE
<222> LOCATION: (95)..(96)
<223> OTHER INFORMATION: Glx as used herein can be any naturally
      occurring amino acid

<400> SEQUENCE: 6

Val Ser Asp Val Pro Arg Asp Leu Glu Val Val Ala Ala Thr Glx Glx
1               5                   10                  15

Ser Leu Leu Ile Ser Trp Xaa Xaa Xaa Xaa Xaa Xaa Xaa Arg Tyr Tyr
                20                  25                  30

Arg Ile Thr Tyr Gly Glx Glx Glx Glx Glx Glx Glx Val Gln Glu Phe
            35                  40                  45

Thr Val Pro Xaa Xaa Xaa Xaa Thr Ala Thr Ile Glx Glx Glx Glx Glx
        50                  55                  60

Gly Glx Asp Tyr Thr Ile Thr Val Tyr Ala Val Thr Xaa Xaa Xaa Xaa
65                  70                  75                  80

Xaa Xaa Xaa Xaa Xaa Xaa Pro Ile Ser Ile Asn Tyr Glx Thr Glx Glx
                85                  90                  95

```
<210> SEQ ID NO 7
<211> LENGTH: 96
<212> TYPE: PRT
<213> ORGANISM: Homo Sapiens

<400> SEQUENCE: 7

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Lys Thr Glu Gly His Arg His Ser His Glu Phe
        35                  40                  45

Thr Val Pro Gly Ser Lys Ser Thr Ala Thr Ile Ser Gly Leu Lys His
    50                  55                  60

Gly Asp Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Met Glu Lys
                85                  90                  95

<210> SEQ ID NO 8
<211> LENGTH: 96
<212> TYPE: PRT
<213> ORGANISM: Homo Sapiens

<400> SEQUENCE: 8

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Arg Thr Asp Ala Lys Ser Thr Arg Lys Glu Phe
        35                  40                  45

Thr Val Pro Gly Ser Lys Ser Thr Ala Thr Ile Gly Glu Leu Lys Arg
    50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Pro Glu Lys
                85                  90                  95

<210> SEQ ID NO 9
<211> LENGTH: 96
<212> TYPE: PRT
<213> ORGANISM: Homo Sapiens

<400> SEQUENCE: 9

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Gln Leu Asp Lys Lys His His Asp Ala Glu Phe
        35                  40                  45

Thr Val Pro Gly Ser Lys Ser Thr Ala Thr Ile Thr Arg Leu Lys Arg
    50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Ser Pro Glu Arg
                85                  90                  95

<210> SEQ ID NO 10
```

<211> LENGTH: 96
<212> TYPE: PRT
<213> ORGANISM: Homo Sapiens

<400> SEQUENCE: 10

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Lys Thr Gly His Lys Ser Ser Asp His Glu Phe
        35                  40                  45

Thr Val Pro Gly Ser Lys Ser Thr Ala Thr Ile Gly Gly Met Lys Gly
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Phe Glu Arg
                85                  90                  95

<210> SEQ ID NO 11
<211> LENGTH: 96
<212> TYPE: PRT
<213> ORGANISM: Homo Sapiens

<400> SEQUENCE: 11

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Lys Lys Asp Arg Ala Ser His Leu Lys Glu Phe
        35                  40                  45

Thr Val Pro Gly Ser Lys Ser Thr Ala Thr Ile Gly His Ile Lys Gly
    50                  55                  60

Gly Tyr Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Ser Gly Glu Pro
                85                  90                  95

<210> SEQ ID NO 12
<211> LENGTH: 96
<212> TYPE: PRT
<213> ORGANISM: Homo Sapiens

<400> SEQUENCE: 12

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Arg Thr Lys Gly Lys Ser Lys Leu Lys Glu Phe
        35                  40                  45

Thr Val Pro Gly Ser Lys Ser Thr Ala Thr Ile Pro Gly Leu Lys Gln
    50                  55                  60

Gly Glu Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Met Phe Glu Arg
                85                  90                  95

<210> SEQ ID NO 13
<211> LENGTH: 96

<212> TYPE: PRT
<213> ORGANISM: Homo Sapiens

<400> SEQUENCE: 13

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Thr Ser Val Asp Asp Arg Lys Leu Arg Glu Phe
            35                  40                  45

Thr Val Pro Gly Ser Lys Ser Thr Ala Thr Ile Ser Arg Leu Lys Arg
        50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Ala Glu Asn
                85                  90                  95

<210> SEQ ID NO 14
<211> LENGTH: 96
<212> TYPE: PRT
<213> ORGANISM: Homo Sapiens

<400> SEQUENCE: 14

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Val Leu Ser Thr Lys His Leu Lys Glu Phe
            35                  40                  45

Thr Val Pro Gly Ser Lys Ser Thr Ala Thr Ile Ser Gly Leu Lys Leu
        50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Met Glu Ser
                85                  90                  95

<210> SEQ ID NO 15
<211> LENGTH: 96
<212> TYPE: PRT
<213> ORGANISM: Homo Sapiens

<400> SEQUENCE: 15

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Ser Arg Ala Ser His Arg Lys Leu Thr Glu Phe
            35                  40                  45

Thr Val Pro Gly Ser Lys Ser Thr Ala Thr Ile Ser Gly Leu Lys Thr
        50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu His
                85                  90                  95

<210> SEQ ID NO 16
<211> LENGTH: 96
<212> TYPE: PRT

<213> ORGANISM: Homo Sapiens

<400> SEQUENCE: 16

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Ile Thr Gly Lys Glu Lys Ser Phe Val Glu Phe
        35                  40                  45

Thr Val Pro Gly Ser Lys Ser Thr Ala Thr Ile Arg Asp Val Lys Lys
    50                  55                  60

Gly Lys Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Ala Glu Thr
                85                  90                  95

<210> SEQ ID NO 17
<211> LENGTH: 96
<212> TYPE: PRT
<213> ORGANISM: Homo Sapiens

<400> SEQUENCE: 17

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Gln Arg Val Gly Lys Thr Lys Val His Glu Phe
        35                  40                  45

Thr Val Pro Gly Ser Lys Ser Thr Ala Thr Ile Arg Gly Leu Lys Arg
    50                  55                  60

Gly Lys Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Phe Pro Glu Thr
                85                  90                  95

<210> SEQ ID NO 18
<211> LENGTH: 96
<212> TYPE: PRT
<213> ORGANISM: Homo Sapiens

<400> SEQUENCE: 18

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly His Thr Ala Lys Thr Arg His His His Glu Phe
        35                  40                  45

Thr Val Pro Gly Ser Lys Ser Thr Ala Thr Ile Cys Lys Ser Arg Arg
    50                  55                  60

Gly Ser Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Gln Ala Glu Thr
                85                  90                  95

<210> SEQ ID NO 19
<211> LENGTH: 96
<212> TYPE: PRT
<213> ORGANISM: Homo Sapiens

<400> SEQUENCE: 19

| Val | Ser | Asp | Val | Pro | Arg | Asp | Leu | Glu | Val | Val | Ala | Ala | Thr | Pro | Thr |
|---|---|---|---|---|---|---|---|---|---|---|---|---|---|---|---|
| 1 | | | | 5 | | | | | 10 | | | | | 15 | |

| Ser | Leu | Leu | Ile | Ser | Trp | Asp | Ala | Pro | Ala | Val | Thr | Val | Arg | Tyr | Tyr |
|---|---|---|---|---|---|---|---|---|---|---|---|---|---|---|---|
| | | | | 20 | | | | | 25 | | | | | 30 | |

| Arg | Ile | Thr | Tyr | Gly | Tyr | Gly | Ala | Ala | Asn | Arg | Arg | Ala | His | Glu | Phe |
|---|---|---|---|---|---|---|---|---|---|---|---|---|---|---|---|
| | | | 35 | | | | | 40 | | | | | 45 | | |

| Thr | Val | Pro | Gly | Ser | Lys | Ser | Thr | Ala | Thr | Ile | Ser | Gly | Leu | Lys | Arg |
|---|---|---|---|---|---|---|---|---|---|---|---|---|---|---|---|
| | 50 | | | | | 55 | | | | | 60 | | | | |

| Gly | Arg | Asp | Tyr | Thr | Ile | Thr | Val | Tyr | Ala | Val | Thr | Gly | Arg | Gly | Asp |
|---|---|---|---|---|---|---|---|---|---|---|---|---|---|---|---|
| 65 | | | | | 70 | | | | | 75 | | | | | 80 |

| Ser | Pro | Ala | Ser | Ser | Lys | Pro | Ile | Ser | Ile | Asn | Tyr | Arg | His | Glu | Leu |
|---|---|---|---|---|---|---|---|---|---|---|---|---|---|---|---|
| | | | | 85 | | | | | 90 | | | | | 95 | |

<210> SEQ ID NO 20
<211> LENGTH: 96
<212> TYPE: PRT
<213> ORGANISM: Homo Sapiens

<400> SEQUENCE: 20

| Val | Ser | Asp | Val | Pro | Arg | Asp | Leu | Glu | Val | Val | Ala | Ala | Thr | Pro | Thr |
|---|---|---|---|---|---|---|---|---|---|---|---|---|---|---|---|
| 1 | | | | 5 | | | | | 10 | | | | | 15 | |

| Ser | Leu | Leu | Ile | Ser | Trp | Asp | Ala | Pro | Ala | Val | Thr | Val | Arg | Tyr | Tyr |
|---|---|---|---|---|---|---|---|---|---|---|---|---|---|---|---|
| | | | | 20 | | | | | 25 | | | | | 30 | |

| Arg | Ile | Thr | Tyr | Gly | Lys | Leu | Gly | Gly | Lys | Pro | Lys | Val | Arg | Glu | Phe |
|---|---|---|---|---|---|---|---|---|---|---|---|---|---|---|---|
| | | | 35 | | | | | 40 | | | | | 45 | | |

| Thr | Val | Pro | Gly | Ser | Lys | Ser | Thr | Ala | Thr | Ile | Leu | Gly | Leu | Lys | Pro |
|---|---|---|---|---|---|---|---|---|---|---|---|---|---|---|---|
| | 50 | | | | | 55 | | | | | 60 | | | | |

| Gly | Leu | Asp | Tyr | Thr | Ile | Thr | Val | Tyr | Ala | Val | Thr | Gly | Arg | Gly | Asp |
|---|---|---|---|---|---|---|---|---|---|---|---|---|---|---|---|
| 65 | | | | | 70 | | | | | 75 | | | | | 80 |

| Ser | Pro | Ala | Ser | Ser | Lys | Pro | Ile | Ser | Ile | Asn | Tyr | Ile | His | Glu | Gln |
|---|---|---|---|---|---|---|---|---|---|---|---|---|---|---|---|
| | | | | 85 | | | | | 90 | | | | | 95 | |

<210> SEQ ID NO 21
<211> LENGTH: 96
<212> TYPE: PRT
<213> ORGANISM: Homo Sapiens

<400> SEQUENCE: 21

| Val | Ser | Asp | Val | Pro | Arg | Asp | Leu | Glu | Val | Val | Ala | Ala | Thr | Pro | Thr |
|---|---|---|---|---|---|---|---|---|---|---|---|---|---|---|---|
| 1 | | | | 5 | | | | | 10 | | | | | 15 | |

| Ser | Leu | Leu | Ile | Ser | Trp | Asp | Ala | Pro | Ala | Val | Thr | Val | Arg | Tyr | Tyr |
|---|---|---|---|---|---|---|---|---|---|---|---|---|---|---|---|
| | | | | 20 | | | | | 25 | | | | | 30 | |

| Arg | Ile | Thr | Tyr | Gly | Asp | Ser | Arg | His | His | Pro | Arg | Ala | His | Glu | Phe |
|---|---|---|---|---|---|---|---|---|---|---|---|---|---|---|---|
| | | | 35 | | | | | 40 | | | | | 45 | | |

| Thr | Val | Pro | Gly | Ser | Lys | Ser | Thr | Ala | Thr | Ile | Thr | Gly | Cys | Lys | Arg |
|---|---|---|---|---|---|---|---|---|---|---|---|---|---|---|---|
| | 50 | | | | | 55 | | | | | 60 | | | | |

| Gly | His | Asp | Tyr | Thr | Ile | Thr | Val | Tyr | Ala | Val | Thr | Gly | Arg | Gly | Asp |
|---|---|---|---|---|---|---|---|---|---|---|---|---|---|---|---|
| 65 | | | | | 70 | | | | | 75 | | | | | 80 |

| Ser | Pro | Ala | Ser | Ser | Lys | Pro | Ile | Ser | Ile | Asn | Tyr | Arg | Tyr | Glu | His |
|---|---|---|---|---|---|---|---|---|---|---|---|---|---|---|---|
| | | | | 85 | | | | | 90 | | | | | 95 | |

<210> SEQ ID NO 22
<211> LENGTH: 96
<212> TYPE: PRT
<213> ORGANISM: Homo Sapiens -continued

```
<400> SEQUENCE: 22

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Lys Ser His Gly His Arg Gln Lys His Glu Phe
        35                  40                  45

Thr Val Pro Gly Ser Lys Ser Thr Ala Thr Ile Ser Asp Tyr Arg Gln
    50                  55                  60

Gly Gly Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Lys Gly Glu Leu
                85                  90                  95

<210> SEQ ID NO 23
<211> LENGTH: 96
<212> TYPE: PRT
<213> ORGANISM: Homo Sapiens

<400> SEQUENCE: 23

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Val Met Gly Asp Thr Lys Lys Val Lys Glu Phe
        35                  40                  45

Thr Val Pro Gly Ser Lys Ser Thr Ala Thr Ile Glu Arg Ile Lys Leu
    50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Lys Glu His
                85                  90                  95

<210> SEQ ID NO 24
<211> LENGTH: 96
<212> TYPE: PRT
<213> ORGANISM: Homo Sapiens

<400> SEQUENCE: 24

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Ala Ser Lys Asn His Arg Gln His Glu Phe
        35                  40                  45

Thr Val Pro Gly Ser Lys Ser Thr Ala Thr Ile Ser Arg Ile Lys Arg
    50                  55                  60

Gly Thr Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Ser Pro Glu Ser
                85                  90                  95

<210> SEQ ID NO 25
<211> LENGTH: 96
<212> TYPE: PRT
<213> ORGANISM: Homo Sapiens

<400> SEQUENCE: 25
```

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Lys Pro Arg Lys Tyr Arg Ser Ser Glu Phe
                35                  40                  45

Thr Val Pro Gly Ser Lys Ser Thr Ala Thr Ile Arg His Ser Lys His
            50                  55                  60

Gly Lys Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Met Arg Glu Ile
                85                  90                  95
```

<210> SEQ ID NO 26
<211> LENGTH: 96
<212> TYPE: PRT
<213> ORGANISM: Homo Sapiens

<400> SEQUENCE: 26

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Lys Thr Ala Arg Lys Tyr His Met Gln Glu Phe
                35                  40                  45

Thr Val Pro Gly Ser Lys Ser Thr Ala Thr Ile Ser Gly Ile Lys Arg
            50                  55                  60

Gly Thr Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Asn Ser Glu His
                85                  90                  95
```

<210> SEQ ID NO 27
<211> LENGTH: 96
<212> TYPE: PRT
<213> ORGANISM: Homo Sapiens

<400> SEQUENCE: 27

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Leu Thr Lys Arg Lys Ser Leu Ile Ser Glu Phe
                35                  40                  45

Thr Val Pro Gly Ser Lys Ser Thr Ala Thr Ile Ile Gly Leu Lys Ala
            50                  55                  60

Gly Lys Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Lys Thr Glu Asn
                85                  90                  95
```

<210> SEQ ID NO 28
<211> LENGTH: 96
<212> TYPE: PRT
<213> ORGANISM: Homo Sapiens

<400> SEQUENCE: 28

Val Ser Asp Val Pro Arg Asp Leu Glu Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Lys Val Lys Ala Lys Pro Leu Val Glu Phe
            35                  40                  45

Thr Val Pro Gly Ser Lys Ser Thr Ala Thr Ile Ser Ser Leu Lys Thr
    50                  55                  60

Gly Lys Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Tyr Glu Gly
                85                  90                  95

<210> SEQ ID NO 29
<211> LENGTH: 96
<212> TYPE: PRT
<213> ORGANISM: Homo Sapiens

<400> SEQUENCE: 29

Val Ser Asp Val Pro Arg Asp Leu Glu Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Asp Arg Ala Lys Asn Thr Arg Ile Lys Glu Phe
            35                  40                  45

Thr Val Pro Gly Ser Lys Ser Thr Ala Thr Ile Ser Gly Leu Lys Arg
    50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Leu Glu Gly
                85                  90                  95

<210> SEQ ID NO 30
<211> LENGTH: 96
<212> TYPE: PRT
<213> ORGANISM: Homo Sapiens

<400> SEQUENCE: 30

Val Ser Asp Val Pro Arg Asp Leu Glu Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Ile Pro Ala Lys Lys His His Thr His Glu Phe
            35                  40                  45

Thr Val Pro Gly Ser Lys Ser Thr Ala Thr Ile Thr Gly Leu Lys Ser
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Thr
                85                  90                  95

<210> SEQ ID NO 31
<211> LENGTH: 96
<212> TYPE: PRT
<213> ORGANISM: Homo Sapiens

<400> SEQUENCE: 31

Val Ser Asp Val Pro Arg Asp Leu Glu Val Ala Ala Thr Pro Thr

```
                1               5                   10                  15
Ser Leu Leu Ile Ser Trp Asp Ala Pro Ala Val Thr Val Arg Tyr Tyr
                20                  25                  30

Arg Ile Thr Tyr Gly Glu Val His Gly His Thr Ala His Glu Phe
            35                  40                  45

Thr Val Pro Gly Ser Lys Ser Thr Ala Thr Ile Val Arg Leu Lys Arg
        50                  55                  60

Gly Lys Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Cys Pro Glu Arg
                85                  90                  95

<210> SEQ ID NO 32
<211> LENGTH: 96
<212> TYPE: PRT
<213> ORGANISM: Homo Sapiens

<400> SEQUENCE: 32

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Met Ile Ser Gly Asp Lys Arg Arg Glu Phe
            35                  40                  45

Thr Val Pro Gly Ser Lys Ser Thr Ala Thr Ile Asp Arg Leu Lys Leu
        50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Leu Glu Ser
                85                  90                  95

<210> SEQ ID NO 33
<211> LENGTH: 96
<212> TYPE: PRT
<213> ORGANISM: Homo Sapiens

<400> SEQUENCE: 33

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Val Met His Asp Lys His Pro Lys Lys Glu Phe
            35                  40                  45

Thr Val Pro Gly Ser Lys Ser Thr Ala Thr Ile Ser Gly Leu Lys Arg
        50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Lys Ser Glu Ala
                85                  90                  95

<210> SEQ ID NO 34
<211> LENGTH: 96
<212> TYPE: PRT
<213> ORGANISM: Homo Sapiens

<400> SEQUENCE: 34

Val Ser Asp Val Pro Arg Asp Leu Glu Val Val Ala Ala Thr Pro Thr
1               5                   10                  15
```

```
Ser Leu Leu Ile Thr Trp Asp Ala Pro Ala Val Thr Val Arg Tyr Tyr
            20                  25                  30

Arg Ile Thr Tyr Gly Val Ala Gly Lys Thr Lys Pro Arg Ser Glu Phe
            35                  40                  45

Thr Val Pro Gly Ser Lys Ser Thr Ala Thr Ile Pro His Leu Lys Leu
        50                  55                  60

Gly His Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Ala Glu His
                85                  90                  95

<210> SEQ ID NO 35
<211> LENGTH: 96
<212> TYPE: PRT
<213> ORGANISM: Homo Sapiens

<400> SEQUENCE: 35

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Lys Asn Gly Arg His Asn Leu Asp His Glu Phe
            35                  40                  45

Thr Val Pro Gly Ser Lys Ser Thr Ala Thr Ile Ser Gly Leu Lys Arg
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr His Asn Glu Asn
                85                  90                  95

<210> SEQ ID NO 36
<211> LENGTH: 96
<212> TYPE: PRT
<213> ORGANISM: Homo Sapiens

<400> SEQUENCE: 36

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Asn Ile Val Ala Ala Asn Ala Leu Pro Glu Phe
            35                  40                  45

Thr Val Pro Gly Ser Lys Ser Thr Ala Thr Ile Thr Gly Leu Met Ser
        50                  55                  60

Gly Ile Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Ser Thr Glu Tyr
                85                  90                  95

<210> SEQ ID NO 37
<211> LENGTH: 96
<212> TYPE: PRT
<213> ORGANISM: Homo Sapiens

<400> SEQUENCE: 37

Val Ser Asp Val Pro Arg Asp Leu Glu Val Val Ala Ala Thr Pro Thr
1               5                   10                  15
```

```
Ser Leu Leu Ile Ser Trp Asp Ala Pro Ala Val Thr Val Arg Tyr Tyr
                20                  25                  30

Arg Ile Thr Tyr Gly Lys Leu Ser Gln Pro Thr Lys Arg Arg Glu Phe
            35                  40                  45

Thr Val Pro Gly Ser Lys Ser Thr Ala Thr Ile Ser Arg Leu Lys Pro
        50                  55                  60

Gly Leu Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr His Tyr Glu Leu
                85                  90                  95
```

<210> SEQ ID NO 38
<211> LENGTH: 96
<212> TYPE: PRT
<213> ORGANISM: Homo Sapiens

<400> SEQUENCE: 38

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Lys Ser Ser His Asn Ser Ala Ala Lys Glu Phe
            35                  40                  45

Thr Val Pro Gly Ser Lys Ser Thr Ala Thr Ile Thr Arg Leu Lys Ser
        50                  55                  60

Gly Thr Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Lys Pro Glu Tyr
                85                  90                  95
```

<210> SEQ ID NO 39
<211> LENGTH: 96
<212> TYPE: PRT
<213> ORGANISM: Homo Sapiens

<400> SEQUENCE: 39

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Lys Lys His Lys His Thr Thr Val Arg Glu Phe
            35                  40                  45

Thr Val Pro Gly Ser Lys Ser Thr Ala Thr Ile Ala Gly Lys Ser Leu
        50                  55                  60

Gly Gly Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Thr Ser Glu Thr
                85                  90                  95
```

<210> SEQ ID NO 40
<211> LENGTH: 96
<212> TYPE: PRT
<213> ORGANISM: Homo Sapiens

<400> SEQUENCE: 40

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
```

```
                    20                  25                  30

Arg Ile Thr Tyr Gly Arg Pro Gly His Asn Ser Lys Val His Glu Phe
                35                  40                  45

Thr Val Pro Gly Ser Lys Ser Thr Ala Thr Ile Asp Gly Ala Lys Lys
            50                  55                  60

Gly His Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Ile Met Glu His
                85                  90                  95

<210> SEQ ID NO 41
<211> LENGTH: 96
<212> TYPE: PRT
<213> ORGANISM: Homo Sapiens

<400> SEQUENCE: 41

Val Ser Asn Ile Pro Lys Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Gln Thr Met Asn Gly Gln Ser Asn Val Glu Phe
                35                  40                  45

Thr Val Pro Gly Ser Lys Ser Thr Ala Thr Ile Ser Pro Ser Lys Leu
            50                  55                  60

Gly Leu Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Leu Ser Glu Thr
                85                  90                  95

<210> SEQ ID NO 42
<211> LENGTH: 96
<212> TYPE: PRT
<213> ORGANISM: Homo Sapiens

<400> SEQUENCE: 42

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Lys Thr Gly Gly Lys Ser Lys Val His Glu Phe
                35                  40                  45

Thr Val Pro Gly Ser Lys Ser Thr Ala Thr Ile Ser Gly Leu Lys Arg
            50                  55                  60

Gly Arg Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Pro Glu His
                85                  90                  95

<210> SEQ ID NO 43
<211> LENGTH: 96
<212> TYPE: PRT
<213> ORGANISM: Homo Sapiens

<400> SEQUENCE: 43

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30
```

```
Arg Ile Thr Tyr Gly Glu Glu Ala Tyr Arg Ser Gly Gln Glu Phe
            35                  40                  45

Thr Val Pro Gly Ser Lys Ser Thr Ala Thr Ile Ser Ser Tyr Gly Gln
 50                  55                  60

Gly Val Asp Tyr Thr Ile Thr Val Tyr Ala Val Thr Gly Arg Gly Glu
 65                  70                  75                  80

Ser Pro Ala Ser Ser Lys Pro Ile Ser Ile Asn Tyr Glu Gly Ser Glu
                 85                  90                  95
```

<210> SEQ ID NO 44
<211> LENGTH: 95
<212> TYPE: PRT
<213> ORGANISM: Homo Sapiens

<400> SEQUENCE: 44

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Ser Ser Leu Gly Ser Glu Gln Glu Phe Thr
            35                  40                  45

Val Pro Gly Ser Lys Ser Thr Ala Thr Ile Ser Glu Tyr Ala Pro Tyr
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Tyr Gly Pro Gly
                 85                  90                  95
```

<210> SEQ ID NO 45
<211> LENGTH: 95
<212> TYPE: PRT
<213> ORGANISM: Homo Sapiens

<400> SEQUENCE: 45

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Gln Ala Gln Glu Gly Gly Gln Glu Phe Thr
            35                  40                  45

Val Pro Asp Ser Lys Ser Thr Ala Thr Ile Ser Ala His Arg Ser Tyr
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Tyr Tyr Gly Glu
                 85                  90                  95
```

<210> SEQ ID NO 46
<211> LENGTH: 97
<212> TYPE: PRT
<213> ORGANISM: Homo Sapiens

<400> SEQUENCE: 46

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30
```

```
Arg Ile Thr Tyr Gly Glu Tyr Arg Ser Tyr Arg Ser Glu Arg Gln Glu
             35                  40                  45

Phe Thr Val Pro Gly Ser Lys Ser Thr Ala Thr Ile Ser Arg Gly Tyr
     50                  55                  60

Arg Ala Val Asp Tyr Thr Ile Thr Val Tyr Ala Val Thr Gly Arg Gly
 65                  70                  75                  80

Glu Ser Pro Ala Ser Ser Lys Pro Ile Ser Ile Asn Tyr Ser Tyr Arg
                 85                  90                  95

Tyr
```

<210> SEQ ID NO 47
<211> LENGTH: 97
<212> TYPE: PRT
<213> ORGANISM: Homo Sapiens

<400> SEQUENCE: 47

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Glu Arg Gly Tyr Glu Arg Ser Arg Gln Glu
             35                  40                  45

Phe Thr Val Pro Gly Ser Lys Ser Thr Ala Thr Ile Ser Glu Ser Tyr
     50                  55                  60

Arg Tyr Val Asp Tyr Thr Ile Thr Val Tyr Ala Val Thr Gly Arg Gly
 65                  70                  75                  80

Glu Ser Pro Ala Ser Ser Lys Pro Ile Ser Ile Asn Tyr Pro His Ser
                 85                  90                  95

Tyr
```

<210> SEQ ID NO 48
<211> LENGTH: 96
<212> TYPE: PRT
<213> ORGANISM: Homo Sapiens

<400> SEQUENCE: 48

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Gln Ser Gly Leu Ser Glu His Gln Glu Phe
             35                  40                  45

Thr Val Pro Gly Ser Lys Ser Thr Ala Thr Ile Ser Ser Leu Arg Tyr
     50                  55                  60

Tyr Val Asp Tyr Thr Ile Thr Val Tyr Ala Val Thr Gly Arg Gly Glu
 65                  70                  75                  80

Ser Pro Ala Ser Ser Lys Pro Ile Ser Ile Asn Tyr Ala Tyr Glu Tyr
                 85                  90                  95
```

<210> SEQ ID NO 49
<211> LENGTH: 96
<212> TYPE: PRT
<213> ORGANISM: Homo Sapiens

<400> SEQUENCE: 49

```
Val Ser Asp Val Pro Arg Asp Leu Glu Val Val Ala Ala Thr Pro Thr
 1               5                  10                  15
```

Ser Leu Leu Ile Ser Trp Asp Ala Pro Ala Val Thr Val Arg Tyr Tyr
            20                  25                  30

Arg Ile Thr Tyr Gly Glu Arg Gly Ser Glu Ala Glu Arg Gln Glu Phe
        35                  40                  45

Thr Val Pro Gly Ser Lys Ser Thr Ala Thr Ile Ser Gln Ala Tyr Tyr
 50                  55                  60

Gly Val Asp Tyr Thr Ile Thr Val Tyr Ala Val Thr Gly Arg Gly Glu
 65                  70                  75                  80

Ser Pro Ala Ser Ser Lys Pro Ile Ser Ile Asn Tyr Ser Tyr Ala Ser
                85                  90                  95

<210> SEQ ID NO 50
<211> LENGTH: 94
<212> TYPE: PRT
<213> ORGANISM: Homo Sapiens

<400> SEQUENCE: 50

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30

Arg Ile Thr Tyr Gly Glu Ser Leu Tyr Tyr His Gln Glu Phe Thr Val
        35                  40                  45

Pro Gly Ser Lys Ser Thr Ala Thr Ile Ser Ala Ser Tyr Tyr Ala Val
 50                  55                  60

Asp Tyr Thr Ile Thr Val Tyr Ala Val Thr Gly Arg Gly Glu Ser Pro
 65                  70                  75                  80

Ala Ser Ser Lys Pro Ile Ser Ile Asn Tyr Ser Tyr His Leu
                85                  90

<210> SEQ ID NO 51
<211> LENGTH: 97
<212> TYPE: PRT
<213> ORGANISM: Homo Sapiens

<400> SEQUENCE: 51

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30

Arg Ile Thr Tyr Gly Glu Ser Tyr Arg Arg Gly Gln Ser Gly Gln Glu
        35                  40                  45

Phe Thr Val Pro Gly Ser Lys Ser Thr Ala Thr Ile Ser Pro Ser Gln
 50                  55                  60

Ser Gly Val Asp Tyr Thr Ile Thr Val Tyr Ala Val Thr Gly Arg Gly
 65                  70                  75                  80

Glu Ser Pro Ala Ser Ser Lys Pro Ile Ser Ile Asn Tyr Ser Tyr Ala
                85                  90                  95

Ser

<210> SEQ ID NO 52
<211> LENGTH: 96
<212> TYPE: PRT
<213> ORGANISM: Homo Sapiens

<400> SEQUENCE: 52

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
            20                  25                  30

Arg Ile Thr Tyr Gly Glu Ser Arg Ser Pro Arg Gly Gln Glu Phe
        35                  40                  45

Thr Val Pro Gly Ser Lys Ser Thr Ala Thr Ile Ser Arg Ala Glu Tyr
    50                  55                  60

Arg Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Tyr Leu Arg Gln
                85                  90                  95

<210> SEQ ID NO 53
<211> LENGTH: 96
<212> TYPE: PRT
<213> ORGANISM: Homo Sapiens

<400> SEQUENCE: 53

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Ser Ser Pro Glu Tyr Arg Gly Gln Glu Phe
        35                  40                  45

Thr Val Pro Gly Ser Lys Ser Thr Ala Thr Ile Ser Leu Glu Glu Tyr
    50                  55                  60

Glu Val Asp Tyr Thr Ile Thr Val Tyr Ala Val Thr Gly Arg Gly Glu
65                  70                  75                  80

Ser Pro Thr Ser Ser Lys Pro Ile Ser Ile Asn Tyr Gln Tyr Arg Tyr
                85                  90                  95

<210> SEQ ID NO 54
<211> LENGTH: 96
<212> TYPE: PRT
<213> ORGANISM: Homo Sapiens

<400> SEQUENCE: 54

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Ser Leu Arg Ser Arg Glu Gly Gln Glu Phe
        35                  40                  45

Thr Val Pro Gly Ser Lys Ser Thr Ala Thr Ile Ser Gly Arg Gln Glu
    50                  55                  60

Ser Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Gly Gln Arg Tyr
                85                  90                  95

<210> SEQ ID NO 55
<211> LENGTH: 96
<212> TYPE: PRT
<213> ORGANISM: Homo Sapiens

<400> SEQUENCE: 55

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Gly Gln Ala Gly Ala Ser Gln Glu Phe
        35                  40                  45

Thr Val Pro Gly Ser Lys Ser Thr Ala Thr Ile Ser Gly Ala Glu Pro
    50                  55                  60

Ala Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Gly Pro Arg Tyr
                85                  90                  95

<210> SEQ ID NO 56
<211> LENGTH: 95
<212> TYPE: PRT
<213> ORGANISM: Homo Sapiens

<400> SEQUENCE: 56

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Tyr Leu Tyr His His Gly Gln Glu Phe Thr
        35                  40                  45

Val Pro Gly Ser Lys Ser Thr Ala Thr Ile Ser Tyr Arg Ser Ala Pro
    50                  55                  60

Val Asp Tyr Thr Ile Thr Val Tyr Ala Val Thr Gly Arg Gly Glu Ser
65                  70                  75                  80

Pro Ala Ser Ser Lys Pro Ile Ser Ile Asn Tyr Arg His Glu Arg
                85                  90                  95

<210> SEQ ID NO 57
<211> LENGTH: 96
<212> TYPE: PRT
<213> ORGANISM: Homo Sapiens

<400> SEQUENCE: 57

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Gly Ser Leu Leu Tyr His Ser Gln Glu Phe
        35                  40                  45

Thr Val Pro Gly Ser Lys Ser Thr Ala Thr Ile Ser Tyr Gly Pro Ala
    50                  55                  60

Ser Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Arg Arg Tyr
                85                  90                  95

<210> SEQ ID NO 58
<211> LENGTH: 95
<212> TYPE: PRT
<213> ORGANISM: Homo Sapiens

<400> SEQUENCE: 58

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr

-continued

```
            20                  25                  30
Arg Ile Thr Tyr Gly Glu Ser Ser His Gly Arg Ser Gln Glu Phe Thr
            35                  40                  45
Val Pro Gly Ser Lys Ser Thr Ala Thr Ile Ser Ser Ser Ser Ser Arg
 50                  55                  60
Val Asp Tyr Thr Ile Thr Val Tyr Ala Val Thr Gly Arg Gly Glu Ser
 65                  70                  75                  80
Pro Ala Ser Ser Lys Pro Ile Ser Ile Asn Tyr Gly Tyr Arg Gly
                 85                  90                  95
```

<210> SEQ ID NO 59
<211> LENGTH: 95
<212> TYPE: PRT
<213> ORGANISM: Homo Sapiens

<400> SEQUENCE: 59

```
Val Ser Asp Val Pro Arg Asp Leu Glu Val Val Ala Ala Thr Pro Thr
 1                   5                  10                  15
Ser Leu Leu Ile Ser Trp Asp Ala Pro Ala Val Thr Val Arg Tyr Tyr
                 20                  25                  30
Arg Ile Thr Tyr Gly Glu Tyr Gly Tyr Ser Arg Ser Gln Glu Phe Thr
            35                  40                  45
Val Pro Gly Ser Lys Ser Thr Ala Thr Ile Ser Tyr Ser Ser Pro Arg
 50                  55                  60
Val Asp Tyr Thr Ile Thr Val Tyr Ala Val Thr Gly Arg Gly Glu Ser
 65                  70                  75                  80
Pro Ala Ser Ser Lys Pro Ile Ser Ile Asn Tyr Gly Ser Arg Tyr
                 85                  90                  95
```

<210> SEQ ID NO 60
<211> LENGTH: 97
<212> TYPE: PRT
<213> ORGANISM: Homo Sapiens

<400> SEQUENCE: 60

```
Val Ser Asp Val Pro Arg Asp Leu Glu Val Val Ala Ala Thr Pro Thr
 1                   5                  10                  15
Ser Leu Leu Ile Ser Trp Asp Ala Pro Ala Val Thr Val Arg Tyr Tyr
                 20                  25                  30
Arg Ile Thr Tyr Gly Glu Tyr Arg Tyr Ala Tyr Ala Tyr Gly Gln Glu
            35                  40                  45
Phe Thr Val Pro Gly Ser Lys Ser Thr Ala Thr Ile Ser Arg Ser Ser
 50                  55                  60
Pro Arg Val Asp Tyr Thr Ile Thr Val Tyr Ala Val Thr Gly Arg Gly
 65                  70                  75                  80
Glu Ser Pro Ala Ser Ser Lys Pro Ile Ser Ile Asn Tyr Pro Arg Arg
                 85                  90                  95
Tyr
```

<210> SEQ ID NO 61
<211> LENGTH: 96
<212> TYPE: PRT
<213> ORGANISM: Homo Sapiens

<400> SEQUENCE: 61

```
Val Ser Asp Val Pro Arg Asp Leu Glu Val Val Ala Ala Thr Pro Thr
 1                   5                  10                  15
```

```
Ser Leu Leu Ile Ser Trp Asp Ala Pro Ala Val Thr Val Arg Tyr Tyr
            20                  25                  30

Arg Ile Thr Tyr Gly Glu Pro Arg Ser Glu Glu Gly Glu Gln Glu Phe
        35                  40                  45

Thr Val Pro Gly Ser Lys Ser Thr Ala Thr Ile Ser Arg Arg Tyr Ser
    50                  55                  60

Leu Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Tyr Ser Ser Arg
                85                  90                  95
```

<210> SEQ ID NO 62
<211> LENGTH: 96
<212> TYPE: PRT
<213> ORGANISM: Homo Sapiens

<400> SEQUENCE: 62

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Ala Ala Ser Ser Arg Leu Arg Gln Glu Phe
        35                  40                  45

Thr Val Pro Gly Ser Lys Ser Thr Ala Thr Ile Ser Ser Tyr Ser Gly
    50                  55                  60

Leu Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Tyr Ser Ser Tyr
                85                  90                  95
```

<210> SEQ ID NO 63
<211> LENGTH: 96
<212> TYPE: PRT
<213> ORGANISM: Homo Sapiens

<400> SEQUENCE: 63

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Arg Glu Arg Gln His Gly Tyr Gln Glu Phe
        35                  40                  45

Thr Val Pro Gly Ser Lys Ser Thr Ala Thr Ile Ser Arg Tyr Arg Arg
    50                  55                  60

Arg Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Glu Pro Gly Tyr
                85                  90                  95
```

<210> SEQ ID NO 64
<211> LENGTH: 96
<212> TYPE: PRT
<213> ORGANISM: Homo Sapiens

<400> SEQUENCE: 64

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
```

```
                    20                  25                  30

Arg Ile Thr Tyr Gly Glu Arg Ser His Arg Glu Arg Gln Glu Phe
                35                  40                  45

Thr Val Pro Gly Ser Lys Ser Thr Ala Thr Ile Ser Arg Arg Arg
        50                  55                  60

Arg Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Ser Arg Arg Arg
                85                  90                  95

<210> SEQ ID NO 65
<211> LENGTH: 96
<212> TYPE: PRT
<213> ORGANISM: Homo Sapiens

<400> SEQUENCE: 65

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Arg Leu Arg Glu Gly Gly Ser Gln Glu Phe
                35                  40                  45

Thr Val Pro Gly Ser Lys Ser Thr Ala Thr Ile Ser Arg Ala Gly Glu
        50                  55                  60

Arg Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Ala Gln Tyr Pro
                85                  90                  95

<210> SEQ ID NO 66
<211> LENGTH: 95
<212> TYPE: PRT
<213> ORGANISM: Homo Sapiens

<400> SEQUENCE: 66

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Tyr Tyr Arg Ser Tyr Tyr Gln Glu Phe Thr
                35                  40                  45

Val Pro Gly Ser Lys Ser Thr Ala Thr Ile Ser Ser Tyr Glu Pro Pro
        50                  55                  60

Val Asp Tyr Thr Ile Thr Val Tyr Ala Val Thr Gly Arg Gly Glu Ser
65                  70                  75                  80

Pro Ala Ser Ser Lys Pro Ile Ser Ile Asn Tyr Arg Arg Tyr Leu
                85                  90                  95

<210> SEQ ID NO 67
<211> LENGTH: 96
<212> TYPE: PRT
<213> ORGANISM: Homo Sapiens

<400> SEQUENCE: 67

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30
```

Arg Ile Thr Tyr Gly Glu Tyr Tyr Ala Arg Pro Tyr Gln Glu Phe
                35                  40                  45

Thr Val Pro Gly Ser Lys Ser Thr Ala Thr Ile Ser Tyr Tyr Glu Pro
 50                  55                  60

Glu Val Asp Tyr Thr Ile Thr Val Tyr Ala Val Thr Gly Arg Gly Glu
 65                  70                  75                  80

Ser Pro Ala Ser Ser Lys Pro Ile Ser Ile Asn Tyr Arg Ser Tyr Pro
                 85                  90                  95

<210> SEQ ID NO 68
<211> LENGTH: 96
<212> TYPE: PRT
<213> ORGANISM: Homo Sapiens

<400> SEQUENCE: 68

Val Ser Asp Val Pro Arg Asp Leu Glu Val Val Ala Ala Thr Pro Thr
 1                5                  10                  15

Ser Leu Leu Ile Ser Trp Asp Ala Pro Ala Val Thr Val Arg Tyr Tyr
                20                  25                  30

Arg Ile Thr Tyr Gly Glu Tyr Tyr Arg Ser Ser Leu Pro Gln Glu Phe
                35                  40                  45

Thr Val Pro Gly Ser Lys Ser Thr Ala Thr Ile Ser Tyr Tyr Tyr Pro
 50                  55                  60

Ser Val Asp Tyr Thr Ile Thr Val Tyr Ala Val Thr Gly Arg Gly Glu
 65                  70                  75                  80

Ser Pro Ala Ser Ser Lys Pro Ile Ser Ile Asn Tyr Ser Arg Tyr Tyr
                 85                  90                  95

<210> SEQ ID NO 69
<211> LENGTH: 96
<212> TYPE: PRT
<213> ORGANISM: Homo Sapiens

<400> SEQUENCE: 69

Val Ser Asp Val Pro Arg Asp Leu Glu Val Val Ala Ala Thr Pro Thr
 1                5                  10                  15

Ser Leu Leu Ile Ser Trp Asp Ala Pro Ala Val Thr Val Arg Tyr Tyr
                20                  25                  30

Arg Ile Thr Tyr Gly Glu Tyr Arg Ser Ser Tyr Tyr Gln Glu Phe
                35                  40                  45

Thr Val Pro Gly Ser Lys Ser Thr Ala Thr Ile Ser Tyr Pro Ser Glu
 50                  55                  60

Arg Val Asp Tyr Thr Ile Thr Val Tyr Ala Val Thr Gly Arg Gly Glu
 65                  70                  75                  80

Ser Pro Ala Ser Ser Lys Pro Ile Ser Ile Asn Tyr Gln Ser Ser Ala
                 85                  90                  95

<210> SEQ ID NO 70
<211> LENGTH: 96
<212> TYPE: PRT
<213> ORGANISM: Homo Sapiens

<400> SEQUENCE: 70

Val Ser Asp Val Pro Arg Asp Leu Glu Val Val Ala Ala Thr Pro Thr
 1                5                  10                  15

Ser Leu Leu Ile Ser Trp Asp Ala Pro Ala Val Thr Val Arg Tyr Tyr
                20                  25                  30

Arg Ile Thr Tyr Gly Glu Ser His Gln Gly Leu Ser Tyr Gln Glu Phe
            35                  40                  45

Thr Val Pro Gly Ser Lys Ser Thr Ala Thr Ile Ser Pro Gly Ser Ser
    50                  55                  60

Ser Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Tyr Tyr Arg
                85                  90                  95

<210> SEQ ID NO 71
<211> LENGTH: 96
<212> TYPE: PRT
<213> ORGANISM: Homo Sapiens

<400> SEQUENCE: 71

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Arg Gly Ser Gly Leu Gly Tyr Gln Glu Phe
            35                  40                  45

Thr Val Pro Gly Ser Lys Ser Thr Ala Thr Ile Ser Ser Arg Ala Tyr
    50                  55                  60

Arg Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Ala Leu Tyr Glu
                85                  90                  95

<210> SEQ ID NO 72
<211> LENGTH: 95
<212> TYPE: PRT
<213> ORGANISM: Homo Sapiens

<400> SEQUENCE: 72

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Arg Gly Gly Tyr Ser Ser Gln Glu Phe Thr
            35                  40                  45

Val Pro Gly Ser Lys Ser Thr Ala Thr Ile Ser Ser Arg Tyr Arg Gln
    50                  55                  60

Val Asp Tyr Thr Ile Thr Val Tyr Ala Val Thr Gly Arg Gly Glu Ser
65                  70                  75                  80

Pro Ala Ser Ser Lys Pro Ile Ser Ile Asn Tyr Gln Ser Tyr Ser
                85                  90                  95

<210> SEQ ID NO 73
<211> LENGTH: 94
<212> TYPE: PRT
<213> ORGANISM: Homo Sapiens

<400> SEQUENCE: 73

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Arg Gly Tyr Pro Gly Gln Glu Phe Thr Val

```
                35                  40                  45
Pro Gly Ser Lys Ser Thr Ala Thr Ile Ser Glu Tyr Ser His Ser Val
     50                  55                  60

Asp Tyr Thr Ile Thr Val Tyr Ala Val Thr Gly Arg Gly Glu Ser Pro
 65                  70                  75                  80

Ala Ser Ser Lys Pro Ile Ser Ile Asn Tyr Ala Gln Tyr Gln
                 85                  90
```

<210> SEQ ID NO 74
<211> LENGTH: 97
<212> TYPE: PRT
<213> ORGANISM: Homo Sapiens

<400> SEQUENCE: 74

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Tyr Glu Pro Tyr Gly Ser Gln Tyr Gln Glu
                 35                  40                  45

Phe Thr Val Pro Gly Ser Lys Ser Thr Ala Thr Ile Ser Glu Arg Gln
 50                  55                  60

His Ala Val Asp Tyr Thr Ile Thr Val Tyr Ala Val Thr Gly Arg Gly
 65                  70                  75                  80

Glu Ser Pro Ala Ser Ser Lys Pro Ile Ser Ile Asn Tyr Arg Tyr Tyr
                 85                  90                  95

Glu
```

<210> SEQ ID NO 75
<211> LENGTH: 95
<212> TYPE: PRT
<213> ORGANISM: Homo Sapiens

<400> SEQUENCE: 75

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Tyr Gly Gly Ser Gln Ala Gln Glu Phe Thr
                 35                  40                  45

Val Pro Gly Ser Lys Ser Thr Ala Thr Ile Ser Arg Glu Tyr Gly Ser
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Ala Leu Gly Glu
                 85                  90                  95
```

<210> SEQ ID NO 76
<211> LENGTH: 95
<212> TYPE: PRT
<213> ORGANISM: Homo Sapiens

<400> SEQUENCE: 76

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30
```

Arg Ile Thr Tyr Gly Glu Ser Gly Arg Tyr Gln Glu Phe Thr
            35                  40                  45

Val Pro Gly Ser Lys Ser Thr Ala Thr Ile Ser Arg Tyr Pro His Gly
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Ala Lys Asn Val
                 85                  90                  95

<210> SEQ ID NO 77
<211> LENGTH: 95
<212> TYPE: PRT
<213> ORGANISM: Homo Sapiens

<400> SEQUENCE: 77

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Tyr Arg Arg Ala Arg Gln Glu Phe Thr
            35                  40                  45

Val Pro Gly Ser Lys Ser Thr Ala Thr Ile Ser Glu His Glu Pro Leu
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Tyr Ser Tyr Tyr
                 85                  90                  95

<210> SEQ ID NO 78
<211> LENGTH: 95
<212> TYPE: PRT
<213> ORGANISM: Homo Sapiens

<400> SEQUENCE: 78

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Gln Arg Ala Arg Ser Arg Gln Glu Phe Thr
            35                  40                  45

Val Pro Gly Ser Lys Ser Thr Ala Thr Ile Ser Glu Gln Arg Arg Arg
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Arg Ala Leu Leu
                 85                  90                  95

<210> SEQ ID NO 79
<211> LENGTH: 95
<212> TYPE: PRT
<213> ORGANISM: Homo Sapiens

<400> SEQUENCE: 79

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Arg Arg Arg Arg Tyr Gly Gln Glu Phe Thr

```
                35                  40                  45
Val Pro Gly Ser Lys Ser Thr Ala Thr Ile Ser Ser Arg Arg Gly
    50                  55                  60
Val Asp Tyr Thr Ile Thr Val Tyr Ala Val Thr Gly Arg Gly Glu Ser
65                  70                  75                  80
Pro Ala Ser Ser Lys Pro Ile Ser Ile Asn Tyr Leu Tyr Pro Tyr
                85                  90                  95

<210> SEQ ID NO 80
<211> LENGTH: 95
<212> TYPE: PRT
<213> ORGANISM: Homo Sapiens

<400> SEQUENCE: 80

Val Ser Asp Val Pro Arg Asp Leu Glu Val Val Ala Ala Thr Pro Thr
1               5                   10                  15
Ser Leu Leu Ile Ser Trp Asp Ala Pro Ala Val Thr Val Arg Tyr Tyr
                20                  25                  30
Arg Ile Thr Tyr Gly Glu Ser Arg Arg Ser Tyr Pro Gln Glu Phe Thr
                35                  40                  45
Val Pro Gly Ser Lys Ser Thr Ala Thr Ile Ser Ser His Arg Ser
    50                  55                  60
Val Asp Tyr Thr Ile Thr Val Tyr Ala Val Thr Gly Arg Gly Glu Ser
65                  70                  75                  80
Pro Ala Ser Ser Lys Pro Ile Ser Ile Asn Tyr Arg Ser Tyr Leu
                85                  90                  95

<210> SEQ ID NO 81
<211> LENGTH: 95
<212> TYPE: PRT
<213> ORGANISM: Homo Sapiens

<400> SEQUENCE: 81

Val Ser Asp Val Pro Arg Asp Leu Glu Val Val Ala Ala Thr Pro Thr
1               5                   10                  15
Ser Leu Leu Ile Ser Trp Asp Ala Pro Ala Val Thr Val Arg Tyr Tyr
                20                  25                  30
Arg Ile Thr Tyr Gly Glu Ser His His Tyr Gly Pro Gln Glu Phe Thr
                35                  40                  45
Val Pro Gly Ser Lys Ser Thr Ala Thr Ile Ser Leu Leu Gly Ala His
    50                  55                  60
Val Asp Tyr Thr Ile Thr Val Tyr Ala Val Thr Gly Arg Gly Glu Ser
65                  70                  75                  80
Pro Ala Ser Ser Lys Pro Ile Ser Ile Asn Tyr His Gly Leu Tyr
                85                  90                  95

<210> SEQ ID NO 82
<211> LENGTH: 95
<212> TYPE: PRT
<213> ORGANISM: Homo Sapiens

<400> SEQUENCE: 82

Val Ser Asp Val Pro Arg Asp Leu Glu Val Val Ala Ala Thr Pro Thr
1               5                   10                  15
Ser Leu Leu Ile Ser Trp Asp Ala Pro Ala Val Thr Val Arg Tyr Tyr
                20                  25                  30
Arg Ile Thr Tyr Gly Glu Ser His His Tyr Gly Pro Gln Glu Phe Thr
                35                  40                  45
```

Val Pro Gly Ser Lys Ser Thr Ala Thr Ile Ser Leu Leu Gly Ala His
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr His Gly Leu Tyr
                 85                  90                  95

<210> SEQ ID NO 83
<211> LENGTH: 95
<212> TYPE: PRT
<213> ORGANISM: Homo Sapiens

<400> SEQUENCE: 83

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Ala His Glu Tyr Tyr Gln Glu Phe Thr
             35                  40                  45

Val Pro Gly Ser Lys Ser Thr Ala Thr Ile Ser Arg Ser Ser Ser
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Tyr Gly Arg Tyr
                 85                  90                  95

<210> SEQ ID NO 84
<211> LENGTH: 95
<212> TYPE: PRT
<213> ORGANISM: Homo Sapiens

<400> SEQUENCE: 84

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Ala Gly Tyr Ser Gly Gly Gln Glu Phe Thr
             35                  40                  45

Val Pro Gly Ser Lys Ser Thr Ala Thr Ile Ser Glu Arg Ala Glu Tyr
 50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Glu Arg Arg Tyr
                 85                  90                  95

<210> SEQ ID NO 85
<211> LENGTH: 95
<212> TYPE: PRT
<213> ORGANISM: Homo Sapiens

<400> SEQUENCE: 85

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                 20                  25                  30

Arg Ile Thr Tyr Gly Glu Leu Ser Arg Ser Gly Ser Gln Glu Phe Thr
             35                  40                  45

Val Pro Gly Ser Lys Ser Thr Ala Thr Ile Ser Gly Ser Tyr Gly Tyr
            50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Glu Gln Ser Tyr
                 85                  90                  95

<210> SEQ ID NO 86
<211> LENGTH: 95
<212> TYPE: PRT
<213> ORGANISM: Homo Sapiens

<400> SEQUENCE: 86

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Leu Pro Ser Gln Gly Arg Gln Glu Phe Thr
             35                  40                  45

Val Pro Gly Ser Lys Ser Thr Ala Thr Ile Ser Tyr Arg Arg Glu Leu
            50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Gly Ser Ser Tyr
                 85                  90                  95

<210> SEQ ID NO 87
<211> LENGTH: 95
<212> TYPE: PRT
<213> ORGANISM: Homo Sapiens

<400> SEQUENCE: 87

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Ala Tyr Gly Glu Ser Tyr Gln Glu Phe Thr
             35                  40                  45

Val Pro Gly Ser Lys Ser Thr Ala Thr Ile Ser Gln Ser Pro Glu Tyr
            50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Ala Ser Glu Tyr
                 85                  90                  95

<210> SEQ ID NO 88
<211> LENGTH: 95
<212> TYPE: PRT
<213> ORGANISM: Homo Sapiens

<400> SEQUENCE: 88

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Ser Ser Ser Arg Arg Gln Glu Phe Thr
             35                  40                  45

Val Pro Gly Ser Lys Ser Thr Ala Thr Ile Ser Gly Glu Glu Ser Tyr

```
                    50                  55                  60
Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Ala Glu Glu Arg
                 85                  90                  95

<210> SEQ ID NO 89
<211> LENGTH: 95
<212> TYPE: PRT
<213> ORGANISM: Homo Sapiens

<400> SEQUENCE: 89

Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Gly Arg His Pro Ser Tyr Gln Glu Phe Thr
                 35                  40                  45

Val Pro Gly Ser Lys Ser Thr Ala Thr Ile Ser Pro Ser Tyr Ser Arg
             50                  55                  60

Val Asp Tyr Thr Ile Thr Val Tyr Ala Val Thr Gly Arg Gly Glu Ser
 65                  70                  75                  80

Pro Ala Ser Ser Lys Pro Ile Ser Ile Asn Tyr Ser Arg Glu Arg
                 85                  90                  95

<210> SEQ ID NO 90
<211> LENGTH: 94
<212> TYPE: PRT
<213> ORGANISM: Homo Sapiens

<400> SEQUENCE: 90

Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Gly Glu Arg Pro Tyr Gln Glu Phe Thr Val
                 35                  40                  45

Pro Gly Ser Lys Ser Thr Ala Thr Ile Ser Tyr Ala His Tyr Ser Val
             50                  55                  60

Asp Tyr Thr Ile Thr Val Tyr Ala Val Thr Gly Arg Gly Glu Ser Pro
 65                  70                  75                  80

Ala Ser Ser Lys Pro Ile Ser Asn Tyr Glu Arg Arg Ser
                 85                  90

<210> SEQ ID NO 91
<211> LENGTH: 94
<212> TYPE: PRT
<213> ORGANISM: Homo Sapiens

<400> SEQUENCE: 91

Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Tyr Gln Arg Ser Arg Gln Glu Phe Thr Val
                 35                  40                  45

Pro Gly Ser Lys Ser Thr Ala Thr Ile Ser Ser Tyr Gly Gly Tyr Val
             50                  55                  60
```

```
Asp Tyr Thr Ile Thr Val Tyr Ala Val Thr Gly Arg Gly Glu Ser Pro
 65                  70                  75                  80

Ala Ser Ser Lys Pro Ile Ser Ile Asn Tyr Arg Ser Leu Arg
                 85                  90
```

<210> SEQ ID NO 92
<211> LENGTH: 94
<212> TYPE: PRT
<213> ORGANISM: Homo Sapiens

<400> SEQUENCE: 92

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Tyr Glu Arg Tyr Arg Gln Glu Phe Thr Val
                 35                  40                  45

Pro Gly Ser Lys Ser Thr Ala Thr Ile Ser Ser Gln Ser Arg Tyr Val
 50                  55                  60

Asp Tyr Thr Ile Thr Val Tyr Ala Val Thr Gly Arg Gly Glu Ser Pro
 65                  70                  75                  80

Ala Ser Ser Lys Pro Ile Ser Ile Asn Tyr Gly Arg Pro Ala
                 85                  90
```

<210> SEQ ID NO 93
<211> LENGTH: 94
<212> TYPE: PRT
<213> ORGANISM: Homo Sapiens

<400> SEQUENCE: 93

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Tyr Pro Arg Glu Tyr Gln Glu Phe Thr Val
                 35                  40                  45

Pro Gly Ser Lys Ser Thr Ala Thr Ile Ser Arg Tyr Gly Tyr His Val
 50                  55                  60

Asp Tyr Thr Ile Thr Val Tyr Ala Val Thr Gly Arg Gly Glu Ser Pro
 65                  70                  75                  80

Ala Ser Ser Lys Pro Ile Ser Ile Asn Tyr Ser Gly Tyr Ser
                 85                  90
```

<210> SEQ ID NO 94
<211> LENGTH: 94
<212> TYPE: PRT
<213> ORGANISM: Homo Sapiens

<400> SEQUENCE: 94

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Tyr Tyr
                 20                  25                  30

Arg Ile Thr Tyr Gly Glu Tyr Glu His Tyr Tyr Gln Glu Phe Thr Val
                 35                  40                  45

Pro Gly Ser Lys Ser Thr Ala Thr Ile Ser Pro Tyr Ala Gly Gly Val
 50                  55                  60
```

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Ser Glu Ser Glu
                85                  90

<210> SEQ ID NO 95
<211> LENGTH: 94
<212> TYPE: PRT
<213> ORGANISM: Homo Sapiens

<400> SEQUENCE: 95

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Tyr Glu Tyr Ala Arg Gln Glu Phe Thr Val
                35                  40                  45

Pro Gly Ser Lys Ser Thr Ala Thr Ile Ser Arg Leu Tyr Arg Arg Val
50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Tyr Arg Ser Ala
                85                  90

<210> SEQ ID NO 96
<211> LENGTH: 94
<212> TYPE: PRT
<213> ORGANISM: Homo Sapiens

<400> SEQUENCE: 96

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Tyr His Tyr Ser Glu Gln Glu Phe Thr Val
                35                  40                  45

Pro Gly Ser Lys Ser Thr Ala Thr Ile Ser Tyr Tyr Gly Pro Arg Val
50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr His Ser Ser Arg
                85                  90

<210> SEQ ID NO 97
<211> LENGTH: 94
<212> TYPE: PRT
<213> ORGANISM: Homo Sapiens

<400> SEQUENCE: 97

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Gln Arg Tyr Leu Arg Gln Glu Phe Thr Val
                35                  40                  45

Pro Gly Ser Lys Ser Thr Ala Thr Ile Ser Ser Arg Ser Ala Arg Val
50                  55                  60

Asp Tyr Thr Ile Thr Val Tyr Ala Val Thr Gly Arg Gly Glu Ser Pro

```
                65                  70                  75                  80
Ala Ser Ser Lys Pro Ile Ser Ile Asn Tyr Pro Tyr Ser Ala
                85                  90
```

<210> SEQ ID NO 98
<211> LENGTH: 94
<212> TYPE: PRT
<213> ORGANISM: Homo Sapiens

<400> SEQUENCE: 98

```
Val Ser Asp Val Pro Arg Asp Leu Glu Val Val Ala Ala Thr Pro Thr
1               5                   10                  15
Ser Leu Leu Ile Ser Trp Asp Ala Pro Ala Val Thr Val Arg Tyr Tyr
                20                  25                  30
Arg Ile Thr Tyr Gly Glu Arg Ser Arg Ser Gln Glu Phe Thr Val
                35                  40                  45
Pro Gly Ser Lys Ser Thr Ala Thr Ile Ser His Ser Arg Glu Pro Val
        50                  55                  60
Asp Tyr Thr Ile Thr Val Tyr Ala Val Thr Gly Arg Gly Glu Ser Pro
65                  70                  75                  80
Ala Ser Ser Lys Pro Ile Ser Ile Asn Tyr Gln Tyr Arg Tyr
                85                  90
```

<210> SEQ ID NO 99
<211> LENGTH: 94
<212> TYPE: PRT
<213> ORGANISM: Homo Sapiens

<400> SEQUENCE: 99

```
Val Ser Asp Val Pro Arg Asp Leu Glu Val Val Ala Ala Thr Pro Thr
1               5                   10                  15
Ser Leu Leu Ile Ser Trp Asp Ala Pro Ala Val Thr Val Arg Tyr Tyr
                20                  25                  30
Arg Ile Thr Tyr Gly Glu Ser Gln Ser His Ser Gln Glu Phe Thr Val
                35                  40                  45
Pro Gly Ser Lys Ser Thr Ala Thr Ile Ser His Pro Ser Arg Pro Val
        50                  55                  60
Asp Tyr Thr Ile Thr Val Tyr Ala Val Thr Gly Arg Gly Glu Ser Pro
65                  70                  75                  80
Ala Ser Ser Lys Pro Ile Ser Ile Asn Tyr Pro Arg Ser Glu
                85                  90
```

<210> SEQ ID NO 100
<211> LENGTH: 94
<212> TYPE: PRT
<213> ORGANISM: Homo Sapiens

<400> SEQUENCE: 100

```
Val Ser Asp Val Pro Arg Asp Leu Glu Val Val Ala Ala Thr Pro Thr
1               5                   10                  15
Ser Leu Leu Ile Ser Trp Asp Ala Pro Ala Val Thr Val Arg Tyr Tyr
                20                  25                  30
Arg Ile Thr Tyr Gly Glu Glu Glu His Pro Gln Glu Phe Thr Val
                35                  40                  45
Pro Gly Ser Lys Ser Thr Ala Thr Ile Ser Ser Pro Gln Arg Gly Val
        50                  55                  60
Asp Tyr Thr Ile Thr Val Tyr Ala Val Thr Gly Arg Gly Glu Ser Pro
65                  70                  75                  80
```

```
Ala Ser Ser Lys Pro Ile Ser Ile Asn Tyr Tyr Ser Tyr Tyr
                85                  90
```

<210> SEQ ID NO 101
<211> LENGTH: 94
<212> TYPE: PRT
<213> ORGANISM: Homo Sapiens

<400> SEQUENCE: 101

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Glu Ser Ser Arg Pro Gln Glu Phe Thr Val
                35                  40                  45

Pro Gly Ser Lys Ser Thr Ala Thr Ile Ser Gln Ala Arg Ala Arg Val
             50                  55                  60

Asp Tyr Thr Ile Thr Val Tyr Ala Val Thr Gly Arg Gly Glu Ser Pro
 65                  70                  75                  80

Ala Ser Ser Lys Pro Ile Ser Ile Asn Tyr Arg Arg Tyr Arg
                85                  90
```

<210> SEQ ID NO 102
<211> LENGTH: 94
<212> TYPE: PRT
<213> ORGANISM: Homo Sapiens

<400> SEQUENCE: 102

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Tyr Gly Ala Leu Glu Gln Glu Phe Thr Val
                35                  40                  45

Pro Gly Ser Lys Ser Thr Ala Thr Ile Ser Arg Ser Gln Ala Glu Val
             50                  55                  60

Asp Tyr Thr Ile Thr Val Tyr Ala Val Thr Gly Arg Gly Glu Ser Pro
 65                  70                  75                  80

Ala Ser Ser Lys Pro Ile Ser Ile Asn Tyr Ala Ser Tyr Tyr
                85                  90
```

<210> SEQ ID NO 103
<211> LENGTH: 94
<212> TYPE: PRT
<213> ORGANISM: Homo Sapiens

<400> SEQUENCE: 103

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Ser Arg Glu Gly Gln Glu Phe Thr Val
                35                  40                  45

Pro Gly Ser Lys Ser Thr Ala Thr Ile Ser Ser Tyr Gln Ser Glu Val
             50                  55                  60

Asp Tyr Thr Ile Thr Val Tyr Ala Val Thr Gly Arg Gly Glu Ser Pro
 65                  70                  75                  80
```

```
Ala Ser Ser Lys Pro Ile Ser Ile Asn Tyr Ala Arg Ser Arg
            85                  90
```

<210> SEQ ID NO 104
<211> LENGTH: 94
<212> TYPE: PRT
<213> ORGANISM: Homo Sapiens

<400> SEQUENCE: 104

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Gly Gln Gln Gly Gln Glu Phe Thr Val
            35                  40                  45

Pro Gly Ser Lys Ser Thr Ala Thr Ile Ser Ala Tyr Arg Gly Pro Val
50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Tyr Gly Ser Tyr
            85                  90
```

<210> SEQ ID NO 105
<211> LENGTH: 94
<212> TYPE: PRT
<213> ORGANISM: Homo Sapiens

<400> SEQUENCE: 105

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Gly Arg Arg Tyr Gly Gln Glu Phe Thr Val
            35                  40                  45

Pro Gly Ser Lys Ser Thr Ala Thr Ile Ser Glu Leu Leu Ser Glu Val
50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Ser Leu Arg Tyr
            85                  90
```

<210> SEQ ID NO 106
<211> LENGTH: 94
<212> TYPE: PRT
<213> ORGANISM: Homo Sapiens

<400> SEQUENCE: 106

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Ser Gly Tyr Arg Tyr Gln Glu Phe Thr Val
            35                  40                  45

Pro Gly Ser Lys Ser Thr Ala Thr Ile Ser Gly Tyr Arg Glu His Val
50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Gln Glu Ser Tyr
```

<210> SEQ ID NO 107
<211> LENGTH: 94
<212> TYPE: PRT
<213> ORGANISM: Homo Sapiens

<400> SEQUENCE: 107

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Ser Gly Arg Arg Gly Gln Glu Phe Thr Val
                35                  40                  45

Pro Gly Ser Lys Ser Thr Ala Thr Ile Ser Pro Ser Leu Glu Val
                50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Arg Ser Gly Tyr
                85                  90

<210> SEQ ID NO 108
<211> LENGTH: 94
<212> TYPE: PRT
<213> ORGANISM: Homo Sapiens

<400> SEQUENCE: 108

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Pro Arg Arg Tyr Gln Glu Phe Thr Val
                35                  40                  45

Pro Gly Ser Lys Ser Thr Ala Thr Ile Ser Pro Gly Gly Gln Ser Val
                50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Gly Arg Gly Tyr
                85                  90

<210> SEQ ID NO 109
<211> LENGTH: 94
<212> TYPE: PRT
<213> ORGANISM: Homo Sapiens

<400> SEQUENCE: 109

Val Ser Asp Val Pro Arg Asp Leu Glu Val Val Ala Ala Thr Thr Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Ser Gly Arg Gly Ala Gln Glu Phe Thr Val
                35                  40                  45

Pro Gly Ser Lys Ser Thr Ala Thr Ile Ser Gly Leu Gly Pro Val
                50                  55                  60

Asp Tyr Thr Ile Thr Val Tyr Ala Val Thr Gly Arg Gly Glu Ser Pro
65                  70                  75                  80

Ala Ser Ser Lys Pro Ile Ser Ile Asn Tyr Arg Ser Gln His
                85                  90

<210> SEQ ID NO 110
<211> LENGTH: 97
<212> TYPE: PRT
<213> ORGANISM: Homo Sapiens

<400> SEQUENCE: 110

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Ser Ser Gly Tyr Ala Glu Arg Gly Gln Glu
        35                  40                  45

Phe Thr Val Pro Gly Ser Lys Ser Thr Ala Thr Ile Ser Ser Pro Gly
    50                  55                  60

Ala Arg Val Asp Tyr Thr Ile Thr Val Tyr Ala Val Thr Gly Arg Gly
65                  70                  75                  80

Glu Ser Pro Ala Ser Ser Lys Pro Ile Ser Ile Asn Tyr Ser Ser Leu
                85                  90                  95

Gly

<210> SEQ ID NO 111
<211> LENGTH: 97
<212> TYPE: PRT
<213> ORGANISM: Homo Sapiens

<400> SEQUENCE: 111

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Ser Glu Gly Gly Ser Ser Arg Ser Gln Glu
        35                  40                  45

Phe Thr Val Pro Gly Ser Lys Ser Thr Ala Thr Ile Ser Arg Ser Tyr
    50                  55                  60

Gln Pro Val Asp Tyr Thr Ile Thr Val Tyr Ala Val Thr Gly Arg Gly
65                  70                  75                  80

Glu Ser Pro Ala Ser Ser Lys Pro Ile Ser Ile Asn Tyr Gly Ser Tyr
                85                  90                  95

Pro

<210> SEQ ID NO 112
<211> LENGTH: 97
<212> TYPE: PRT
<213> ORGANISM: Homo Sapiens

<400> SEQUENCE: 112

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Gln Tyr Tyr His Gln Gly Arg Arg Gln Glu
        35                  40                  45

Phe Thr Val Pro Gly Ser Lys Ser Thr Ala Thr Ile Ser Arg Tyr Gly
    50                  55                  60

Gly Ser Val Asp Tyr Thr Ile Thr Val Tyr Ala Val Thr Gly Arg Gly
65                  70                  75                  80

Glu Ser Pro Ala Ser Ser Lys Pro Ile Ser Ile Asn Tyr Tyr Ala Tyr
                85                  90                  95

Gly

<210> SEQ ID NO 113
<211> LENGTH: 97
<212> TYPE: PRT
<213> ORGANISM: Homo Sapiens

<400> SEQUENCE: 113

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Arg Gly Gln Tyr Gly Ser Ser Gln Glu
                35                  40                  45

Phe Thr Val Pro Gly Ser Lys Ser Thr Ala Thr Ile Ser Ser Pro Glu
            50                  55                  60

Gly Ser Val Asp Tyr Thr Ile Thr Val Tyr Ala Val Thr Gly Arg Gly
65                  70                  75                  80

Glu Ser Pro Ala Ser Ser Lys Pro Ile Ser Ile Asn Tyr Ser Arg Ser
                85                  90                  95

Glu

<210> SEQ ID NO 114
<211> LENGTH: 97
<212> TYPE: PRT
<213> ORGANISM: Homo Sapiens

<400> SEQUENCE: 114

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Gln Arg Tyr Ser Tyr Tyr Gly Gln Gln Glu
                35                  40                  45

Phe Thr Val Pro Gly Ser Lys Ser Thr Ala Thr Ile Ser Ser Gly Arg
            50                  55                  60

Ser Ser Val Asp Tyr Thr Ile Thr Val Tyr Ala Val Thr Gly Arg Gly
65                  70                  75                  80

Glu Ser Pro Ala Ser Ser Lys Pro Ile Ser Ile Asn Tyr Arg Arg Ser
                85                  90                  95

Tyr

<210> SEQ ID NO 115
<211> LENGTH: 97
<212> TYPE: PRT
<213> ORGANISM: Homo Sapiens

<400> SEQUENCE: 115

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Arg Pro Ala Ser Tyr Arg Ala Ala Gln Glu
                35                  40                  45

```
Phe Thr Val Pro Gly Ser Lys Ser Thr Ala Thr Ile Ser Ser Tyr Ser
    50                  55                  60

Tyr Ser Val Asp Tyr Thr Ile Thr Val Tyr Ala Val Thr Gly Arg Gly
65                  70                  75                  80

Glu Ser Pro Ala Ser Ser Lys Pro Ile Ser Ile Asn Tyr Arg Arg Ser
                    85                  90                  95

Gly

<210> SEQ ID NO 116
<211> LENGTH: 97
<212> TYPE: PRT
<213> ORGANISM: Homo Sapiens

<400> SEQUENCE: 116

Val Ser Asp Val Pro Arg Asp Leu Glu Val Val Ala Ala Thr Pro Thr
1               5                   10                  15

Ser Leu Leu Ile Ser Trp Asp Ala Pro Thr Val Thr Val Arg Tyr Tyr
                20                  25                  30

Arg Ile Thr Tyr Gly Glu Pro Gln Ala Ser His Arg Pro Tyr Gln Glu
            35                  40                  45

Phe Thr Val Pro Gly Ser Lys Ser Thr Ala Thr Ile Ser Ser Arg Ser
    50                  55                  60

Gln Ser Val Asp Tyr Thr Ile Thr Val Tyr Ala Val Thr Gly Arg Gly
65                  70                  75                  80

Glu Ser Pro Ala Ser Ser Lys Pro Ile Ser Ile Asn Tyr Leu Arg Glu
                85                  90                  95

Leu

<210> SEQ ID NO 117
<211> LENGTH: 96
<212> TYPE: PRT
<213> ORGANISM: Homo Sapiens

<400> SEQUENCE: 117

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
                20                  25                  30

Tyr Tyr Arg Ile Thr Tyr Gly Glu Thr Gly Gly Asn Ser Pro Val Gln
            35                  40                  45

Glu Phe Thr Val Pro Leu Gln Pro Pro Leu Ala Thr Ile Ser Gly Leu
    50                  55                  60

Lys Pro Gly Val Asp Tyr Thr Ile Thr Val Tyr Ala Val Thr Lys Glu
65                  70                  75                  80

Arg Asn Gly Arg Glu Leu Phe Thr Pro Ile Ser Ile Asn Tyr Arg Thr
                85                  90                  95

<210> SEQ ID NO 118
<211> LENGTH: 10
<212> TYPE: PRT
<213> ORGANISM: Homo Sapiens

<400> SEQUENCE: 118

Gly Gly Gly Gly Ser Gly Gly Gly Gly Ser
1               5                   10
```

```
<210> SEQ ID NO 119
<211> LENGTH: 215
<212> TYPE: PRT
<213> ORGANISM: Homo Sapiens

<400> SEQUENCE: 119

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Leu Gln Pro Pro Leu Ala Thr Ile Ser Gly Leu
    50                  55                  60

Lys Pro Gly Val Asp Tyr Thr Ile Thr Val Tyr Ala Val Thr Lys Glu
65                  70                  75                  80

Arg Asn Gly Arg Glu Leu Phe Thr Pro Ile Ser Ile Asn Tyr Arg Thr
                85                  90                  95

Gly Gly Gly Gly Ser Gly Gly Gly Ser Val Ser Asp Val Pro Arg
            100                 105                 110

Asp Leu Glu Val Val Ala Ala Thr Pro Thr Ser Leu Leu Ile Ser Trp
        115                 120                 125

Asp Ala Pro Ala Val Thr Val Arg Tyr Tyr Arg Ile Thr Tyr Gly Arg
    130                 135                 140

Thr Asp Ala Lys Ser Thr Arg Lys Glu Phe Thr Val Pro Gly Ser Lys
145                 150                 155                 160

Ser Thr Ala Thr Ile Gly Glu Leu Lys Arg Gly Arg Asp Tyr Thr Ile
                165                 170                 175

Thr Val Tyr Ala Val Thr Gly Arg Gly Asp Ser Pro Ala Ser Ser Lys
            180                 185                 190

Pro Ile Ser Ile Asn Tyr Arg Pro Glu Lys Glu Asn Leu Tyr Phe Gln
        195                 200                 205

Gly His His His His His His
    210                 215

<210> SEQ ID NO 120
<211> LENGTH: 111
<212> TYPE: PRT
<213> ORGANISM: Homo Sapiens

<400> SEQUENCE: 120

Met Gly Val Ser Asp Val Pro Arg Asp Leu Glu Val Val Ala Ala Thr
1               5                   10                  15

Pro Thr Ser Leu Leu Ile Ser Trp Arg His Pro His Phe Pro Thr Arg
            20                  25                  30

Tyr Tyr Arg Ile Thr Tyr Gly Arg Thr Asp Ala Lys Ser Thr Arg Lys
        35                  40                  45

Glu Phe Thr Val Pro Leu Gln Pro Pro Leu Ala Thr Ile Gly Glu Leu
    50                  55                  60

Lys Arg Gly Arg Asp Tyr Thr Ile Thr Val Tyr Ala Val Thr Lys Glu
65                  70                  75                  80

Arg Asn Gly Arg Glu Leu Phe Thr Pro Ile Ser Ile Asn Tyr Arg Pro
                85                  90                  95

Glu Lys Glu Asn Leu Tyr Phe Gln Gly His His His His His His
            100                 105                 110
```

```
<210> SEQ ID NO 121
<211> LENGTH: 10
<212> TYPE: PRT
<213> ORGANISM: Homo Sapiens

<400> SEQUENCE: 121

Gly Ser Gly Ser Gly Ser Gly Ser Gly Ser
1               5                   10

<210> SEQ ID NO 122
<211> LENGTH: 7
<212> TYPE: PRT
<213> ORGANISM: Homo Sapiens

<400> SEQUENCE: 122

Pro Ser Thr Ser Thr Ser Thr
1               5

<210> SEQ ID NO 123
<211> LENGTH: 7
<212> TYPE: PRT
<213> ORGANISM: Homo Sapiens

<400> SEQUENCE: 123

Glu Ile Asp Lys Pro Ser Gln
1               5
```

FIBRONECTIN-BASED BINDING MOLECULES AND USES THEREOF

PRIORITY INFORMATION

This application is a U.S. National Phase filing of International Serial No. PCT/EP2009/055365 filed May 4, 2009, and claims priority to U.S. Application Ser. No. 61/050,142, filed May 2, 2008, the contents of which are incorporated herein by reference in their entirety.

RELATED INFORMATION

The contents of any patents, patent applications, and references cited throughout this specification are hereby incorporated by reference in their entireties.

BACKGROUND OF THE INVENTION

Molecules capable of specific binding to a desired target epitope are of enormous importance as both therapeutics and medical diagnostic tools. A well known example of this class of molecules is the monoclonal antibody. Antibodies can be selected that bind specifically and with high affinity to almost any structural epitope. As a result, antibodies are used routinely as research tools and as FDA approved therapeutics such that the worldwide market for therapeutic and diagnostic monoclonal antibodies is currently worth approximately $30 billion.

However, monoclonal antibodies have a number of shortcomings. For example, classical antibodies are large and complex molecules. They have a heterotetrameric structure comprising two light chains and two heavy chains connected together by both inter and intra disulphide linkages. This structural complexity precludes easy expression of antibodies in simple prokaryotic systems and requires that antibodies are produced in more elaborate (and expensive) mammalian cell systems. The large size of antibodies also limits their therapeutic effectiveness since they are often unable to efficiently penetrate certain tissue spaces. Therapeutic antibodies, because they possess an Fc region, occasionally trigger undesired effector cell function and/or clotting cascades. In addition, generating bispecific or multispecific antibodies often involves difficult and complex procedures (See e.g., Josefina et al., (1997), Nature Biotechnology, 15: 159-163; and Wu et al. (2007) Nature Biotechnology, 25: 1290-1297).

Accordingly there is a need in the art for alternative binding molecules capable of specific binding to a desired target with high affinity and specificity. A need also exists for a simple method to generate bispecific or multispecific binding molecules.

SUMMARY OF THE INVENTION

The present invention provides fibronectin type III (Fn3)-based binding molecules that specifically bind to a target antigen and, thus, can be used in a broad variety of therapeutic and diagnostic applications. The invention is based on the unexpected and surprising discovery that Fn3 comprising at least one modified bottom loop retains structural and conformational stability, and is able to bind to a target molecule. Furthermore, the invention is based on the discovery of novel bispecific Fn3-based binding molecules in which a single Fn3 molecule can bind one or more target molecules by using both the top and bottom loops of Fn3. The invention also provides a simple, efficient method for generating bispecific and multispecific Fn3-based binding molecules.

Accordingly, in one embodiment, the invention pertains to monospecific Fn3-based binding molecules that use the bottom AB, CD, EF loops or C-terminal to bind one or more target(s) ("bottom monospecific Fn3-based binding molecules") e.g., Human Serum Albumin (HSA), lyzozyme. These bottom monospecific Fn3-based binding molecules can be linked together (e.g., in pearl-like fashion) to form multispecific Fn3-based binding molecules that simultaneously bind to multiple targets, and/or can be conjugated to one or more non-Fn3 moieties (e.g., functional moieties), and/or can be conjugated to one or more non-Fn3 moieties (e.g., functional moieties), such as Human Serum Albumin (HSA), an antibody Fc region or polyethylene glycol (PEG), for example, to improve half life and stability of the Fn3-based binding molecule.

In another embodiment, the bottom monospecific Fn3-based binding molecules can be combined with Fn3-based binding molecules that use the top BC, DE, or FG loops to produce bispecific Fn3-based binding molecules. The invention further provides bispecific Fn3-based binding molecules that bind to two or more targets simultaneously These bispecific Fn3-based binding molecules also can be linked together (e.g., in pearl-like fashion) to form multispecific Fn3-based binding molecules that simultaneously bind to multiple targets, and/or can be conjugated to one or more non-Fn3 moieties (e.g., functional moieties) as described above. The invention further provides methods of screening libraries of Fn3-based binding molecules for specific binding to a target, typically a target protein, as well as methods for manufacturing Fn3-based binding molecules in, for example, prokaryotic or eukaryotic systems. Still further, the invention provides compositions (e.g., therapeutic compositions) comprising Fn3-based binding molecules, and uses of such compositions in a variety of therapeutic and diagnostic applications.

Accordingly, in one aspect, the invention provides an Fn3-based binding molecule comprising an Fn3-domain, wherein at least one amino acid in one or more of the bottom AB, CD, EF loop regions or the C-terminus of the Fn3 domain are altered compared to a wild-type Fn3 domain (e.g., SEQ ID NO:1) to create a non-Fn3 binding sequence which binds to a specific target. In a particular embodiment, the altered amino acid residues in the AB, CD, EF loop regions or C-terminus includes one or more of the amino acids at position 15, 16, 38, 39, 40, 41, 42, 43, 44, 45, 60, 61, 62, 63, 64, 93, 95, or 96 of SEQ ID NO:1. The non-Fn3 binding sequence can be, for example, all or a portion of a CDR region (e.g., an antibody CDR region) or a T-cell receptor.

In another aspect, the invention pertains to a Fn3-based binding molecule comprising a first Fn3-domain, wherein at least one amino acid in one or more of the bottom AB, CD or EF loop regions or C-terminal of the Fn3 domain are altered compared to the wild-type Fn3 domain comprising SEQ ID NO:1 to create a non-Fn3 binding sequence which binds to a first target, and wherein at least one amino acid in one or more of the bottom AB, CD or EF loop regions or C-terminal of a second Fn3 domain are altered compared to the wild-type Fn3 domain comprising SEQ ID NO:1 to create a non-Fn3 binding sequence which binds to a second target.

In another aspect, the invention provides a bispecific Fn3-based binding molecule comprising an Fn3 domain, wherein at least one amino acid in one or more of the bottom AB, CD, EF loop regions or C-terminus of the Fn3 domain are altered compared to a wild-type Fn3 domain (e.g., SEQ ID NO:1) to create a non-Fn3 binding sequence which binds to a first target, and wherein at least one amino acid in one or more of the top BC, DE or FG loop regions of the Fn3 domain are altered compared to a wild-type Fn3 domain comprising (e.g., SEQ ID NO:1) to create a non-Fn3 binding sequence which binds to a second target. In a particular embodiment, the altered amino acid residues in the bottom AB, CD, EF loop regions or C-terminus includes one or more of the amino acids at position 15, 16, 38, 39, 40, 41, 42, 43, 44, 45, 60, 61, 62, 63, 64, 93, 95, or 96 of SEQ ID NO:1, and the altered the amino acid residues in the top BC, DE or FG loop regions includes one or more of the amino acids at position 21, 22, 23, 24, 25, 26, 27, 28, 29, 30, 51, 52, 53, 54, 55, 56, 76, 77, 78, 79, 80, 80, 81, 82, 83, 84, 85, 86, 87, or 88 of SEQ ID NO:1. Accordingly, such bispecific Fn3-based binding molecules of the invention simultaneously bind to two or more targets present on the same molecule, or on different molecules.

In another aspect, the invention provides, multispecific Fn3-based binding molecules comprising two or more Fn3-based binding molecules of any of the preceding claims, linked together (e.g., in pearl-like fashion), such that they bind two or more targets on the same molecule or on different molecules.

"Fn3-based binding molecules" of the invention, (which hereafter, include bispecific and multispecific Fn3-based binding molecules) also can bind to, or be linked to, one or more non-Fn3 moieties that, for example, increase the half-life of the Fn3-based binding molecule when administered in vivo. Suitable non-Fn3 moieties include, but are not limited to, antibody Fc regions, Human Serum Albumin (HSA) (or portions thereof), polyethylene glycol (PEG) and/or polypeptides which bind to the aforementioned proteins or other serum proteins with increased half-life, such as, e.g., transferrin. Accordingly, in another aspect, the invention provides conjugates which include one or more Fn3-based binding molecules linked to a non-Fn3 moiety.

In yet another embodiment, the Fn3-based binding molecules and conjugates of the invention further comprise at least one modified amino acid residue compared to a wild-type Fn3 domain (e.g., SEQ ID NO: 1) for attaching a functional moiety. In one embodiment, the modified amino acid comprises substitution or addition of a cysteine or non-natural amino acid residue in one or more regions selected from a loop region, a beta-strand region, a beta-like strand region, a C-terminal region, the region between the C-terminus and the most C-terminal beta strand (or beta-like strand), an N-terminal region, and the region between the N-terminus and the most N-terminal beta strand (or beta-like strand).

Fn3-based binding molecules of the invention can be based on wild-type Fn3 sequences, (e.g., human Fn3 having the amino acid sequence shown in SEQ ID NO:1) as well as modified versions of such wild type sequences, as discussed herein. For example, the Fn3-based binding molecule can be a chimera having Fn3 beta-strands derived from at least two different fibronectin modules.

Also provided by the invention are compositions comprising the Fn-3 based binding molecules and conjugates of the invention, formulated with a suitable carrier.

The Fn-3 based binding molecules and conjugates of the invention can be used in a variety of therapeutic and diagnostic applications including, but not limited to, applications that antibodies can be used in. Such applications include, for example, treatment and diagnosis of autoimmune diseases, cancers and infectious diseases.

Other features and advantages of the invention will be apparent from the following detailed description and claims, such as a variegated nucleic acid library encoding Fn3-based binding molecules.

BRIEF DESCRIPTION OF THE DRAWINGS

FIG. 7 is a table showing the amino acid sequences of a selected number of monospecific Fn3-based binding molecules that use the bottom loops or C-terminal to bind human serum albumin.

FIG. 8 is a table showing the amino acid sequences of a selected number of monospecific Fn3-based binding molecules that use the bottom loops or C-terminal to bind lyzozyme.

DETAILED DESCRIPTION OF THE INVENTION

Figure 1:
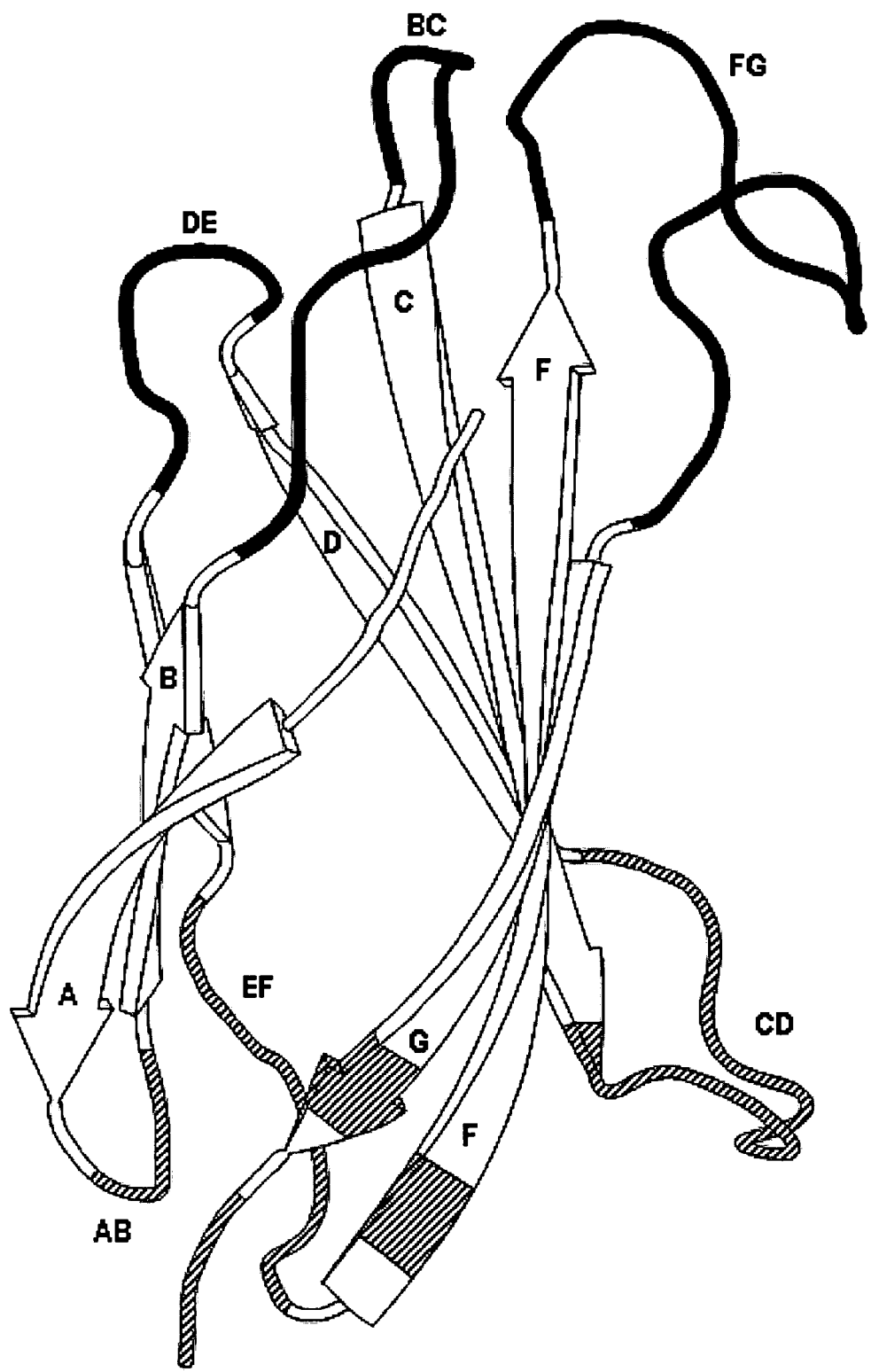
FIG. 1 shows a ribbon diagram of a Fn3-based binding molecule with loop and framework residues constituting the ligand binding surfaces highlighted.
Figure 2:
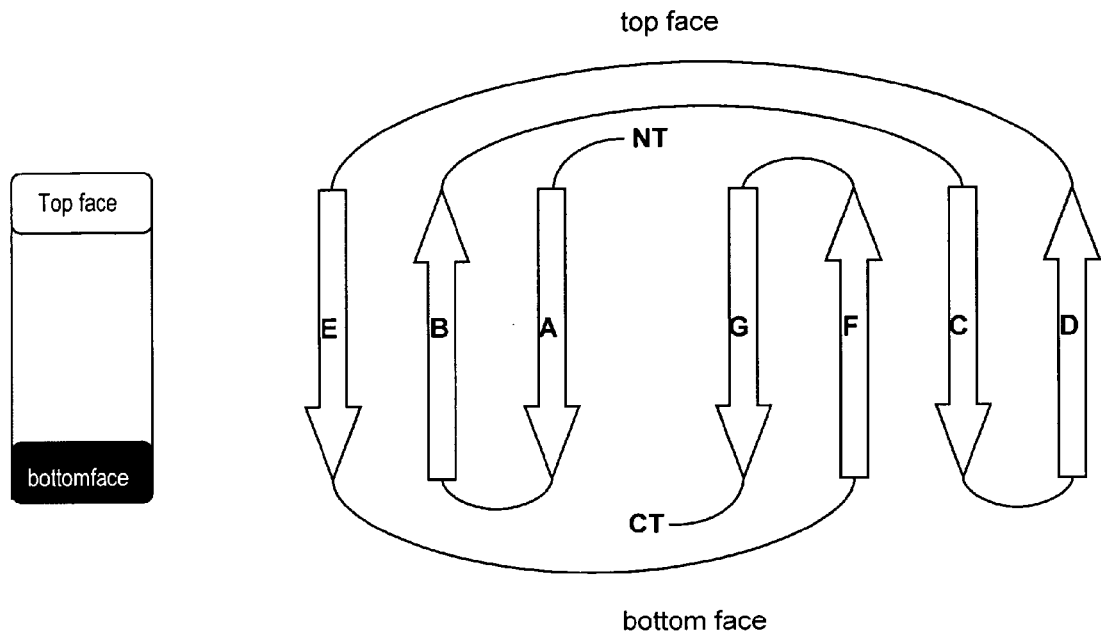
FIG. 2 depicts a schematic showing the top and bottom loop faces of Fn3.

In order to provide a clear understanding of the specification and claims, the following definitions are conveniently provided below.

Definitions

As used herein, the term "Fibronectin type III domain" or "Fn3 domain" refers to a wild-type Fn3 domain from any organism, as well as chimeric Fn3 domains constructed from beta strands from two or more different Fn3 domains. As is known in the art, naturally occurring Fn3 domains have a beta-sandwich structure composed of seven beta-strands, referred to as A, B, C, D, E, F, and G, linked by six loops, referred to as AB, BC, CD, DE, EF, and FG loops (See e.g., Bork and Doolittle, Proc. Natl. Acad. Sci. U.S.A 89:8990, 1992; Bork et al., Nature Biotech. 15:553, 1997; Meinke et al., J. Bacteriol. 175:1910, 1993; Watanabe et al., J. Biol. Chem. 265:15659, 1990; Main et al., 1992; Leahy et al., 1992; Dickinson et al., 1994; U.S. Pat. No. 6,673,901; Patent Cooperation Treaty publication WO/03104418; and, US patent application 2007/0082365, the entire teachings of which are incorporated herein by reference). Three loops are at the top of the domain (the BC, DE and FG loops) and three loops are at the bottom of the domain (the AB, CD and EF loops) (see FIG. 1). In a particular embodiment, of the invention, the Fn3 domain is from the tenth Fn3 domain of human Fibronectin ($^{10}$Fn3) (SEQ. ID. NO: 1).

As used herein the term "Fn3-based binding molecule" or "fibronectin type III (Fn3)-based binding molecule" refers to an Fn3 domain that has been altered to contain one or more non-Fn3 binding sequences. In a particular embodiment, one or more of the bottom AB, CD and/or EF loops are altered compared to the corresponding wild-type Fn3 domain to contain one or more non-Fn3-binding sequences. In another embodiment, one or more of the bottom AB, CD or EF loops and one or more of the top BC, DE and FG loops are altered compared to the corresponding wild-type Fn3 domain to contain one or more non-Fn3-binding sequences. Such molecules are referred to herein as "bispecific Fn3-based binding molecules". In a further embodiment, two or more Fn3-based binding molecules or bispecific Fn3-based binding molecule are linked together. Such molecules are referred to herein as "multispecific Fn3-based binding molecules".

The term "non-Fn3 binding sequence" refers to an amino acid sequence which is not present in the naturally occurring (e.g., wild-type) Fn3 domain, and which binds to a specific target. Such non-Fn3 binding sequences are typically introduced by modifying (e.g., by substitution and/or addition) the wild-type Fn3 domain (e.g., within the bottom loops and/or top loop regions). This can be achieved by, for example, random or predetermined mutation of amino acid residues within the wild-type Fn3 domain. Additionally or alternatively, the non-Fn3 binding sequence can be partly or entirely exogenous, that is, derived from a different genetic or amino acid source. For example, the exogenous sequence can be derived from a hypervariable region of an antibody, such as one or more CDR regions having a known binding specificity for a known target antigen. Such CDRs can be derived from a single antibody chain (e.g. a variable region of a light or heavy chain) or a from combination of different antibody chains. The CDRs can also be derived form two different antibodies (e.g., having different specificities). In a particular embodiment, the CDR(s) are derived from a nanobody, for example, a Camelidae-like heavy chain.

The term "monospecific" as used herein refers to an Fn3-based binding molecule that binds to one or more target molecules comprising Fn3 domains in which only the bottom region of the Fn3 domain, or the top region of the Fn3 domain, but not both, are used for binding. For example, a bottom monospecific Fn3-based binding molecule is one that uses only the bottom loops, such as the AB, CD, or EF loops, or C-terminal of the Fn3 domain to bind a target, while a top monospecific Fn3-based binding molecule uses only the top loops of the Fn3 domain, such as BC, DE, and FG loops, to bind the target. It is to be understood that not all three loops from the top or bottom region need to be used for binding the target molecule.

The monospecific Fn3 domains can also be linked together (e.g., in a pearl-like fashion) to form a multispecific Fn3-based binding molecules that comprises, for example, at least two monospecific Fn3 domains that are linked together. For bottom monospecific binding molecules, each of the Fn3 domains uses at least one bottom loop or C-terminal region to bind to one or more target molecules. In one embodiment, this multispecific Fn3-based binding molecule binds to different target regions of a same target molecule (e.g., Target A). For example, one Fn3 domain can bind to a first target region of Target A and another Fn3 domain can bind to a second target region of Target A. This can be used to increase avidity of the Fn3-based binding molecule for the target molecule. In another embodiment, the multispecific Fn3-based binding molecule binds to multiple target molecules. For example, one Fn3 domain can bind to Target A and a another Fn3 domain can bind to Target B (e.g., a half life extender). In yet another embodiment, the multispecific Fn3-based binding molecule comprises at least two monospecific Fn3 domains that bind to different target regions of Target A and at least two monospecific Fn3 domains that bind to different target regions of Target B. The skilled artisan will appreciate that any number of Fn3 domains can be linked in this fashion to create a multispecific Fn3-based binding molecule that are able to bind to different target regions of the same target molecule or different target molecules.

Figure 3:
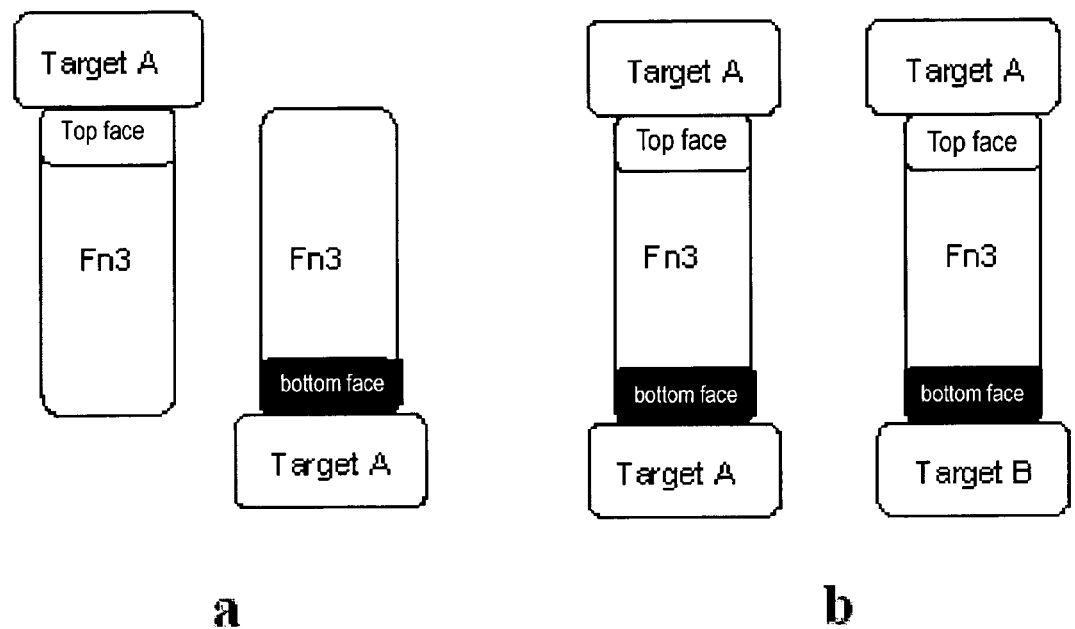
FIG. 3A is a schematic of a monospecific Fn3-binding molecule showing that either the top or bottom loops can be modified to bind to a single target, Target A.
FIG. 3B is a schematic of a bispecific Fn3-based binding molecule showing that both the top and bottom loops can be modified to bind a single target, Target A. The bispecific Fn3-based binding molecule can also be used to bind to two different targets, where the top loop binds to one target, Target A and bottom loops bind to a second target, Target B.
Figure 4A:
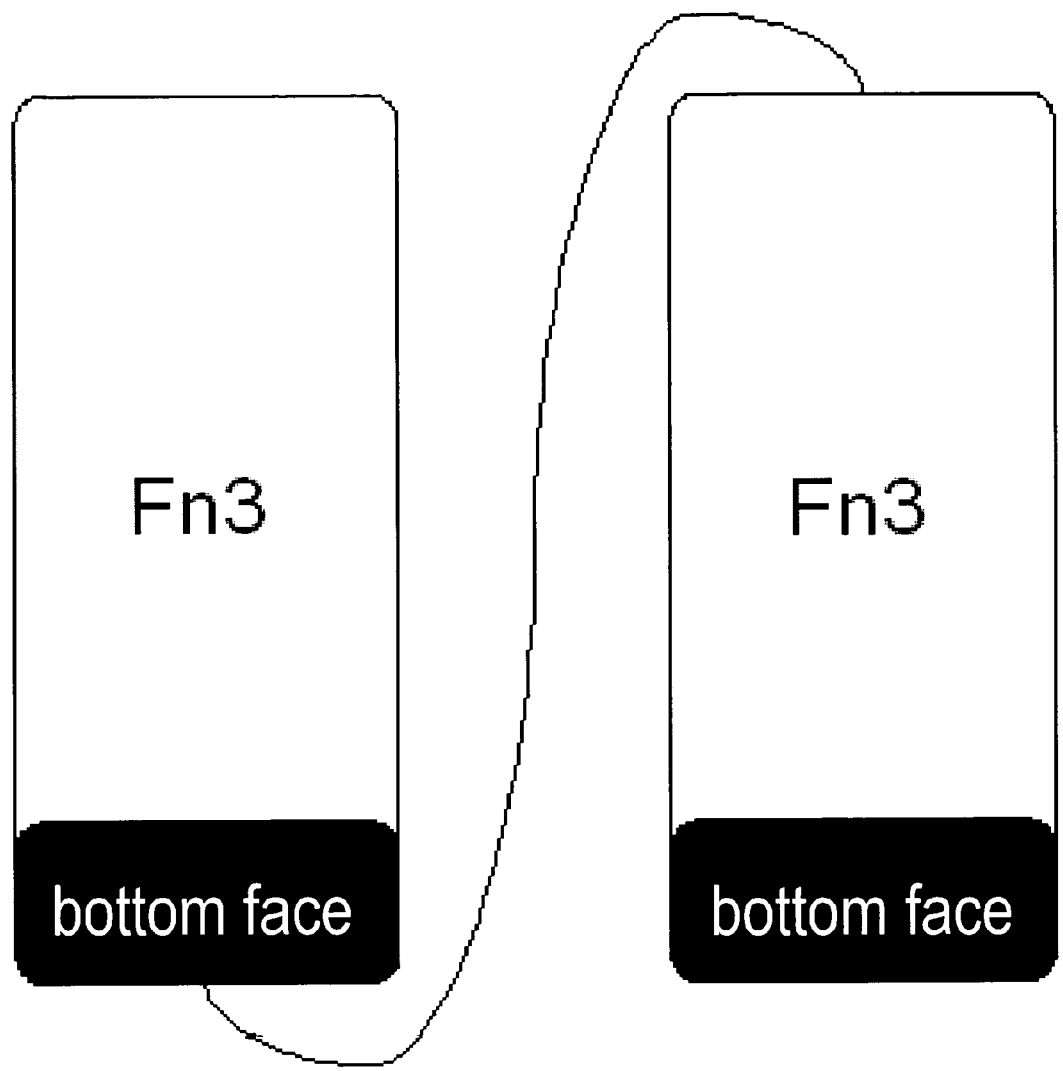
FIG. 4A is a schematic of a multispecific Fn3-based binding molecule comprising two bottom monospecific Fn3 domains with modifications to the bottom loops that are linked together.
Figure 4B:
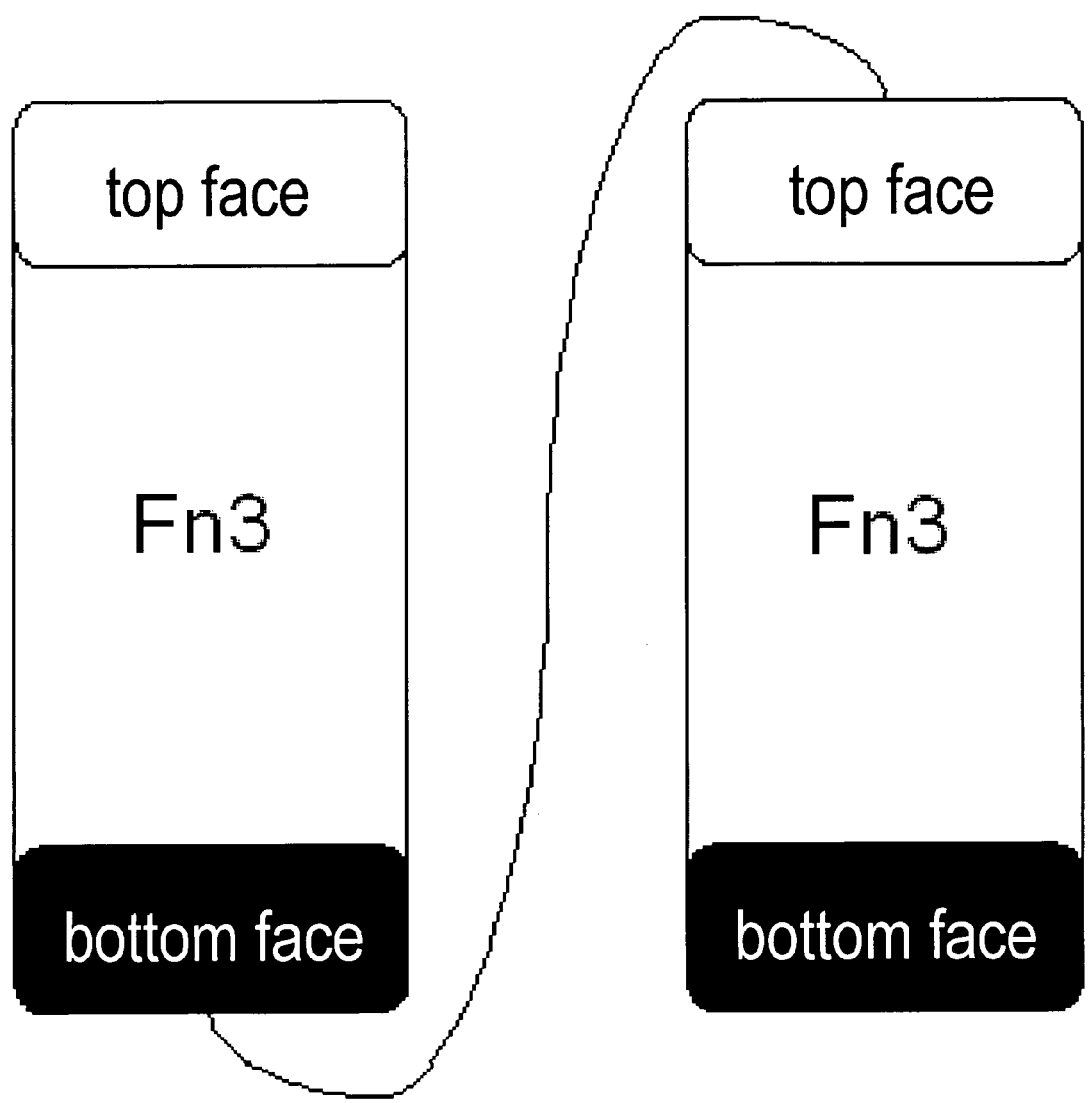
FIG. 4B is a schematic of a multispecific Fn3-based binding molecule comprising two bispecific Fn3 domains with modifications to the top and bottom loops that are linked together.
Figure 5A:
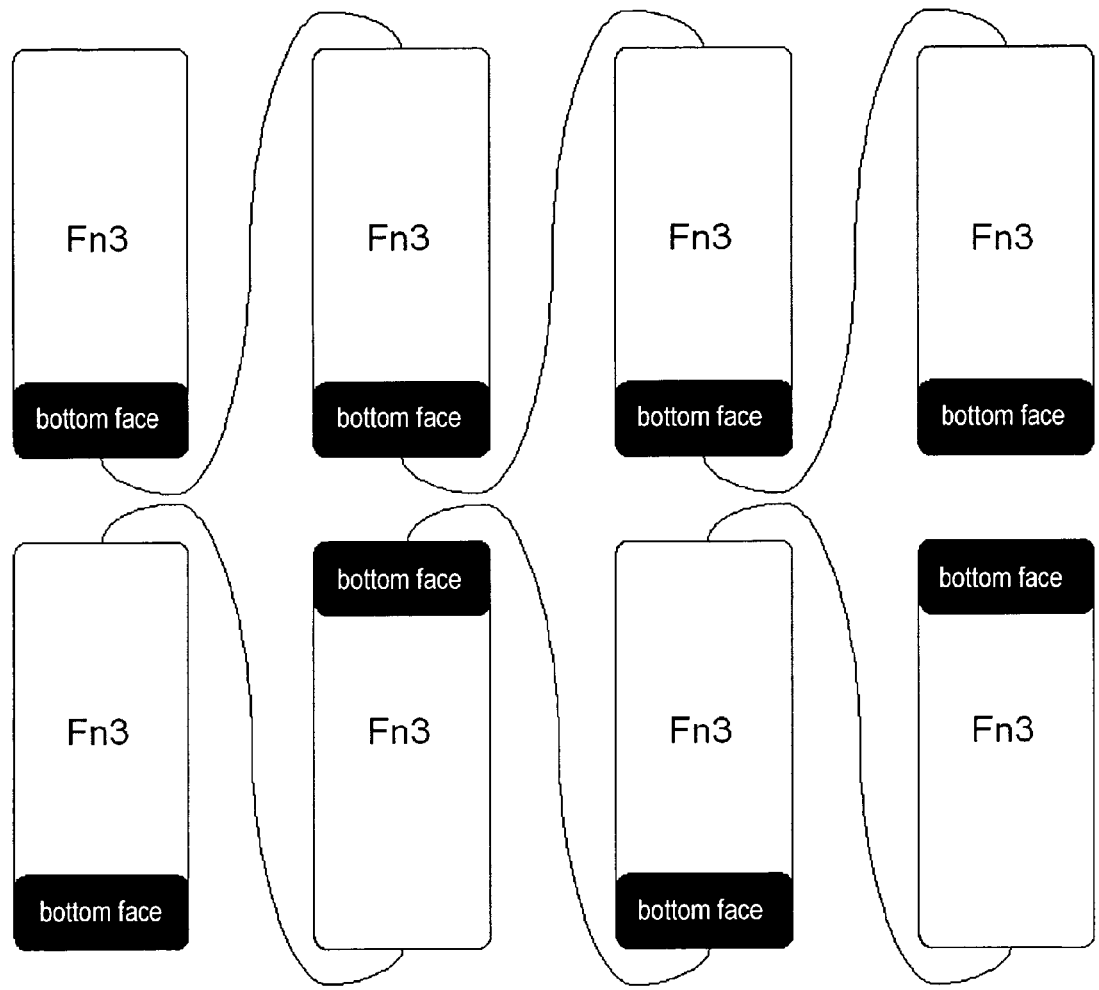
FIG. 5A is a schematic of a multispecific Fn3-binding molecule comprising multiple monospecific Fn3 domains with modifications to the bottom loops that are linked together.
Figure 5B:
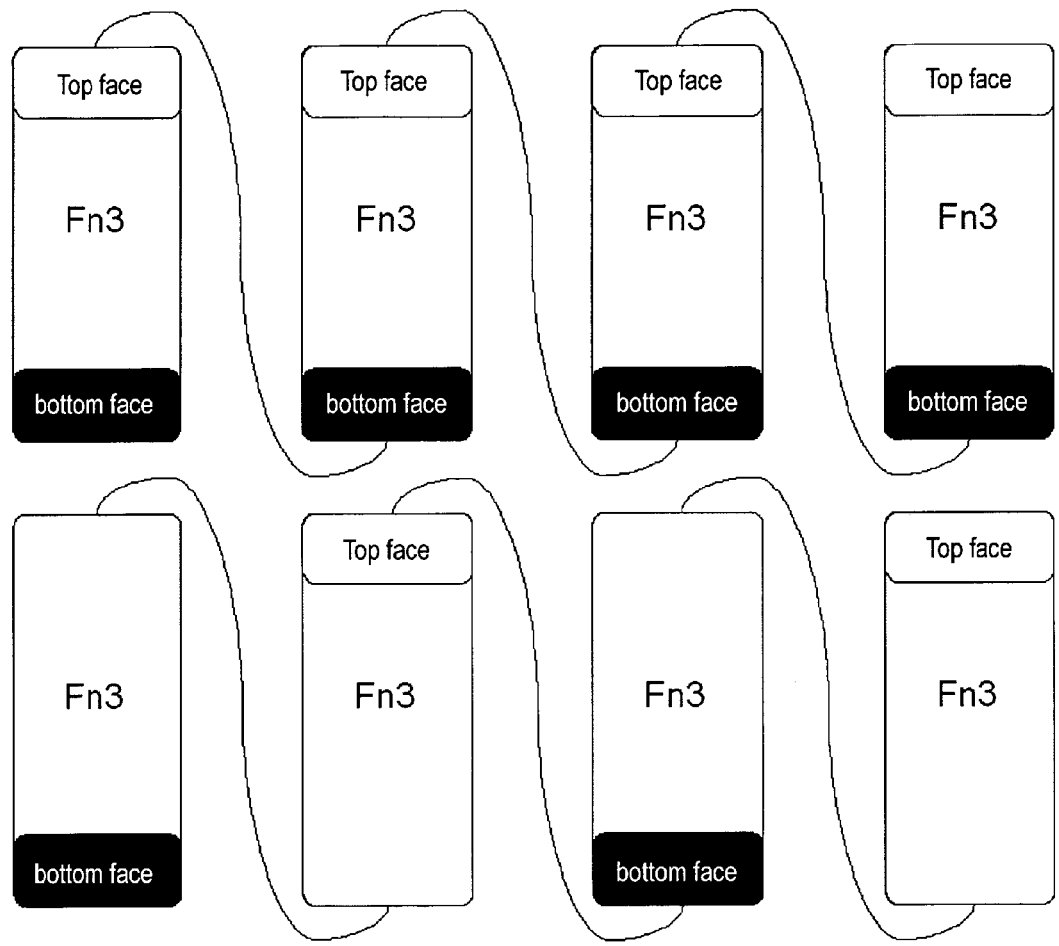
FIG. 5B is a schematic of a multispecific Fn3-binding molecule comprising multiple bispecific Fn3 domains with modifications to the top and bottom loops that are linked together.

The term "bispecific" as used herein refers to an Fn3-based binding molecule that binds to one or more targets using both the bottom region of the Fn3 domain and the top region of the Fn3 domain. For example a bispecific Fn3-based binding molecule comprises Fn3 domains that use both the bottom loops, such as the AB, CD, or EF loops, or C-terminal of the molecule and the top loops of the molecule, such as BC, DE, and FG loops, to bind the target. The bispecific Fn3-based binding molecules can be used to bind the same target molecule, e.g., Target A, which can bind to both the top and bottom of the bispecific Fn3-based binding molecule (See FIG. 3b). Alternatively, the bispecific Fn3-based binding molecule can be used to bind to two different target molecules, e.g., Target A and Target B. In this instance, the top loops can be used to bind to Target A and the bottom loops can be used to bind to Target B, or visa versa (See FIG. 3b). The bispecific Fn3-based binding molecules can also be linked together (e.g., in a pearl-like fashion) to form a multispecific Fn3-based binding molecules.

The term "multispecific" as used herein refers to a Fn3-based binding molecule that comprises at least two monospecific Fn3-based binding molecules linked together or at least two bispecific Fn3-based binding molecules linked together.

The term "complementarity determining region (CDR)" refers to a hypervariable loop from an antibody variable domain or from a T-cell receptor. The position of CDRs within a antibody variable region have been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al., J. Mol. Biol. 196:901-917, 1987, which are incorporated herein by reference). The term "single domain antibodies" refers to any naturally-occurring single variable domain and corresponding engineered binding fragments, including human domain antibodies as described by Domantis (Domantis/GSK (Cambridge, UK) or camelid nanobodies as defined hereafter.

The term "single chain antibody" refers to an antigen binding portion of a light chain variable region and an antigen binding portion of a heavy chain variable region, joined, using recombinant methods, by a synthetic linker that enables them to be made as a single protein chain in which the VL and VH regions pair to form monovalent molecules (known as single chain FIT (scFv); see e.g., Bird et al. (1988) Science 242:423-426; and Huston et al. (1988) Proc. Natl. Acad. Sci. U.S.A 85:5879-5883).

The term "camelid nanobody" refers to a region of camelid antibody which is the small single variable domain devoid of light chain and that can be obtained by genetic engineering to yield a small protein having high affinity for a target, resulting in a low molecular weight antibody-derived protein. See WO07042289 and U.S. Pat. No. 5,759,808 issued Jun. 2, 1998; see also Stijlemans, B. et al., 2004. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The term "target" refers to an antigen or epitope recognized by Fn3-based binding molecule of the invention. Targets include, but are not limited to, epitopes present on proteins, peptides, carbohydrates, and/or lipids.

The term "conjugate" refers to an Fn3-based binding molecule chemically or genetically linked to one or more non-Fn3 moieties.

The term "non-Fn3 moiety" refers to a biological or chemical entity that imparts additional functionality to a molecule to which it is attached. In a particular embodiment, the non-Fn3 moiety is a polypeptide, e.g., human serum albumin (HSA), or a chemical entity, e.g., polyethylene gycol (PEG) which increases the half-life of the Fn3-based binding molecule in vivo.

The term "non-natural amino acid residue" refers to an amino acid residue that is not present in the naturally occurring (wild-type) Fn3 domain. Such non-natural amino acid residues can be introduced by substitution of naturally occurring amino acids, and/or by insertion of non-natural amino acids into the naturally occurring amino acid Fn3 sequence. The non-natural amino acid residue also can be incorporated such that a desired functionality is imparted to the Fn3-based binding molecule, for example, the ability to link a functional moiety (e.g., PEG).

The term "polyethylene glycol" or "PEG" refers to a polyalkylene glycol compound or a derivative thereof, with or without coupling agents or derviatization with coupling or activating moieties.

The term "specific binding" or "specifically binds to" refers to the ability of an Fn3-based binding molecule to bind to a target with an affinity of at least $1\times10^{-6}$ M, and/or bind to a target with an affinity that is at least two-fold, (preferably at least 10 fold), greater than its affinity for a nonspecific antigen at room temperature under standard physiological salt and pH conditions, as measured by surface plasmon resonance.

Overview

The present invention provides fibronectin type III (Fn3)-based binding molecules that specifically bind to a target antigen. The invention provides for monospecific Fn3-binding molecules with modifications to at least one or more of the bottom AB, CD, EF loop regions or C-terminus that binds to one or more target molecules. The invention further provides bispecific Fn3-based binding molecules that bind to the same target molecule with two opposite binding sites or to two or more target antigens simultaneously. The Fn3-based binding molecules of the invention also can be linked together (e.g., in pearl-like fashion) to form multispecific Fn3-based binding molecules and/or can be conjugated to a non-Fn3 moiety, such as Human Serum Albumin (HSA), to improve half life and stability. The Fn3-based binding molecules can be used in a variety of therapeutic and diagnostic applications, much like other binding molecules, such as antibodies.

Monospecific Fn3-Based Binding Molecules

In one aspect, the invention provides monospecific Fn3-based binding molecules which are altered compared to the wild-type Fn3 domain (e.g., in the bottom and/or top loop regions) to create a non-Fn3 binding sequence which binds to a specific target. In one embodiment, the monospecific Fn3-based binding molecules use the bottom AB, CD, EF loops or C-terminal to bind one or more targets molecules.

Accordingly, in one embodiment, the invention provides an Fn3-based binding molecule comprising an Fn3 domain, wherein at least one amino acid in one or more of the of the Fn3 domain is altered compared to a wild-type Fn3 domain to create a non-Fn3 binding sequence which binds to a specific target. In particular embodiment the wild type Fn3 domain is a human Fn3 domain, e.g., human $^{10}$Fn3 (SEQ ID NO:1). Additionally, one or more amino acid residues in one or more beta-strands adjacent to the loop regions can also be mutated compared to the wild-type Fn3 domain to contribute additional non-Fn3 binding sequences or residues which can be linked to non-Fn3 moieties. Particular amino acid residues in the bottom AB, CD, EF loop regions or C-terminus and adjacent beta strands which can be altered include, for example, amino acids at position 15, 16, 38, 39, 40, 41, 42, 43, 44, 45, 60, 61, 62, 63, 64, 93, 95, or 96 of SEQ ID NO:1.

Exemplary non-Fn3 binding sequences include, for example, all or a portion of a complementarity determining region (CDR) of an antibody or a T-cell receptor.

In another aspect, the invention provides a library of Fn3-based binding molecules, which can be used to identify Fn3-based binding molecules which bind to a particular desired target. In one embodiment, the library comprises Fn3-based binding molecules, each of which contains at least one amino acid alteration in one or more of the bottom AB, CD, EF loop regions or C-terminus compared to a wild-type Fn3 domain, such as the human $^{10}$Fn3 (SEQ ID NO:1). Particular amino acid residues in the AB, CD or EF loop regions and beta strands which can be altered include, for example, amino acids at position 15, 16, 38, 39, 40, 41, 42, 43, 44, 45, 60, 61, 62, 63, 64, 93, 95, or 96 of SEQ ID NO:1.

In a another embodiment, the library comprises Fn3-based binding molecules, each of which contains at least one amino acid alteration in one or more of the top BC, DE or FG loop regions compared to a wild-type Fn3 domain, such as the human $^{10}$Fn3 (SEQ ID NO:1). Particular amino acid residues in the BC, DE or FG loop regions and beta strands which can be altered include, for example, amino acids at position 21, 22, 23, 24, 25, 26, 27, 28, 29, 30, 51, 52, 53, 54, 55, 56, 76, 77, 78, 79, 80, 80, 81, 82, 83, 84, 85, 86, 87, or 88 of SEQ ID NO:1.

Library diversity can be generated by, for example, random mutagenesis, "walk though mutagenesis, or "look through mutagenesis of one or more of the disclosed residues in SEQ ID NO:1 (U.S. Pat. Nos. 7,195,880; 6,951,725; 7,078,197; 7,022,479; 5,922,545; 5,830,721; 5,605,793, 5,830,650; 6,194,550; 6,699,658; 7,063,943; 5,866,344 and Patent Cooperation Treaty publication WO06023144).

Alternatively, Fn3-based binding molecules can be generated by combining non-Fn3-binding sequences from one or more different library members. In a particular embodiment, bispecific Fn3-based binding molecules are generated by combining non-Fn3-binding sequences from one or more of the bottom AB, CD, EF loop regions or C-terminus of one library member, together with non-Fn3-binding sequences from one or more of the top BC, DE or FG loop regions of another library member, into a single bispecific Fn3-based binding molecule.

Nucleic acids encoding the library of Fn3-based binding molecules, or variants thereof, described herein can be constructed using art recognized methods including, but not limited to, PCR-based or enzyme-mediate genetic engineering, ab initio DNA or RNA synthesis, and/or cassette mutagenesis.

Suitable targets for Fn3-based binding molecules include, but are not limited to, half-life extenders (e.g., HSA), lysozyme, a cellular receptor, a cellular receptor ligand, a bacteria, or a virus (see, FIG. 1). In a particular embodiment the target is involved in a human disease, e.g., an autoimmune disease, cancer, or an infectious disease.

This specification describes, inter alia, the identification and production of novel, Fn3-based binding molecules that bind to a target, e.g., HSA, using the bottom loops of the Fn3 molecule. Hundreds of clones were generated using the methods of the invention and a representative few have been characterized as shown in Example 4. FIG. 7 shows a representative number of sequences isolated from this library of Fn3 scaffold proteins that bind to HSA (SEQ ID NOs: 7-41).

Furthermore, it was discovered that many independently randomized loops tended to converge to a consensus sequence that is likely to participate in HSA binding (SEQ ID NO: 42). Therefore, it is expected that polypeptides having this consensus sequences will be useful as HSA binding agents even when separated from the protein context in which they were identified.

Figure 8:
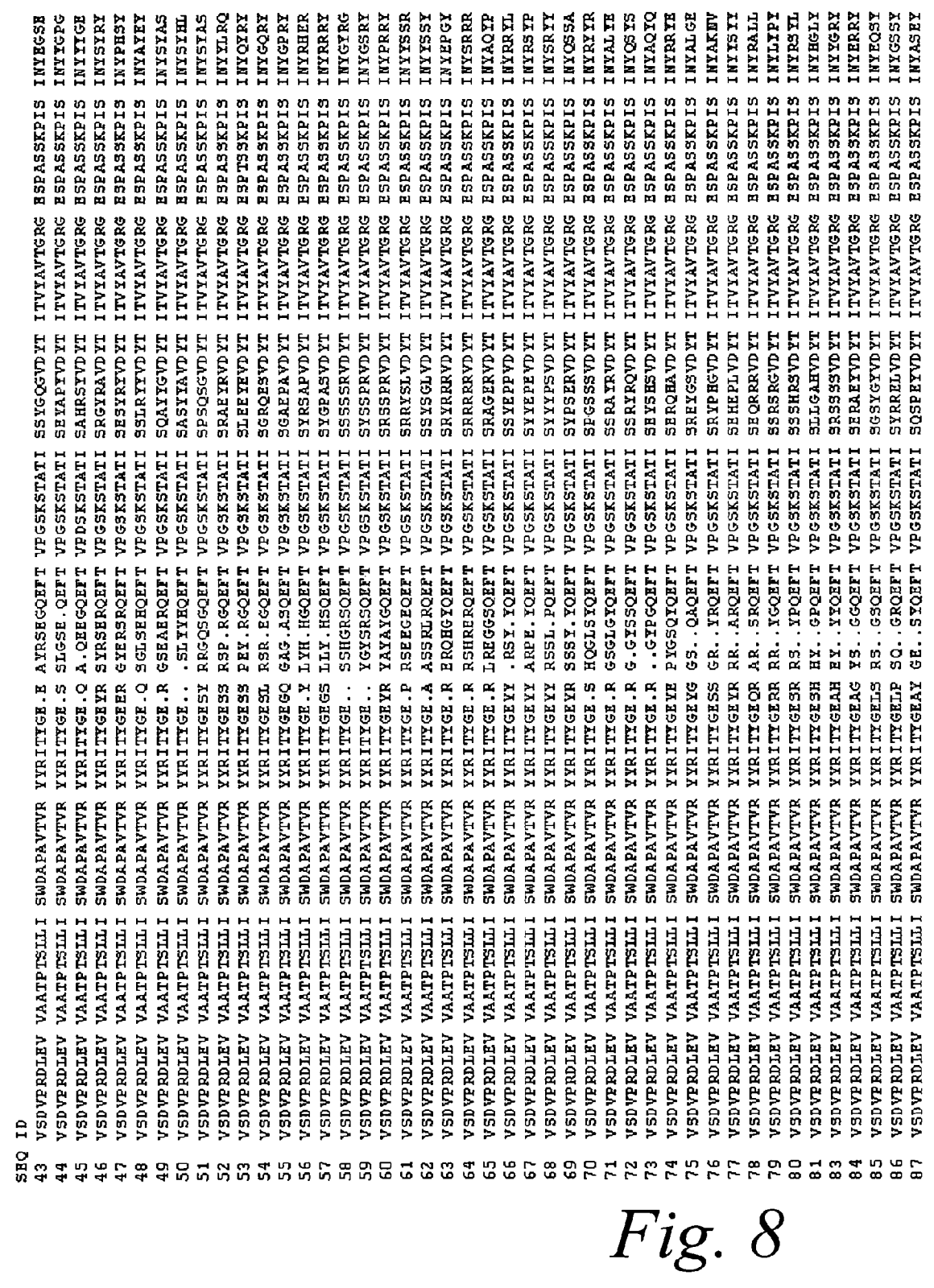

FIG. 8 shows a representative number of sequences isolated from this library of Fn3 scaffold proteins that bind to lysozyme (SEQ ID NOs: 43-116). The data in the Example 5 shows binding studies of s representative few Fn3-based binding proteins for HSA. The results show that Fn3 binding molecules can be generated with modified bottom loops that have the ability to bind a target.

This data shows that a library of Fn3-based binding molecules can be generated in which at least one of the bottom loops is modified such that it binds to a target. With the HSA library, the bottom loops were kept at the same length as wild type Fn3. With the lyzozyme library, the bottom loops were varied in length without adverse effects on the protein structure. Furthermore, these monospecific Fn3-based binding molecules with the modified bottom loops, maintain conformational stability and can be expressed and purified while retaining binding ability. Thus, the methods of the invention can be used to generate a library of Fn3-based binding molecules that have at least one modified bottom loop as well as Fn3-based binding molecules that use the bottom face to bind a target.

Bispecific Fn3-Based Binding Molecules

As discussed in part above, in another aspect, the invention provides bispecific Fn3-based binding molecules which are able to bind to two or more targets simultaneously. Such bispecific Fn3-based binding molecules comprise two or more non-Fn3 binding sequences within the same protein domain. This can be achieved by altering any two or more of the top and bottom AB, BC, CD, DE, EF or FG loop regions to comprise non-Fn3 binding sequences (see FIG. 1). In a particular embodiment, the bispecific Fn3-based binding molecule is altered in both the top and bottom loop regions to create two separate binding specificities.

Accordingly, in one embodiment, the invention provides a bispecific Fn3-based binding molecule comprising an Fn3 domain, wherein at least one amino acid in one or more of the bottom AB, CD or EF loop regions of the Fn3 domain is altered compared to a wild-type Fn3 domain (e.g., SEQ ID NO:1) to create a non-Fn3 binding sequence which binds to a first target, and wherein at least one amino acid in one or more of the top BC, DE and FG loop regions of the Fn3 domain is altered compared to a wild-type Fn3 domain (e.g., SEQ ID NO:1) to create a non-Fn3 binding sequence which binds to a second target. Particular amino acid residues in the bottom AB, CD, EF loop regions or C-terminus and adjacent beta strands which can be altered include, for example, amino acids at position 15, 16, 38, 39, 40, 41, 42, 43, 44, 45, 60, 61, 62, 63, 64, 93, 95, or 96 of SEQ ID NO:1. Particular amino acid residues in the top BC, DE and FG loop regions and adjacent beta strands which can be altered include, for example, amino acids at position 21, 22, 23, 24, 25, 26, 27, 28, 29, 30, 51, 52, 53, 54, 55, 56, 76, 77, 78, 79, 80, 80, 81, 82, 83, 84, 85, 86, 87, or 88 of SEQ ID NO:1.

Bispecific Fn3-based binding molecules of the invention bind to two or more targets simultaneously. The targets can be present on the same molecule, such that two regions of the same target molecule become juxtaposed by the binding of the bispecific Fn3-based binding domain to the targets. Alternatively, the targets can be present on different molecules, such that the two different molecules become juxtaposed by the binding of the bispecific Fn3-based binding molecule to the targets. The targets can also be identical, such that the bispecific Fn3-based binding molecule is able to cluster target molecules, in the same way as an antibody is able to cluster molecules.

Suitable targets include those previously mentioned above, alone or in combination with targets present on molecules that enhance the physiochemical properties of the bispecific Fn3-based binding molecule, such as a half-life extender, e.g., HSA, an antibody Fc receptor or PEG. Suitable targets also include molecules that confer additional functional properties e.g. cytotoxic, labeling or imaging moieties, as described herein. Suitable targets can also be used to induce dimerization of bispecific Fn3-based binding molecules if the two bispecific Fn3-based binding domain molecules are capable of binding to the target simultaneously. For example, two bispecific Fn3-based binding molecules can work with an idiotype/anti-idiotype relationship. In this instance, one binding site of a Fn3-binding molecule will bind to a target molecule while the second binding site of the Fn3-binding molecule will bind to a binding region on the Fn3-binding molecule. For example, the bottom loops of the bispecific Fn3-binding molecule may bind to Target A while the top loops of the bispecific molecule may bring to a second bispecific Fn3-binding molecule. This will lead to multimerisation of the Fn3-binding molecules in such a fashion that the bottom loop target binding sites are available for binding Target A while the top loop binding sites lead to self association with a second Fn3-binding molecule.

This specification describes, inter alia, the identification and production of novel, bispecific Fn3 molecules that bind to two different target molecules, e.g., HSA and VEGFR2, using both the bottom loops and top loops of the same Fn3 molecule. Hundreds of clones have been generated using the methods of the invention and one in particular, clone 89 is described in more detail in Example 6 and 7. Clone 89 is a bispecific Fn3-based binding molecule in which the bottom loops of the Fn3 molecule bind to HSA while the top loops of the same Fn3 molecule bind to VEGFR2 (SEQ ID NO: 120).

Bispecific Fn3 binding molecules can also be created by first identifying a monospecific Fn3-based binding molecule with a desired function, e.g., binding to HSA. This monospecific Fn3-based molecule only has loop variations in one of the two binding interfaces (i.e., either the top loops, or the bottom loops, but not both). Once a suitable monospecific Fn3-based binding molecule with the desired function is identified, this molecule is then used as a scaffold to generate a library in which the loops of the opposite face of the Fn3 molecule are varied, thus generating a library of bispecific Fn3-based binding molecules. This library of bispecific Fn3-based binding molecules is then used to screen against the second target molecule to identify a bispecific entity that binds to two targets. For example, the monospecific Fn3-based binding molecule can bind to HSA using at least one bottom loop. This monospecific Fn3-based binding molecule is used as a scaffold to generate a library in which at least one of the top loops of the molecule is varied such that it binds to a second target, e.g., VEGFR2, thereby creating a library of bispecific Fn3-based molecules. This library of bispecific Fn3-based molecules can be used to screen for the VEGFR2 target.

VEGFR2 is the primary mediator for the proangiogenic effects of VEGF signaling. VEGFR-2 is bound and activated by VEGF-A, VEGF-C and VEGF-D. In endothelial cells, VEGFR-2 activation stimulates cell proliferation and migration, and in vivo, VEGFR-2 activation triggers angiogenesis and increases the permeability of the vasculature. Increased angiogenesis is well established as an important feature of tumor growth and various retinopathies, while increased permeability of the vasculature is a significant event in many inflammatory responses (See e.g., WO2005056764).

This data shows that the bispecific Fn3-based binding molecules with the modified bottom loops, maintain conformational stability and can be expressed and purified while retaining binding ability. The skilled artisan will appreciate that any bispecific Fn3-based binding molecule can be generated using the methods of the invention disclosed herein. The bispecific molecule can be designed to bind to any target of interest. For example, the bispecific molecule can bind to different binding sites of the same target. Alternatively, the bispecific molecule can bind to different target molecules.

Multispecific Fn3-Based Binding Molecules

In another aspect, the invention provides multispecific Fn3-based binding molecules which comprise two or more monospecific Fn3-based binding molecules or bispecific Fn3-based binding molecules linked together (e.g., genetically or chemically). The multispecific Fn3-based binding molecules comprise at least one monomeric Fn3-based binding molecule that uses at least one of the bottom loops AB, CD, EF to bind to a target.

In one embodiment, the multispecific Fn3-based binding molecule comprises two or more Fn3-based binding molecules linked, in pearl-like fashion, wherein each individual Fn3-based binding molecule binds to a specific target. As with bispecific Fn3-based binding molecules, such targets can be present on the same molecule or on different molecules, such that the different molecules become juxtaposed by the binding of the multispecific Fn3-based binding molecule. The targets can also be identical, such that the multispecific Fn3-based binding molecule is able to cluster target molecules, in a similar way to an antibody. Avidity is also increased by binding to the same target molecule with two binding sites on the Fn3-based binding molecule capable of independently binding to different regions of the target molecule.

A variety of Fn3-based binding molecules can be incorporated into multispecific Fn3-based binding molecules, including Fn3-based binding molecules with a single binding specificity, bispecific Fn3-based binding molecules, or a combination of both types of Fn3-based binding molecules. Accordingly, suitable targets for multispecific Fn3-based binding molecules include those described above for Fn3-based binding molecules and bispecific Fn3-based binding molecules.

Multispecific Fn3-based binding molecules can be produced using art recognized methods. For example, Fn3-based binding molecules may be linked genetically, such that multispecific Fn3-based binding molecules are expressed as a single polypeptide. This linkage may be direct or conferred by an additional amino acid "linker" sequence. Suitable non-limiting methods and linkers are described, for example, in US20060286603 and WO04041862A2. Exemplary polypeptide linkers include, but are not limited to, GS linkers, such as GGGGSGGGGS (SEQ ID NO: 118), GSGSGSGSGS (SEQ ID NO: 121), PSTSTST (SEQ ID NO: 122), and EIDKPSQ (SEQ ID NO: 123), and multimers thereof. Example 6 shows how to make a multispecific Fn3-based binding molecule using a G-S linker. Specifically, the multispecific Fn3-based binding molecule is created using the GGGGSGGGGS (SEQ ID NO: 118) linker sequence that links a first monospecific Fn3-based binding molecule which binds VEGFR2 using the top loops with a second monospecific Fn3-based binding molecule which binds HSA using the bottom loops (SEQ ID NO: 119).

The multispecific Fn3-based binding molecules generated using linker sequences have an improved steric hinderance for binding to target molecules, thus enabling shorter linker sequences to be used to link two or more monomeric Fn3-based binding molecules together. Shorter linker sequences cause less immunogenic responses and are less likely to get cleaved.

Alternatively, multispecific Fn3-based binding molecules can be prepared by chemically conjugating the individual Fn3-based binding molecules using methods known in the art. A variety of coupling or cross-linking agents can be used for covalent conjugation. Examples of cross-linking agents include, e.g., protein A, carbodiimide, N-succinimidyl-5- acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. U.S.A* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.). Cysteine residues can be introduced into the Fn3-binding molecules at specific positions (See e.g.,) and then crosslink with reagents to sulfhydryl such as DPDPB or DTME (available from Pierce) to link two molecules together.

Examples 6 and 7 describe the identification and production of novel, bispecific Fn3 molecules that bind to two different targets, HSA and VEGFR2, using two separate monospecific Fn3 molecules that are linked together with a linker sequence. In this particular Example, one monomeric Fn3-based binding molecule uses the bottom loops to bind to HSA while the other monospecific Fn3-based binding molecule uses the top loops to bind VEGFR2. Hundreds of clones have been generated using the methods of the invention and a representative few have characterized, in particular clone 89. This data shows that the multispecific Fn3-based binding molecules with the modified bottom loops, maintain conformational stability and can be expressed and purified while retaining binding ability. The skilled artisan will appreciate that any number of multispecific Fn3-based binding molecules can be generated using the methods of the invention. Such multispecific binding molecules can bind to designed to bind to a single target. Alternatively, the multispecific binding molecules can bind to designed to bind to two or more targets.

Conjugates of Fn3-Based Binding Molecules

In another aspect the invention provides conjugates comprising an Fn3-based binding molecule linked to one or more non-Fn3 moieties. Such non-Fn3 moieties can, for example, impart additional functional or physiochemical properties to the Fn3-based binding molecule. In one embodiment, the Fn3-based binding molecule is linked or fused to an antibody Fc domain (or a portion thereof). Methods for fusing molecules to Fc domains, e.g., the Fc domain of IgG1, are known in the art (see, e.g., U.S. Pat. No. 5,428,130). Such conjugates have increased circulating half-lives, due to the ability of Fc to bind to FcRn, which serves a critical function in IgG homeostasis, protecting molecules bound to it from catabolism.

In another embodiment, Fn3-based binding molecule is fused to one or more human serum albumin (HSA) polypeptides, or a portion thereof. HSA, a protein of 585 amino acids in its mature form, is responsible for a significant proportion of the osmotic pressure of serum and also functions as a carrier of endogenous and exogenous ligands. The role of albumin as a carrier molecule and its inert nature are desirable properties for use as a carrier and transporter of polypeptides in vivo. The use of albumin as a component of an albumin fusion protein as a carrier for various proteins has been suggested in WO 93/15199, WO 93/15200, and EP 413 622. The use of N-terminal fragments of HSA for fusions to polypeptides has also been proposed (EP 399 666). Accordingly, by genetically or chemically fusing or conjugating the molecules of the present invention to albumin, or a fragment (portion) or variant of albumin or a molecule capable of binding HSA (an "anti-HSA binder") that is sufficient to stabilize the protein and/or its activity, the molecule is stabilized to extend the shelf-life, and/or to retain the molecule's activity for extended periods of time in solution, in vitro and/or in vivo.

Fusion of albumin to another protein may be achieved by genetic manipulation, such that the DNA coding for HSA, or a fragment thereof, is joined to the DNA coding for the protein. A suitable host is then transformed or transfected with the fused nucleotide sequences, so arranged on a suitable plasmid as to express a fusion polypeptide. The expression may be effected in vitro from, for example, prokaryotic or eukaryotic cells, or in vivo e.g. from a transgenic organism. Additional methods pertaining to HSA fusions can be found, for example, in WO 2001077137 and WO 200306007, incorporated herein by reference. In a specific embodiment, the expression of the fusion protein is performed in mammalian cell lines, for example, CHO cell lines.

Other Fn3-based binding molecule conjugates of the present invention include an Fn3-based binding molecule linked to a non-Fn3-based binding molecule, e.g., another peptide or protein (e.g., an antibody or ligand for a receptor), to generate a molecule that binds to at least two different binding sites or target molecules.

The Fn3-based binding molecule conjugates of the present invention can be prepared by linking the constituent molecules using methods known in the art. For example, the constituent molecules can be chemically linked using a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. U.S.A* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

Alternatively, the constituent molecules can be encoded in the same vector and expressed as a single protein in a host cell. Methods for producing such fusion proteins are described, for example, in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

In yet another embodiment, the invention provides Fn3-based binding molecules that are conjugated to polyethylene glycol (PEG), for example, to increase the biological (e.g., serum) half-life of the molecule. Methods for PEGylating proteins are well known in the art. For example, the Fn3-based binding molecule can be reacted with a PEG moiety, such as a reactive ester or aldehyde derivative of PEG, under conditions in which one or more PEG groups become attached to the molecule. The term "PEGylation moiety", "polyethylene glycol moiety", or "PEG moiety" includes a polyalkylene glycol compound or a derivative thereof, with or without coupling agents or derivatization with coupling or activating moieties (e.g., with thiol, triflate, tresylate, aziridine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types:

dextran, colominic acids, or other carbohydrate based polymers, polymers of amino acids, and biotin derivatives.

The choice of the suitable functional group for the PEG derivative is based on the type of available reactive group on the molecule or molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. Methods for pegylating proteins are known in the art and can be applied to the present invention. See for example, WO 2005056764, U.S. Pat. No. 7,045,337, U.S. Pat. No. 7,083,970, U.S. Pat. No. 6,927,042, EP 0 154 316 by Nishimura et al. and EP 0 401 384 by Ishikawa et al. Fn3-based binding molecules can be engineered to include at least one cysteine amino acid or at least one non-natural amino acid to facilitate pegylation.

Binding of the Fn3-based binding molecule conjugates to their specific targets can be confirmed by various assays, for example, the fusion can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ-counter or a scintillation counter or by autoradiography.

Other Fn3-based binding molecule conjugates of the present invention include an Fn3-based binding molecule linked to a tag (e.g., biotin) or a chemical (e.g., an immunotoxin or chemotherapeutic agent). Such chemicals include cytotoxic agent which is any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be conjugated to Fn3-based binding molecule of the invention include duocarmycins, calicheamicins, maytansines and auristatins, and derivatives thereof.

Cytotoxins can be conjugated to the Fn3-based binding molecules of the invention using linker technology available in the art. Examples of linker types that have been used to conjugate a cytotoxin include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Fn3-based binding molecules of the present invention also can be conjugated to a radioactive isotope to generate cytotoxic radiopharmaceuticals, also referred to as radioimmunoconjugates. Examples of radioactive isotopes that can be conjugated to Fn3-based binding molecules for use diagnostically or therapeutically include, but are not limited to, iodine$^{131}$, indium$^{111}$, yttrium$^{90}$ and lutetium$^{177}$. Methods for preparing radioimmunoconjugates are established in the art. Examples of radioimmunoconjugates are commercially available, including ibritumomab, tiuxetan, and tositumomab, and similar methods can be used to prepare radioimmunoconjugates using the molecules of the invention.

The Fn3-based binding molecule conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety are well known and can be applied to the molecules of the present invention, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Fn3-based binding molecules of the present invention also can be modified by hesylation, which utilizes hydroxyethyl starch ("HES") derivatives linked to drug substances in order to modify the drug characteristics. HES is a modified natural polymer derived from waxy maize starch which is metabolized by the body's enzymes. This modification enables the prolongation of the circulation half-life by increasing the stability of the molecule, as well as by reducing renal clearance, resulting in an increased biological activity. Furthermore, HESylation potentially alters the immunogenicity or allergenicity. By varying different parameters, such as the molecular weight of HES, a wide range of HES drug conjugates can be customized.

DE 196 28 705 and DE 101 29 369 describe possible methods for carrying out the coupling of hydroxyethyl starch in anhydrous dimethyl sulfoxide (DMSO) via the corresponding aldonolactone of hydroxyethyl starch with free amino groups of hemoglobin and amphotericin B, respectively. Since it is often not possible to use anhydrous, aprotic solvents specifically in the case of proteins, either for solubility reasons or else on the grounds of denaturation of the proteins, coupling methods with HES in an aqueous medium are also available. For example, coupling of hydroxyethyl starch which has been selectively oxidized at the reducing end of the chain to the aldonic acid is possible through the mediation of water-soluble carbodiimide EDC (1-ethyl-3-(3-dimethyl-aminopropyl)carbodiimide) (PCT/EP 02/02928). Additional hesylation methods which can be applied to the present invention are described, for example, in U.S. 20070134197, U.S. 20060258607, U.S. 20060217293, U.S. 20060100176, and U.S. 20060052342.

Fn3-based binding molecules of the invention also can be modified via sugar residues. Methods for modifying sugar residues of proteins or glycosylating proteins are known in the art (see, for example, Borman (2006) Chem. & Eng. News 84(36):13-22 and Borman (2007) Chem. & Eng. News 85:19-20) and can be applied to the molecules of the present invention.

Additionally or alternatively, Fn3-based binding molecules of the invention can be made that have an altered type of glycosylation, such as a hypofucosylated pattern having reduced amounts of fucosyl residues or an Fn3-based binding molecule having increased bisecting GlcNac structures. Such carbohydrate modifications can be accomplished by, for example, expressing the Fn3-based binding molecule in a host cell with altered glycosylation machinery. Cells with altered glycosylation machinery have been described in the art and can be used as host cells in which to express recombinant Fn3-based binding molecules of the invention to thereby produce Fn3-based binding molecules of the invention with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). Methods to produce polypeptides with human-like glycosylation patterns have also been described by EP1297172B1 and other patent families originating from Glycofi.

Methods for Generating Fn3-Based Binding Molecules

1) Nucleic Acid and Amino Acid Alterations

Fn3-based binding molecules of the invention having one or more amino acid or nucleotide modifications (e.g., alterations) can be generated by a variety of known methods. Typically, such Fn3-based binding modified molecules are produced by recombinant methods. Moreover, because of the degeneracy of the genetic code, a variety of nucleic acid sequences can be used to encode each desired molecule.

Exemplary art recognized methods for making a nucleic acid molecule encoding an amino acid sequence variant of a starting molecule include, but are not limited to, preparation by site-directed (or oligonucleotide-mediated) mutagenesis, PCR mutagenesis, and cassette mutagenesis of an earlier prepared DNA encoding the molecule.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. U.S.A 82:488 (1987)). Briefly, in carrying out site-directed mutagenesis of DNA, the parent DNA is altered by first hybridizing an oligonucleotide encoding the desired mutation to a single strand of such parent DNA. After hybridization, a DNA polymerase is used to synthesize an entire second strand, using the hybridized oligonucleotide as a primer, and using the single strand of the parent DNA as a template. Thus, the oligonucleotide encoding the desired mutation is incorporated in the resulting double-stranded DNA.

PCR mutagenesis is also suitable for making amino acid sequence variants of the starting molecule. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the parent DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a polypeptide variant of the molecule can be determined, and a nucleic acid sequence encoding such amino acid sequence variant can be generated synthetically.

It will be understood by one of ordinary skill in the art that the Fn3-based binding molecules of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, i.e., a conservative substitutions, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Aside from amino acid substitutions, the present invention contemplates other modifications of the starting molecule amino acid sequence in order to generate functionally equivalent molecules. For example, one may delete one or more amino acid residues. Generally, no more than one to about ten residues will be deleted according to this embodiment of the invention. The Fn3-based binding molecules comprising one or more amino acid deletions will preferably retain at least about 80%, and preferably at least about 90%, and most preferably at least about 95%, of the starting polypeptide molecule.

One may also make amino acid insertion variants, which retain the original Fn3 domain or Fn3-based binding molecule functionality. For example, one may introduce at least one amino acid residue (e.g. one to two amino acid residues and generally no more than ten residues) into the molecule. In another embodiment amino acid modifications may be combined within an Fn3 domain or single Fn3-based binding molecules.

In one embodiment, amino acid substitutions are performed on an Fn3 domain to include cysteine or other non-natural amino acid suitable for conjugating a moiety to the Fn3-based binding molecule using well-known conjugating methods. In particular, the invention relates to specific amino acid variants of Fn3-based binding molecule with Fn3 scaffold, wherein one or more serine amino acid residues are substituted by cysteine or a non-natural amino acid. Serine amino acid residues that can substituted include, but are not limited to Ser 1432, Ser 1436, Ser 1458, Ser 1475, and Ser 1504. Other amino acid positions of the Fn3 scaffold that can be substituted include, but are not limited to, V1426, L1434, T1473 and T1486. Non-naturally occurring amino acids can be substituted into the Fn3 scaffold using, for example, Ambrex technology (See e.g., U.S. Pat. Nos. 7,045,337; 7,083,970).

2) Screening Assays for Identifying Fn3-Based Binding Molecules

A variety of screening assays can be employed to identify Fn3-based binding molecules of the invention. Essentially any in vitro or in vivo screening method that selects for binding to a desired antigen can be used.

In one embodiment, Fn3-based binding molecules are displayed on the surface of a cell, virus or bacteriophage and subject to selection using immobilized antigen. Suitable methods of screening are described in U.S. Pat. Nos. 7,063,943; 6,699,658; 7,063,943 and 5,866,344. Such surface display may require the creation of fusion proteins of the Fn3-based binding molecules with a suitable protein normally present on the outer surface of a cell, virus or bacteriophage. Suitable proteins from which to make such fusions are well known in the art.

In another embodiment, Fn3-based binding molecules are screened using an in vitro phenotype-genotype linked display such as ribosome or polysome display. Such methods of "molecular evolution" are well known in the art (see for example U.S. Pat. Nos. 6,194,550 and 7,195,880).

Screening methods may involve one or more in vitro or in vivo affinity maturation steps. Any affinity maturation approach can be employed that results in amino acid changes in the Fn3 domain or the CDRs that improve the binding of the Fn3-based binding molecule to the desired antigen. These amino acid changes can, for example, be achieved via random mutagenesis, "walk though mutagenesis, and "look through mutagenesis. Such mutagenesis can be achieved by using, for example, error-prone PCR, "mutator" strains of yeast or bacteria, incorporation of random or defined nucleic acid changes during ab inito synthesis of all or part of a Fn3-based binding molecule. Methods for performing affinity maturation and/or mutagenesis are described, for example, in U.S. Pat. Nos. 7,195,880; 6,951,725; 7,078,197; 7,022,479; 5,922,545; 5,830,721; 5,605,793, 5,830,650; 6,194,550; 6,699,658; 7,063,943; 5,866,344 and Patent Cooperation Treaty publication WO06023144. Such affinity maturation methods may further require that the stringency of the antigen-binding screening assay is increased to select for Fn3-based binding molecules with improved affinity for antigen. Art recognized methods for increasing the stringency of a protein-protein interaction assay can be used here. In one embodiment, one or more of the assay conditions are varied (for example, the salt concentration of the assay buffer) to reduce the affinity of the Fn3-based binding molecules for the desired antigen. In another embodiment, the length of time permitted for the Fn3-based binding molecules to bind to the desired antigen is reduced. In another embodiment, a competitive binding step is added to the protein-protein interaction assay. For example, the Fn3-based binding molecules are first allowed to bind to a desired immobilized antigen. A specific concentration of non-immobilized antigen is then added which serves to compete for binding with the immobilized antigen such that the Fn3-based binding molecules with the lowest affinity for antigen are eluted from the immobilized antigen resulting in selection of Fn3-based binding molecules with improved antigen binding affinity. The stringency of the assay conditions can be further increased by increasing the concentration of non-immobilized antigen is added to the assay.

Screening methods of the invention may also require multiple rounds of selection to enrich for one or more Fn3-based binding molecules with improved antigen binding. In one embodiment, at each round of selection further amino acid mutation are introduce into the Fn3-based binding molecules. In another embodiment, at each round of selection the stringency of binding to the desired antigen is increased to select for Fn3-based binding molecules with increased affinity for antigen.

In the case of the bispecific Fn3-based binding molecules of the invention, it is preferable to screen for each binding specificity independently. Accordingly, a first screen to identify individual Fn3-based binding molecules, that bind to a first target, is performed using a first library of Fn3-based binding molecules, where one or more amino acids in one or more of the AB, CD or EF loops is altered. A second separate screen to identify individual Fn3-based binding molecules, that bind to a second target, is performed using a second library of Fn3 domain molecules, where one or more amino acids in one or more of the BC, DE and FG loops is altered. The amino acid sequences of the individual monospecific Fn3-based binding molecules identified from both screens are determined using art recognized methods. Bispecific Fn3-based binding molecules are generated by combining first and second target-binding sequences from individual Fn3-based binding molecules into single, chimeric Fn3-based binding molecules.

3) Methods of Manufacture

The Fn3-based binding molecules of the invention are typically produced by recombinant expression. Nucleic acids encoding the molecules are inserted into expression vectors. The DNA segments encoding the molecules are operably linked to control sequences in the expression vector(s) that ensure their expression. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting Fn3-based binding molecule.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilis*, and other enterobacteriaceae, such as *Salmonella, Serratia*, and various *Pseudomonas* species.

Other microbes, such as yeast, are also useful for expression. *Saccharomyces* and *Pichia* are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

In addition to microorganisms, mammalian tissue culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various COS cell lines, HeLa cells, 293 cells, myeloma cell lines, transformed B-cells, and hybridomas. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

Alternatively, coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest and expression control sequences can be transferred into the host cell by well-known methods, which vary depending on the type of cellular host. For example, chemically competent prokaryotic cells may be briefly heat-shocked, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, the Fn3-based binding molecules of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure molecules of at least about 90 to 95% homogeneity are preferred, and 98 to 99% or more homogeneity most preferred, for pharmaceutical uses.

4) Methods for Grafting CDRs onto Fn3-Based Binding Molecules

In one aspect, the present invention features an Fn3-based binding molecule altered compared to the wild-type Fn3 domain to contain all or a portion of a complementarity determining region (CDR) of an antibody or a T-cell receptor.

The CDR regions of any antibody or T-cell receptor variable region, or antigen binding fragments thereof, are suitable for grafting. The CDRs can be obtained from the antibody or T-cell receptor repertoire of any animal including, but not limited to, rodents, primates, camelids or sharks. In a particular embodiment, the CDRs are obtained from CDR1, CDR2 and CDR3 of a single domain antibody, for example a nanobody. In a more specific embodiment, CDR1, 2 or 3 of a single domain antibody, such as a nanobody, are grafted into any of the AB, BC, CD, DE, EF or FG loops of an Fn3 domain, thereby providing target binding specificity of the original nanobody to the Fn3-based binding molecule. Engineered libraries of camelid antibodies and antibody fragments are commercially available, for example, from Ablynx, Ghent, Belgium. The antibody repertoire can be from animals challenged with one or more antigens or from naïve animals that have not been challenged with antigen. Additionally or alternatively, CDRs can be obtained from antibodies, or antigen binding fragments thereof, produced by in vitro or in vivo library screening methods, including, but not limited to, in vitro polysome or ribosome display, phage display or yeast display techniques. This includes antibodies not originally generated by in vitro or in vivo library screening methods but which have subsequently undergone mutagenesis or one or more affinity maturation steps using in vitro or in vivo screening methods. Example of such in vitro or in vivo library screening methods or affinity maturation methods are described, for example, in U.S. Pat. Nos. 7,195,880; 6,951,725; 7,078,197; 7,022,479; 5,922,545; 5,830,721; 5,605,793, 5,830,650; 6,194,550; 6,699,658; 7,063,943; 5,866,344 and Patent Cooperation Treaty publications WO06023144.

Methods to identify antibody CDRs are well known in the art (see Kabat et al., U.S. Dept. of Health and Human Services, "Sequences of Proteins of Immunological Interest" (1983); Chothia et al., J. Mol. Biol. 196:901-917 (1987); MacCallum et al., J. Mol. Biol. 262:732-745 (1996)). The nucleic acid encoding a particular antibody can be isolated and sequenced, and the CDR sequences deduced by inspection of the encoded protein with regard to the established antibody sequence nomenclature. Methods for grafting hypervariable regions or CDRs into a Fn3-based binding scaffold of the invention include, for example, genetic engineering, de novo nucleic acid synthesis or PCR-based gene assembly (see for example U.S. Pat. No. 5,225,539).

The above techniques allow for the identification of a suitable scaffold loop for selection and presentation of a hypervariable region or CDR. However, additional metrics can be invoked to further improve the fit and presentation of the hypervariable region based on structural modeling of the Fn3 domain and the donor antibody.

In one aspect, specific amino acid residues in any of the beta-strands of an Fn3 domain are mutated to allow the CDR loops to adopt a conformation that retains or improves binding to antigen. This procedure can be performed in an analogous way to that CDR grafting into a heterologous antibody framework, using a combination of structural modeling and sequence comparison. In one embodiment, the Fn3 domain residues adjacent to a CDR are mutated in a similar manner to that performed by Queen et al. (see U.S. Pat. Nos. 6,180,370; 5,693,762; 5,693,761; 5,585,089; 7,022,500). In another embodiment, Fn3 domain residues within one Van der Waals radius of CDR residues are mutated in a similar manner to that performed by Winter et al. (see U.S. Pat. Nos. 6,548,640; 6,982,321). In another embodiment, Fn3 domain residues that are non-adjacent to CDR residues but are predicted, based upon structural modeling of the Fn3 domain and the donor antibody, to modify the conformation of CDR residues are mutated in a similar manner to that performed by Carter et al. or Adair et al. (see U.S. Pat. Nos. 6,407,213; 6,639,055; 5,859,205; 6,632,927).

Compositions

The Fn3-based binding of the present invention have in vivo therapeutic utilities. Accordingly, the present invention also provides compositions, e.g., a pharmaceutical composition, containing one or a combination of Fn3-based binding molecules (or variants, fusions, and conjugates thereof), formulated together with a pharmaceutically acceptable carrier. Pharmaceutical compositions of the invention also can be administered in combination therapy, i.e., combined with other agents. For example, the combination therapy can include a composition of the present invention with at least one or more additional therapeutic agents, such as anti-inflammatory agents, anti-cancer agents, and chemotherapeutic agents.

The pharmaceutical compositions of the invention can also be administered in conjunction with radiation therapy. Co-administration with other Fn3-based molecules are also encompassed by the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, bio compatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the Fn3-based binding molecule of the invention may be administered once or twice weekly by subcutaneous injection or once or twice monthly by subcutaneous injection. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the molecules of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

In a further embodiment, the molecules of the invention can be formulated to prevent or reduce the transport across the placenta. This can be done by methods known in the art, e.g., by PEGylation of the Fn3-based binding molecule. Further references can be made to "Cunningham-Rundles C, Zhuo Z, Griffith B, Keenan J. (1992) Biological activities of polyethylene-glycol immunoglobulin conjugates. Resistance to enzymatic degradation. J Immunol Methods. 152:177-190; and to "Landor M. (1995) Maternal-fetal transfer of immunoglobulins, Ann Allergy Asthma Immunol 74:279-283. This is particularly relevant when the Fn3-based binding molecule are used for treating or preventing recurrent spontaneous abortion.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Therapeutic and Diagnostic Applications

The Fn3-based binding molecules described herein may be constructed to bind any antigen or target of interest. Such targets include, but are not limited to, cluster domains, cell receptors, cell receptor ligands, growth factors, interleukins, protein allergens, bacteria, or viruses (see, FIG. 1). The Fn3-based binding molecules described herein may also be modified to have increased stability and half-life, as well as additional functional moieties. Accordingly, these molecules may be employed in place of antibodies in all areas in which antibodies are used, including in the research, therapeutic, and diagnostic fields. In addition, because these molecules possess solubility and stability properties superior to antibodies, the antibody mimics described herein may also be used under conditions which would destroy or inactivate antibody molecules.

For example, these molecules can be administered to cells in culture, e.g. in vitro or ex vivo, or in a subject, e.g., in vivo, to treat, prevent or diagnose a variety of disorders. The term "subject" as used herein in intended to includes human and non-human animals. Non-human animals includes all vertebrates, e.g., mammals and non-mammals, such as non-human primates, sheep, dogs, cats, cows, horses, chickens, amphibians, and reptiles. When the Fn3 molecules are administered together with another agent, the two can be administered in either order or simultaneously.

In one embodiment, the Fn3-based binding molecules (and variants, fusions, and conjugates thereof) of the invention can be used to detect levels of the target bound by the molecule and/or the targets bound by a bispecific/multispecific Fn3-based binding molecule. This can be achieved, for example, by contacting a sample (such as an in vitro sample) and a control sample with the molecule under conditions that allow for the formation of a complex between the molecule and the target(s). Any complexes formed between the molecule and the target(s) are detected and compared in the sample and the control. For example, standard detection methods, well-known in the art, such as ELISA, FACS, and flow cytometric assays, can be performed using the compositions of the invention.

Also within the scope of the invention are kits comprising the compositions (e.g., Fn3-based binding molecules, variants, fusions, and conjugates thereof) of the invention and instructions for use. The kit can further contain a least one additional reagent, or one or more additional Fn3-based binding molecules of the invention (e.g., an antibody having a complementary activity which binds to an epitope on the target antigen distinct from the first molecule). Kits typically include a label indicating the intended use of the contents of the kit. The term label includes any writing, or recorded material supplied on or with the kit, or which otherwise accompanies the kit.

As described above, the molecules of the present invention may be employed in all areas of the research, therapeutic, and diagnostic fields. Exemplary diseases/disorders which can be treated using the Fn3-based binding molecules of the present invention (and variants, fusions, and conjugates thereof) include autoimmune disorders, cancers, infections, and other pathogenic indications.

Specific examples of autoimmune conditions in which the Fn3-based binding molecules of the invention can be used include, but are not limited to, the following: multiple sclerosis and other demyelinating diseases; rheumatoid arthritis; inflammatory bowel disease; systemic lupus erythematosus; Type I diabetes; inflammatory skin disorders; Sjogren's Syndrome; and transplant rejection.

Specific examples of cancers in which the Fn3-based binding molecules of the invention can be used include, but are not limited to, the following: lung; breast; prostate; bladder; melanoma; non-Hodgkin lymphoma; colon and rectal; pancreatic; endometrial; kidney; skin (non-melanoma); leukemia; and thyroid.

Specific examples of diseases associated with VEGF include for example, a number of conditions associated with inappropriate angiogenesis, including but not limited to autoimmune disorders (e.g., rheumatoid arthritis, inflammatory bowel disease or psoriasis); cardiac disorders (e.g., atherosclerosis or blood vessel restenosis); retinopathies (e.g., proliferative retinopathies generally, diabetic retinopathy, age-related macular degeneration or neovascular glaucoma), renal disease (e.g., diabetic nephropathy, malignant nephrosclerosis, thrombotic microangiopathy syndromes; transplant rejection; inflammatory renal disease; glomerulonephritis; mesangioproliferative glomerulonephritis; haemolytic-uraemic syndrome; and hypertensive nephrosclerosis); hemangioblastoma; hemangiomas; thyroid hyperplasias; tissue transplantations; chronic inflammation; Meigs's syndrome; pericardial effusion; pleural effusion; autoimmune diseases; diabetes; endometriosis; chronic asthma; undesirable fibrosis (particularly hepatic fibrosis) and cancer, as well as complications arising from cancer, such as pleural effusion and ascites. The Fn3-based binding molecules can be used for the treatment of prevention of hyperproliferative diseases or cancer and the metastatic spread of cancers. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer. Additional treatable conditions can be found in U.S. Pat. No. 6,524,583, herein incorporated by reference. Other references describing uses for VEGFR-2 binding polypeptides include: McLeod D S et al., Invest Ophthalmol V is Sci. 2002 February; 43(2):474-82; Watanabe et al. Exp Dermatol. 2004 November; 13(11):671-81; Yoshiji H et al., Gut. 2003 September; 52(9): 1347-54; Verheul et al., Oncologist. 2000; 5 Suppl 1:45-50; Boldicke et al., Stem Cells. 2001; 19(1):24-36. As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis (see e.g., WO2005056764).

Specific examples of infections in which the Fn3-based binding molecules of the invention can be used include, but are not limited to, the following: cellular, fungal, bacterial, and viral.

The present invention is further illustrated by the following examples which should not be construed as further limiting. The contents of all figures and all references, patents and published patent applications cited throughout this application are expressly incorporated herein by reference.

EXEMPLIFICATION

Example 1

Production of Libraries of Fibronectin-Based Binding Molecules

In general, the practice of the present invention employs, unless otherwise indicated, conventional techniques of chemistry, molecular biology, recombinant DNA technology, immunology (especially, e.g., antibody technology), and standard techniques in polypeptide preparation. See, e.g., Sambrook, Fritsch and Maniatis, *Molecular Cloning Cold Spring Harbor Laboratory Press* (1989); *Antibody Engineering Protocols* (*Methods in Molecular Biology*), 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C. S. H. L. Press, Pub. (1999); and *Current Protocols in Molecular Biology*, eds. Ausubel et al., John Wiley & Sons (1992). Other methods, techniques, and sequences suitable for use in carrying out the present invention are found in U.S. Pat. Nos. 7,153,661; 7,119,171; 7,078,490; 6,703,199; 6,673,901; and 6,462,189.

The 10th human fibronectin protein (Fn3$^{10}$) was used to design, isolate, and engineer monospecific binders. Initial binders were first independently isolated from two libraries using standard selection methods. This enriched population was then mutagenized, and successive rounds of random mutagenesis and enrichment were conducted to attain desired monospecific binders.

Library Construction

Wildtype Fn3$^{10}$ sequence as shown in SEQ ID NO: 1 was used as the basis to generate libraries of binders that utilize the top or bottom loops.

```
                                            (SEQ ID NO: 1)
VSDVPRDLEVVAATPTSLLISWDAPAVTVRYYRITYGETGGNSPVQEF

TVPGSKSTATISGLKPGVDYTITVYAVTGRGDSPASSKPISINYRTEI
```

Using computational modeling, two sets of variable regions of the wildtype Fn3$^{10}$ were chosen to be randomized. The first set comprising the solvent exposed top loops BC, DE and FG was designated library A and was randomized in the region shown in boldface in SEQ ID NO: 2.

Library A (beta-sandwich with solvent exposed top loops BC, DE and FG).

```
                                            (SEQ ID NO: 2)
VSDVPRDLEVVAATPTSLLISWDAPAVTVRYYRITYGETGGNSPVQEF

TVPGSKSTATISGLKPGVDYTITVYAVTGRGDSPASSKPISINYRTEI
```

The second set comprising the solvent exposed bottom loops AB, CD, EF and C-terminus was designated library B and was randomized in the underlined regions shown in italics.

Library B (beta-sandwich with solvent exposed bottom loops AB, CD, EF and C-terminus).

```
                                            (SEQ ID NO: 3)
VSDVPRDLEVVAAT_PTS_LLISWDAPAVTVRYYRITYG_ETGGNSPV_QEF

TVPGSKSTATI_SGLKPG_VDYTITVYAVTGRGDSPASSKPISINY_RTEI_
```

The DNA sequences corresponding to the two libraries were optimised for expression in *E. coli* at Geneart AG, Germany. Regions in boldface or underlined italics from SEQ ID NOs: 2 and 3, respectively, were synthesized as degenerated positions. The libraries were assembled from synthetic degenerated oligonucleotides and genes corresponding to full length fragments gel purified. Amplification was performed with terminal primers and subsequent ligation of the amplified library into cloning vector pCR-Script yielded the starting libraries. Libraries A and B were then independently screened to identify monospecific binders as described in Example 2 below.

Example 2

Screening of Monospecific Fibronectin-Based Binding Molecules

The present Example describes how to screen for fibronectin monospecific binders generated from the Libraries A and B described in Example 1. Both libraries A and B were independently subcloned into a yeast display vector such as pYD1 (Invitrogen) using homologous recombination methods and transformed into a suitable strain such as EBY100 using standard molecular biology techniques.

Presentation and selection of fibronectin based binders against hen egg lysozyme was conducted following essentially the protocol previously published by Lipovsek, D. et al, (J Mol Biol. 2007 May 11; 368(4):1024-41) with some minor modifications. Both libraries were independently screened for binders to hen egg white lysozyme.

(i) Selection for Binding to Hen Egg White Lysozyme Using Magnetic Bead Sorting

For all selections, yeast cultures presenting library A or library B of $^{10}$Fn3-based molecules were induced for 18 h at 30° C. in galactose-containing medium (90% SG-CAA/10% SD-CAA, 50 µg/mL kanamycin, 100 U/mL penicillin G, 200 U/mL streptomycin). $10^9$ induced yeast cells of libraries A or B were washed with 25 mL of ice-cold phosphate-buffered saline (PBS), pH 7.4, 2 mM ethylenediaminetetraacetic acid (EDTA), 0.5% bovine serum albumin (BSA) and then incubated in 5 mL of the same buffer containing 1 µM biotinylated hen egg white lysozyme (HEL-b, Sigma, St. Louis, Mo.) for 1 h at room temperature with gentle rotation. Following the incubation, the sample was chilled on ice, washed with 25 mL of ice-cold PBS, pH 7.4, 2 mM EDTA, 0.5% BSA and resuspended in 2.5 mL of the same buffer. 100 µL aliquot of magnetic Streptavidin MicroBeads (Miltenyi Biotec, Auburn, Calif.) was added to the yeast and incubated on ice for 10 min. Ice-cold PBS, pH 7.4, 2 mM EDTA, 0.5% BSA was added to the sample to a total volume of 25 mL immediately before it was subjected to separation on an AutoMACS Cell Separator (Miltenyi Biotec), using the preset program for positive selection of rare cells (possel_s). Selected cells were collected in 6 mL SD-CAA, pH 4.5, 50 µg/mL kanamycin, 100 U/mL penicillin G, 200 U/mL streptomycin; quantified by serial dilution followed by plating on SD-CAA agar plates; and grown in 50 mL of the same medium for 2 days at 30° C.

(ii) Selection for Binding to Hen Egg White Lysozyme Using Fluorescence-Activated Cell Sorting Subsequent rounds of selection were performed by FACS, starting with $2 \times 10^6$ to $3 \times 10^6$ induced yeast cells. Cells were washed with 1 mL PBS, pH 7.4, 0.1% BSA, resuspended in 100 µL of the same buffer containing biotinylated hen egg white lysozyme, and incubated at room temperature with gentle rotation for 1 h.

After being washed with 1 mL of ice-cold PBS, pH 7.4, 0.1% BSA, the cells were labeled with antibodies and streptavidin. Mouse monoclonal FITC-conjugated anti-c-myc antibody (AbD Serotec) was used to label the yeast for surface display of c-myc-tagged antibody mimics, and PE-labeled streptavidin (Invitrogen) or anti-biotin antibody (Miltenyi) was used to label HEL-b associated with lysozyme-binding antibody mimics. The FACS sorts were performed on yeast cells labeled with FITC-conjugated mouse anti-c-myc antibody and PE-conjugated streptavidin (Invitrogen).

Double-labeled yeast cells were sorted on a Dako MoFlo high-speed cell sorter with a 488 nm laser, at 6000-10,000 cells/s. Gates were adjusted to collect the yeast cells with the highest 0.1-1% of HEL-b-associated signal (PE) and in the top half of expression-associated signal (FITC). Duplicate samples labeled with the same antibody and streptavidin reagents, but in the absence of HEL-b were used to avoid selecting the cells that bound detection reagents instead of lysozyme.

For all libraries, the first two FACS sorts were performed on yeast labeled with 1 µM HEL-b. Once a population of cells was observed that was labeled with PE in the presence but not in the absence of HEL-b, the concentration of HEL-b in the subsequent round was decreased by an order of magnitude. Selected cells were collected in 0.5 mL of SD-CAA, pH 4.5, 50 µg/mL kanamycin, 100 U/mL penicillin G, and 200 U/mL streptomycin. The collected cells were grown to saturation in 5 mL of the same medium, with shaking, for 2 days at 30° C., before being induced and labeled for the next round of sorting.

After several rounds of FACS sorting the final enriched population was plated out on SDCAA plates and incubated at 30° C. for 2 days. Individual colonies were picked using a Genetix Clonepix and re-arrayed into 96 well plates containing SD-CAA medium. After incubation for 24 hours the cells were collected by centrifugation and re-suspended in SD-GAA medium for induction of surface expressed unique Fn3 molecules. Positive clones were identified by standard ELISA. Plasmid DNA corresponding to the unique Fn3 positive clones was purified and sequenced to identify monospecific binders.

Once monospecific binders were identified and selected from either libraries A or B, they can be used independently to generate therapeutic molecules. In particular, the monospecific binders generated from library B using the bottom loops of the Fn3 molecule can be used to generate novel therapeutic binding molecules against a target of interest. Various monospecific binders from library B can be combined with linkers to produce a Fn3 binding molecule that is capable of binding to one or more regions of a single target (e.g., TNF). Alternately, a Fn3 binding molecule comprising binders from Library B can also be designed to bind to one or more regions of multiple targets (e.g., one or more regions of HSA and TNF).

In addition, the monospecific binders generated from Library A and Library B can be combined using standard molecular biology technique to generate bispecific and multispecific binders as described in Example 3 below.

Example 3

Generation of Bifunctional Fibronectin-Based Binding Molecules

Computer modeling of the randomized regions onto the x-ray structure of human Fn3 shows that by combining monospecific binders of each of the libraries A and B, one can create a bispecific fibronectin binding molecules. These binding molecules can be engineered such that they recognizes different regions on the same target molecule, or that the different binding sites of the bispecific or multispecific fibronectin molecule can bind to different regions on two or more different targets.

For example, a suitable sequence corresponding to binder A (obtained by screening Library A) and a suitable sequence corresponding to binder B (obtained by screening library B) can be combined into one single molecule to generate a bispecific molecule.

Binder A identified by screening library A (beta-sandwich with solvent exposed top loops BC, DE and FG).

(SEQ ID NO: 4)
VSDVPRDLEVVAATPTSLLISWXXXXXXXRYYRITYGETGGNSPVQEF

TVPXXXXTATISGLKPGVDYTITVYAVTXXXXXXXXXXPISINYRTEI where X is any amino acid sequence.

Binder B identified by screening library B (beta-sandwich with solvent exposed bottom loops AB, CD, EF and C-terminus).

(SEQ ID NO: 5)
VSDVPRDLEVVAAT_ZZ_SLLISWDAPAVTVRYYRITYG_ZZZZZZZ_VQEF

TVPGSKSTATI_ZZZZZ_GZDYTITVYAVTGRGDSPASSKPISINY_ZT_ZZ where Z is any amino acid sequence.

Binder C identified by combining sequences obtained by screening library A (beta-sandwich with solvent exposed top loops BC, DE and FG) and B (beta-sandwich with solvent exposed top loops BC, DE and FG). Merging of the two sequences into one molecule leads to the bispecific Binder C.

(SEQ ID NO: 6)
VSDVPRDLEVVAAT_ZZ_SLLISWXXXXXXXRYYRITYG_ZZZZZZZ_VQEF

TVPXXXXTATI_ZZZZZ_GZDYTITVYAVTXXXXXXXXXXPISINY_ZT_ZZ

Where X and Z are any amino acid sequences.

The DNA corresponding to the combined aminoacid sequence of Binder C is then synthesized and optimised for expression in *E. coli* at Geneart AG, Germany. Cloning into *E. coli* and subsequent purification follows standard protocols as outlined in chapter 4 (Methods of manufacture).

Alternatively, a bifunctional Fn3-based binding molecule an be generated by linking two or more monospecific Fn3-based binding molecules.

Example 4

Generation of Monospecific Fibronectin-Based Binding Molecules that use the Bottom Loops to Bind a Target The experimental details described in Example 2 were repeated to generate monospecific Fn3-based binding molecules that use the bottom loops of fibronectin to bind to the half-life extender, HSA. A separate library was used to generate monospecific Fn3-based binding molecules that use the bottom loops to bind to lyzozyme.

(a) Isolating of the Enriched Pool from Yeast

Sequences of selected populations were determined after several rounds of selection. Plasmid DNA was extracted from 1 mL of saturated culture of each selected yeast population using a Zymoprep kit (Zymo Research, Orange, Calif.), and 2 µL of the plasmid was transformed into electro-competent Top10 *E. coli* (Invitrogen, Carlsbad, Calif.). Plasmid minipreps were prepared and sequenced for 96 colonies.

(b) Sub-Cloning into *E. coli*

Figure 6:
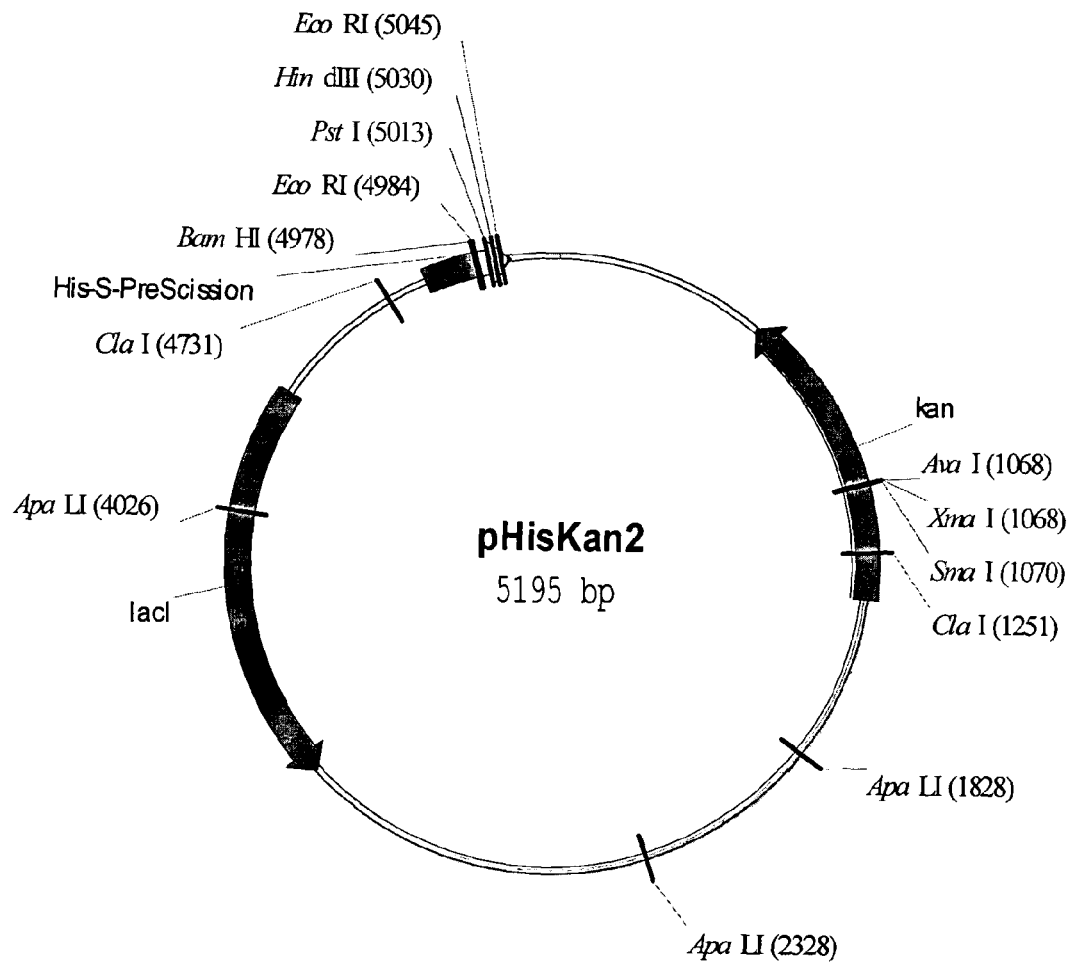
FIG. 6 is a diagram of the vector used for cloning the fibronectin cDNA.

The genes encoding the enriched fibronectin pools were cloned into pNAT40 vector shown in FIG. 6 and the constructs transformed into electro-competent Acella *E. coli* strain (Gaithersburg, Md.). A number of clones were selected and sequenced. The amino acid sequences of selected clones of potential Fn3-based binders for HSA are shown in FIG. 7, along with a consensus binding sequence (SEQ ID NO: 42). FIG. 8 shows the amino acid sequences of selected clones of potential Fn3-based binders for lysozyme.

Individual clones from the HSA library were selected and used to inoculate 1 ml of OvernightExpress media (Novagen, Gibbstown, N.J.) containing 100 ng/ml Kanamycin in a 96 deep-well plate using a colony picker (Genetix Clonepix2, Boston, Mass.) and grown overnight at 37° C. with vigorous shaking. The following day the cell pellets were harvested by centrifugation at 3000 rpm for 15 min and the supernatant discarded. The deep-well plates were frozen twice for 30 min at −80° C. and thawed at room temperature. Subsequently, 250 µl lysis-buffer containing TBS with 0.2 mg/ml lysozyme and 1 mM EDTA was added and the plates incubated at room temperature for 1 hour followed by the addition of 250 µl TBS containing 0.1 mg/ml DNaseI, 10 mM $MgCl_2$ and incubation for another 1 hour at room temperature.

The lysed cell suspension was transferred onto 96 well Multiscreen HTS (Millipore, Billerica, Mass.) and the supernatant cleared by centrifugation. The cleared supernatant containing the potential Fn3-based binders for HSA was subsequently used for ELISA assay as described below in Example 5.

Example 5

Binding Characterization of Monospecific Fibronectin-Based Binding Molecules

This Example illustrates, for the first time, that Fn3-based binding molecules can be generated by modifying at least one of the bottom loops of Fn3 (e.g., loops AB, CD and/or EF), to successfully produce Fn3-based molecules that bind to a target using the bottom loops. In this Example, the potential Fn3-based binders for HSA were examined.

To evaluate the binding characteristics, ELISA assays were used. Each well of a pretreated ELISA plate (Nunc Maxisorb) was coated with 100 µl of 1.0 µg/mL HSA in PBS covered with plastic film and incubated at 4° C. overnight. The next day the coating solution was removed and the plates washed twice with PBS. The wells were blocked by adding 200 µL 25 mg/ml Casein/PBS per well and incubated for 1 hour at 37° C., in a moist sealed container. After removing of the blocking solution and washing twice with PBS 50 µl of the previously prepared *E. coli* lysate expressing potential monospecific binders was added and incubated with shaking for 1 hour. Subsequently the plates were washed 5 times with PBS/Tween 20 (0.05%) buffer followed by the addition of HRP conjugated anti-His-tag antibody (Abcam, Cambridge, Mass.) preparation diluted in 0.25% casein/PBS, 50 µL per well. After incubation for 1 hour, the His-tag antibody solution was removed and the plates washed 5 times with PBS/Tween 20 (0.05%). Finally the ELISA was developed by adding substrate solution (SureBlue TMB microwell substrate solution, KPL) 50 µL per well. Positive clones were selected and subsequently expression screened to identify candidates for scale-up production.

Figure 9:
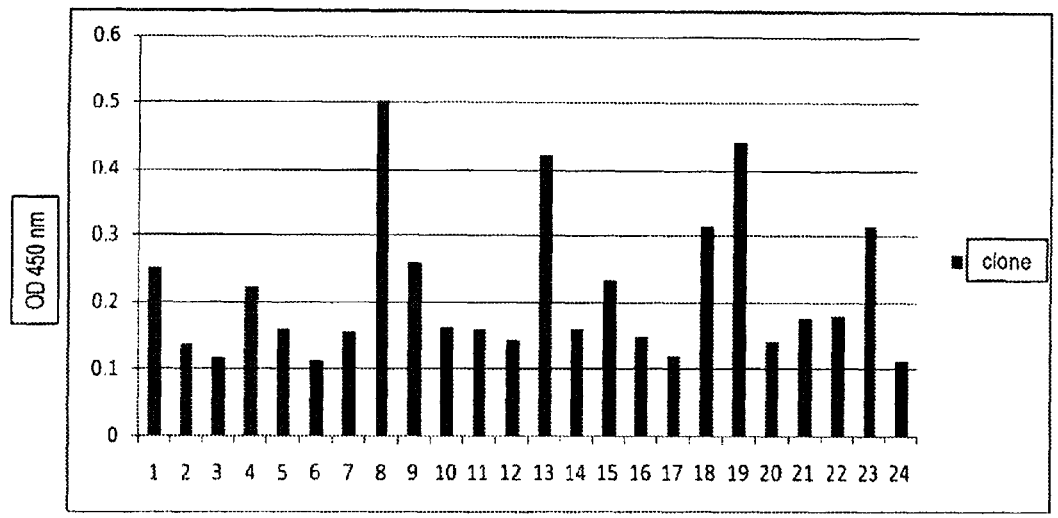
FIG. 9 is a graph showing human serum albumin specific ELISA analysis of His-tagged monospecific Fn3-based binding molecules that use the bottom loops or C-terminal to bind human serum albumin as the specific target.

FIG. 9 shows representative, non-limiting examples of a human serum albumin-specific ELISA analysis of His-tagged fibronectin protein from selected clones. Crude lysates of soluble fibronectin Fn10 domains were added to wells of an ELISA plate, which were coated with HSA antigen and additionally blocked with PBS+1% casein. Detection of Fn3-based binders for HSA was performed using a monoclonal HRP conjugated anti-His antibody. The ELISA was developed by a TMB-substrate as described above. The OD-values (Y-axis) were measured at 450 nm by an ELISA-reader. Each bar represents an individual clone extract. The data shows a number of clones that are positive Fn3-based binders for HSA displaying binding that is about 3-fold higher than the background. The results demonstrate, for the first time, that the bottom loops of the fibronectin molecule can be used to bind to a target, such as HSA.

To purify the expressed monospecific Fn3-based binders for HSA, the cleared lysate was transferred into a 96 well deep well block and 20 µL of a 50% (v/v) slurry of $Ni^{2+}$-loaded MagneHis beads (Promega) added. Automated purification was performed using a KingFisher Robot (Thermo Scientific) . After a 30 min incubation the beads were washed twice with 1 ml wash buffer/well (50 mM Phosphate, 1 M NaCl, 20 mM Imidazole, pH 7.6). Finally bound fibronectin protein was eluted with 200 µl of PBS+300 mM Imidazole at pH 7.6. Aliquots of the crude extract and elute were analyzed by SDS gel-electrophoresis (data not shown).

Figure 10:
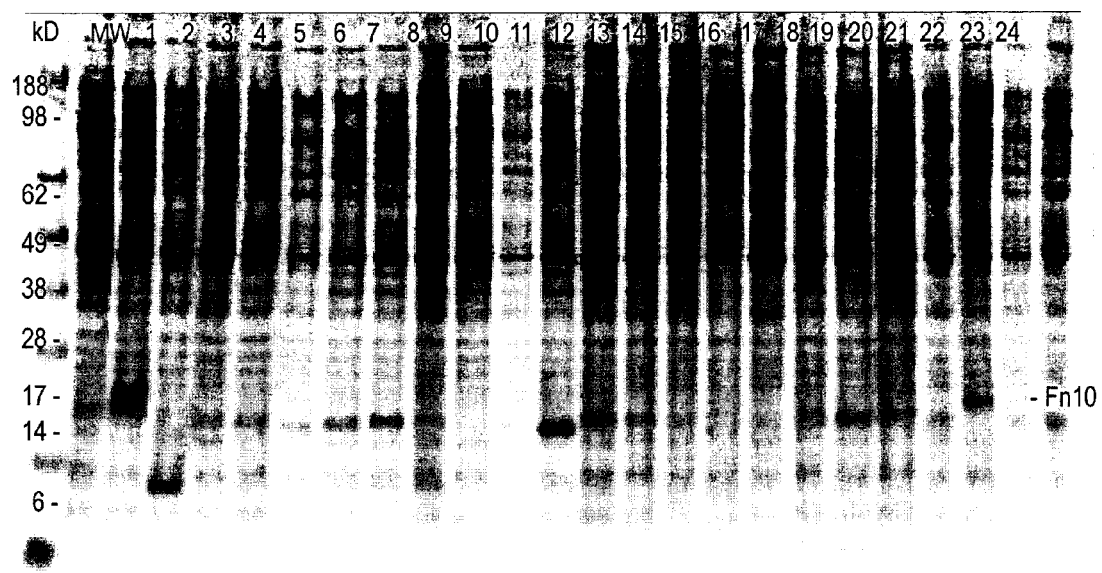
FIG. 10 is an SDS-PAGE gel showing successful expression in *E. coli* of monospecific Fn3-based binding molecules that use the bottom loops or C-terminal to bind a specific target.
Figure 11:
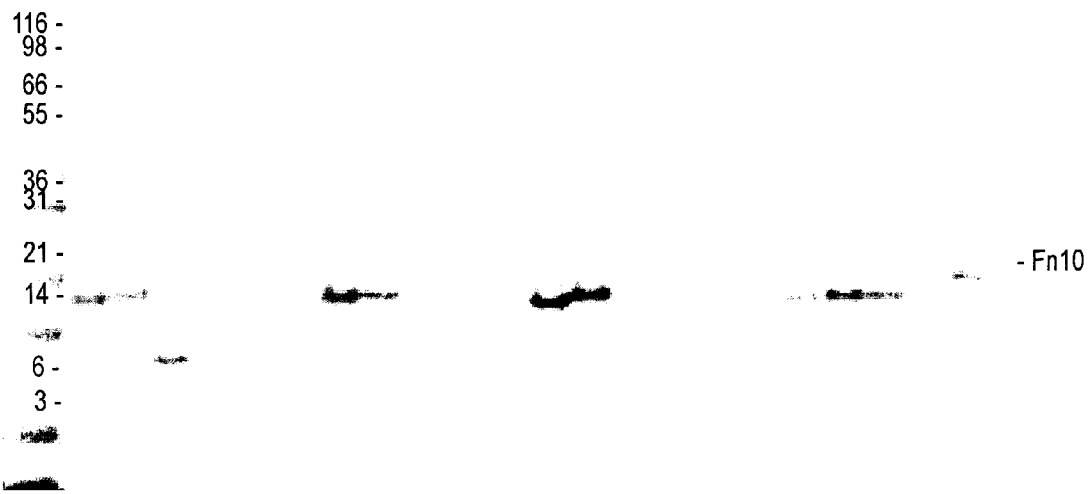
FIG. 11 is an SDS-PAGE gel showing successful purification from *E. coli* lysates of monospecific Fn3-based binding molecules that use the bottom loops or C-terminal to bind a specific target.

To further demonstrate that the bottom side Fn3-based binders for HSA can be successfully expressed, a small-scale total expression experiment was conducted in *E. coli*. Samples from total expression of 24 constructs were analyzed on a Novex BisTris 4-2% NuPAGE gel, 26 wells (Invitrogen). Lane 1 contains size marker SeeBlue plus2 (Invitrogen). The results shows successful expression of fibronectin molecules with modified bottom loops in *E. coli*. A protein band at about 16 kDa (corresponding to fibronectin Fn10 (~11-12 kDa) plus N-terminal His-tag, S-tag and prescission cleavage site) appears in a majority of the selected clones, as shown in FIG. 10. These results further demonstrate that the monospecific Fn3-based binding molecule can successfully be expressed in *E. coli* and retain binding activity.

To show the that the expressed proteins can be purified without adverse effect on the protein structure (e.g., degradation), the samples were purified as described above and analyzed on a Novex BisTris 4-12% NuPAGE gel, 26 wells (Invitrogen). Lane 1 contains size marker Mark 12 (Invitrogen). The 16 kDa band clearly appears in most of the clones, as shown in FIG. 10. Mass spectrometry analysis confirms the presence of fibronectin at the correct molecular weight being purified, as shown in Table 1.

TABLE 1

Mass Spectrometry Analysis of Fn3-based Fibronectin Binding Molecules

| Clone number | Molecular Weight |
| --- | --- |
| Clone 1 | 16076 |
| Clone 2 | 16265 |
| Clone 3 | 12112 |
| Clone 4 | ND |
| Clone 5 | 16395 |
| Clone 6 | ND |
| Clone 7 | 16274 |
| Clone 8 | 16321 |
| Clone 9 | ND |
| Clone 10 | ND |
| Clone 11 | ND |
| Clone 12 | 16274 |
| Clone 13 | 16394 |
| Clone 14 | ND |
| Clone 15 | ND |
| Clone 16 | ND |
| Clone 17 | ND |
| Clone 18 | 16482 |
| Clone 19 | 16275 |
| Clone 20 | 16380 |

TABLE 1-continued

Mass Spectrometry Analysis of Fn3-based Fibronectin Binding Molecules

| Clone number | Molecular Weight |
| --- | --- |
| Clone 21 | 16274 |
| Clone 22 | 18319 |
| Clone 23 | ND |
| Clone 24 | ND |

ND = not determined

Collectively, the results show for the first time that Fn3-based binding molecules can be generated in which at least one of the bottom loops is modified such that it binds to a target. To date, the top loops have typically been analyzed for binding to targets, primarily due to the better alignment of the top loops with antibody sequences compared with the bottom loops. The results presented herein demonstrate that the bottom loops can be modified without adversely affecting the stability of the molecule. Thus, a library of Fn3-based binding molecules can be generated in which at least one of the bottom loops is modified such that it binds to a target. With the HSA library, the bottom loops were kept at the same length as wild type Fn3 and modified. With the lyzozyme library, the bottom loops were varied in length compared with wild type Fn3 without adverse effects on the protein structure. Furthermore, these monospecific Fn3-based binding molecules with the modified bottom loops, maintain conformational stability and can be expressed and purified while retaining binding ability. Thus, the methods of the invention can be used to generate a library of Fn3-based binding molecules that have at least one modified bottom loop as well as Fn3-based binding molecules that use the bottom face to bind a target.

Example 6

Generation and Characterization of Multispecific Fibronectin-Based Binding Molecules This Example demonstrates the production and characterization of a multispecific Fn3-based binding molecule, in which two separate monospecific Fn3-based binding molecules are linked together in a pearl-like fashion, using a linker sequence to generate a multispecific, e.g., bispecific molecule. The bispecific molecule was designed as follows. The VEGFR2 binding sequence shown below (SEQ ID NO: 117) was fused to the identified bottom side HSA binder, identified in FIG. 7 and shown below (SEQ ID NO: 8), using a short GS linker sequence GGGGSGGGGS (SEQ ID NO: 118), to generate a multispecific Fn3-based binding molecule with SEQ ID NO: 119, shown below. The constructs were synthesized by DNA2.0 and sub-cloned into expression vector pjExpress 401. Cloning, purification and ELISA followed standard protocols as outlined above.

```
VEGFR top side sequence
                                      (SEQ ID NO: 117)
MGVSDVPRDLEVVAATPTSLLISWRHPHFPTRYYRITYGETGGNSPVQ

EFTVPLQPPLATISGLKPGVDYTITVYAVTKERNGRELFTPISINYRT

Bottom side sequence 8 from FIG. 7
                                      (SEQ ID NO: 8)
VSDVPRDLEVVAATPTSLLISWDAPAVTVRYYRITYGRTDAKSTRKEF

TVPGSKSTATIGELKRGRDYTITVYAVTGRGDSPASSKPISINYRPEK

VEGFR2-Bottom sequence 8 from FIG. 7 fused with
GS linker (clone 87)
                                      (SEQ ID NO: 119)
MGVSDVPRDLEVVAATPTSLLISWRHPHFPTRYYRITYGETGGNSPVQ

EFTVPLQPPLATISGLKPGVDYTITVYAVTKERNGRELFTPISINYRT

GGGGSGGGGSVSDVPRDLEVVAATPTSLLISWDAPAVTVRYYRITYGR

TDAKSTRKEFTVPGSKSTATIGELKRGRDYTITVYAVTGRGDSPASSK

PISINYRPEKENLYFQGHHHHHH
```

Figure 13:
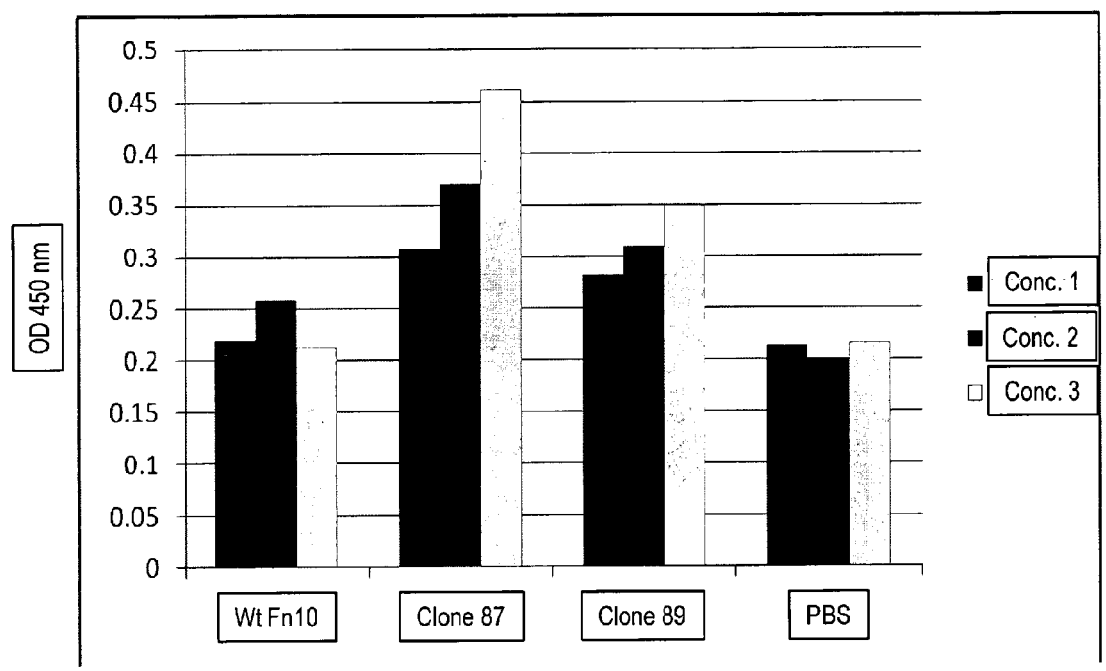
FIG. 13 is a graph showing ELISA analysis of bispecific Fn3-based binding molecules that use both the bottom loops or C-terminal and the top loops to bind different target molecules. Bispecific Fn3-based binding molecules isolated from clone 87 and clone 89 have top loops that bind VEGFR2 and bottom loops that bind human serum albumin. The data shows that a single Fn3-based binding molecule can be engineered such that the top loops bind to VEGFR2 and the bottom loops bind to HSA.

The ELISA binding studies of the multispecific molecule is shown in FIG. 13 and discussed in more detail in Example 7.

To demonstrate that the multispecific Fn3-based binding molecule can purified from a large scale expression of the molecule, the procedure outlined by Gräslund et al., was used (Gräslund et al. *Nature Methods* (2008) 5, 135-146). Starter cultures of 10 ml (~1/100 of the final cultivation volume) were used to inoculate Minimal Media containing 25 ug/ml Kanamycin and incubated overnight at 37° C. at 175 rpm. The following morning, 10 ml of the starter culture was used to inoculated into 1 liter of OvernightExpress media with 100 ug/ml Kanamycin in a 2.8 L Fernbach shake flask. The cells were incubated at 37° C. at 175 rpm until an optical density at 600 nm (OD600) of 1-1.5 was reached. The temperature of the culture was then lowered to 18° C. to switch on expression and the cultures maintained overnight at 18° C. for continued expression. The cells were harvested by centrifugation at 4500×g for 10 min. The cells were weighed, and 1 volume (v/w) of lysis buffer (0.1 M sodium phosphate, pH 8.0, 1.0 M NaCl, 20 mM imidazole, 10% (v/v) glycerol, 1 mM TCEP, and 20 units/ml Benzonase) was added. 1 mg/ml lysozyme was added to the cell suspension and after incubation for 30 min on ice, the suspension sonicated intermittently for 1-2 minutes. The lysate was diluted with 2-3 volumes of Lysis buffer and 1 ml Ni-NTA resin was added. Binding was performed by slowly rotating the supernatant in a 250 ml conical vial at 4° C. for 1 hour. The resin was collected in a 20 ml disposable column and washed with loading buffer (0.05 M sodium phosphate, pH 8.0, 0.5 M NaCl, 20 mM imidazole, 5% (v/v) glycerol, 0.5 mM TCEP) until no more protein eluted (20-30 column volumes of each). The bound protein was eluted with elution buffer (0.05 M sodium phosphate, pH 8.0, 0.5 M NaCl, 0.3 M imidazole, 5% (v/v) glycerol, 0.5 mM TCEP). Peak fractions were identified, pooled together and loaded onto an equilibrated MonoS 5/50 GL column (GE) with buffer S (50 mM Hepes, 50 mM NaCl pH 7.6). The Ni-NTA elute was diluted 10 fold with buffer S and load onto the pre-equilibrated column. After washing with 10 volumes of Buffer S the protein was eluted with a linear gradient from 50 mM to 1 M NaCl in buffer S. Fractions were analysed by SDS-PAGE and mass spectrometry.

Figure 12:
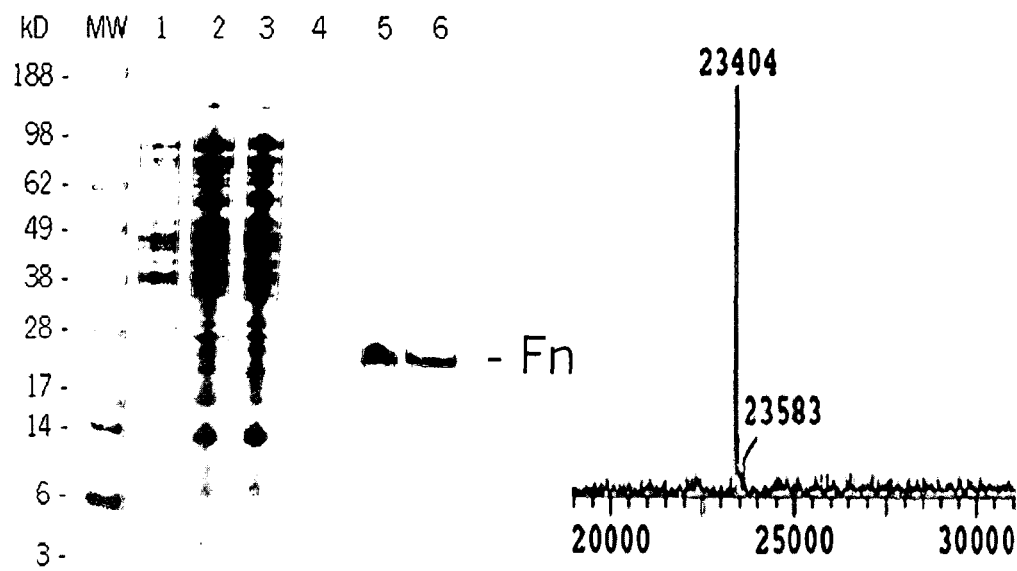
FIG. 12 is an SDS-PAGE gel showing successful purification from *E. coli* lysates of bispecific Fn3-based binding molecules that use the bottom loops or C-terminal to bind a specific target.

FIG. 12 The left panel shows the SDS-PAGE of the different purification steps of clone 87. Lane 1, total protein; lane 2, crude extract; lane 3, Ni-NTA flow through; lane 4, Ni-NTA wash; lane 5, Ni-NTA, elute; lane 6, Mono S elute. The right panel shows the mass spectrum of the purified sample (MW 23404 D) consistent with the expected mass of the N-terminal methionine cleaved protein of clone 87.

Example 7

Generation and Characterization of Bispecific Fibronectin-Based Binding Molecules This Example demonstrates the production and characterization of a bispecific Fn3-based binding molecule in which a single fibronectin molecule has both the top loops and the bottom loops modified such that the single fibronectin molecule can bind two separate targets, e.g., VEGFR2 and HSA.

A bispecific molecule was generated by crafting the bottom side HSA binding loop sequence onto the top-side VEGFR2 binders generating a molecule with bispecific functionality in which both the top and bottom loops of the same Fn3 molecule can be used to bind to two different target molecules. To create the bispecific molecule, the bottom side binder (SEQ ID NO: 8) loops (shown above) were crafted onto the VEGFR2 binder (SEQ ID NO: 117) (shown above) by excising the bottom loops and inserting them into the VEGFR2 binder, yielding molecule VEGFR2-HAS (SEQ ID NO: 120). The constructs were synthesized by DNA2.0 and sub-cloned into expression vector pjExpress 401. Cloning, purification and ELISA followed standard protocols as outlined above.

VEGFR2/Bottom side SEQ ID NO: 8 merged molecule
(clone 89)
(SEQ ID NO: 120)
MGVSDVPRDLEVVAATPTSLLISWRHPHFPTRYYRITYGRTDAKSTRK

EFTVPLQPPLATIGELKRGRDYTITVYAVTKERNGRELFTPISINYRP

EKENLYFQGHHHHHH (a) ELISA for Dual-Specific Fibronectin Binding Molecules from Examples 6 and 7:

The binding characteristic of the multispecific and bispecific binders from Examples 6 and 7 were assessed as follows. VEGFR2-Fc fusion protein was immobilized onto a pre-treated ELISA plate (NuncMultisorb) and additionally blocked with PBS+1% Casein. Aliquots of cleared lysate of wild-type Fn10 (lane1), clone 87 (multispecific) (lane2), clone 89 (bispecific) (lane3) and PBS were added to the wells and incubated for 1 hour at room-temperature. These were run at different concentrations 1, 2 and 3. After washing 5 times with PBS/0.05% Tween, the wells were incubated with 1 µg/ml HSA in PBS. Detection was performed with HRP conjugated chicken anti-human HSA antibody (Abcam). The ELISA was developed with a TMP substrate and the OD-values measured at 450 nm. The results are shown in FIG. 13.

Consistent reproducible results were obtained with both mutispecific and bispecific Fn3-based binding molecules present in crude extract, showing that clone 87 (multispecific) and clone 89 (bispecific) bind to both HSA and VEGFR2. This data demonstrates that multispecific and bispecific Fn3 molecules can be produced where on of the monospecific fibronectin binding molecules has at least one modified bottom loop (AB, DE, FG) that can bind HSA (see FIG. 13).

The multispecific Fn3 molecule (clone 87) has two separate monospecific Fn3 molecules linked together via a G-S linker. One monospecific Fn3 molecule has modified bottom loops that bind to HSA while the other monospecific Fn3 molecule has modified top loops that bind to VEGFR2. The resulting multispecific molecule retains the ability to bind to two different targets using each of the monospecific fibronectin molecules. This data shows that monospecific Fn3 molecules can be linked together in a pearl-like manner to create a multispecific Fn3 molecule; that the linker does not interfere with the binding ability of each of the monomeric Fn3 molecules; and that the multispecific Fn3 molecule is able to bind to two different targets without any steric hinderance issues.

The bispecific fibronectin molecule (clone 89) is a single fibronectin molecule engineered such that the bottom loops bind to HSA and the top loops bind to VEGFR2. The single bispecific fibronectin molecule successfully binds both HSA and VEGFR2 FIG. 13 shows that the single bispecific fibronectin molecule is able to bind both HSA and VEGFR2 without any steric hinderance issues. This data shows, for the first time, that bispecific fibronectin molecules can be produced; that the binding ability of the loops on each side of the bispecific fibronectin molecule is retained; that the structural confirmation of the bispecific molecule is maintained with both bottom and top loops being modified at the same time; that the top and bottom loops function independently of each other to bind separate targets; and that the bispecific Fn3 molecule is able to bind to two different targets without any steric hinderance issues.

(b) Biacore for Dual-Specific Fibronectin Binding Molecules from Examples 6 and 7:

The binding kinetics of fibronectin-based scaffold proteins binding proteins to the target was measured using BIAcore T100 (GE). Anti-hu IgG (GE, human IgG capture kit) Fc specific antibody was immobilized onto a CM5 sensor chip and soluble VEGFR2-huFc fusion protein captured on the surface. Soluble Fibronectin clone 87 (multispecific) was injected at 100 nM (top line) and 200 nM (bottom line) in buffer 0 (10 mM HEPES, 150 mM NaCl, 0.005% Tween 20, pH 7.4). Sensorgrams were obtained at each concentration and the rate constants ka (kon) and kd (koff) determined. The affinity constant, KD was calculated from the ratio of rate constants koff/kon.

Figure 14:
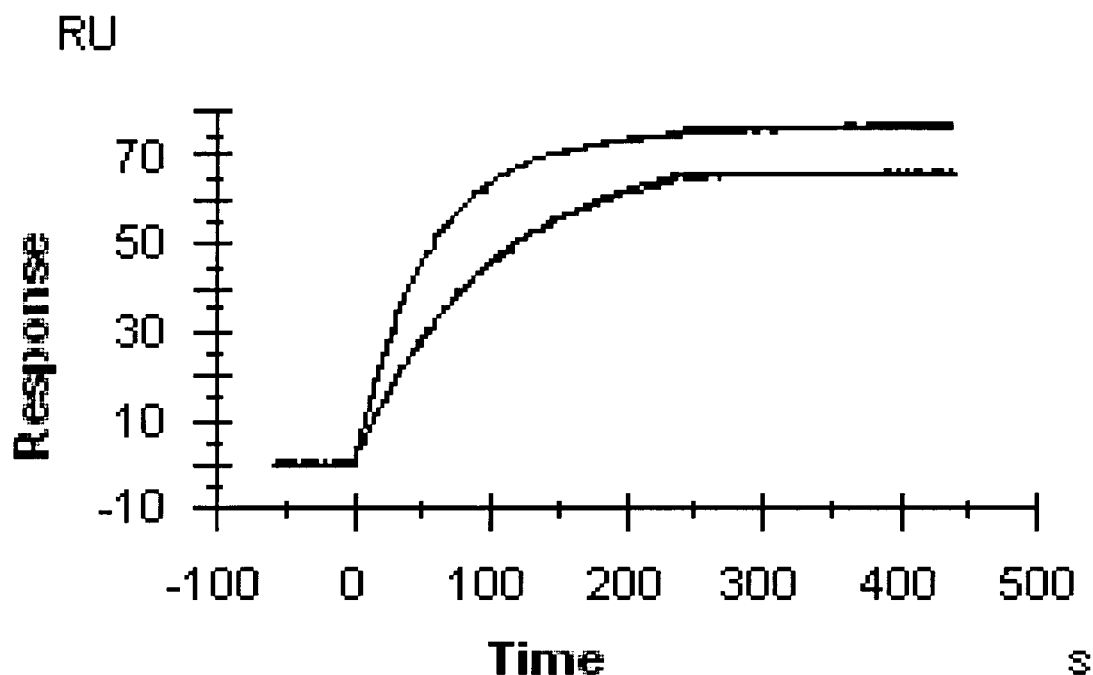
FIG. 14 is a graph showing Biacore binding study of a bispecific Fn3-based binding molecule isolated from clone 87 that uses the top loops to bind VEGFR2.
Figure 15:
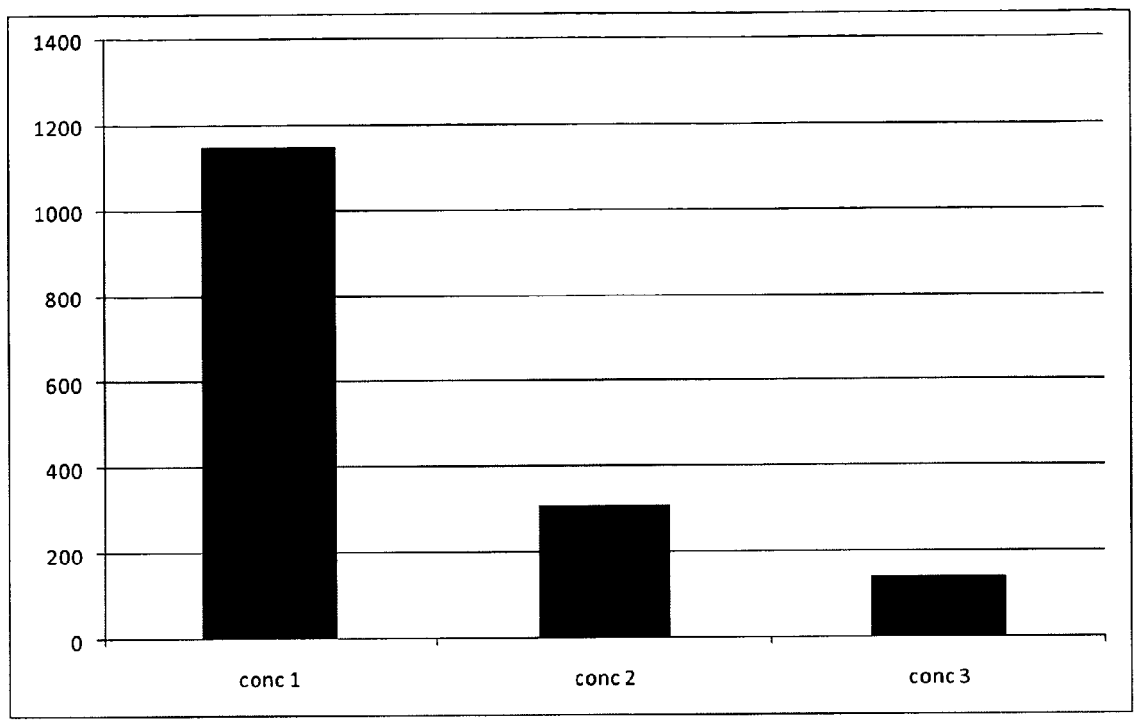
FIG. 15 is a graph showing Biacore binding study of a bispecific Fn3-based binding molecule isolated from clone 87 that uses the bottom loops or C-terminal to bind HSA.

The results for clone 87 are shown in FIGS. 14 and 15 for the top loop binding VEGFR2 and the bottom loop binding HSA, respectively. This data shows the multispecific fibronectin comprising two separate monospecific Fn3 molecules linked together with a G-S linker, successfully binds to two separate target molecules using the bottom and top loops.

The same experiment was repeated for clone 89, the single bispecific Fn3 molecule and similar results obtained (data not shown).

Collectively, these results show for the first time that multispecific and bispecific fibronectin molecules can be produced. These molecules were successfully expressed in *E. coli*, were be purified without degradation, retained binding ability, and were able to bind to two separate targets.

EQUIVALENTS

Those skilled in the art will recognize or be able to ascertain, using no more than routine experimentation, many equivalents of the specific embodiments of the invention described herein. Such equivalents are intended to be encompassed by the following claims.

The invention claimed is:

1. An Fn3-based binding molecule comprising SEQ ID NO: 120.

* * * * *